United States Patent
Weinstein et al.

(10) Patent No.: US 10,479,793 B2
(45) Date of Patent: Nov. 19, 2019

(54) IMIDAZOPYRIDAZINE COMPOUNDS USEFUL AS MODULATORS OF IL-12, IL-23 AND/OR IFN ALPHA RESPONSES

(71) Applicant: BRISTOL-MYERS SQUIBB COMPANY, Princeton, NJ (US)

(72) Inventors: David S. Weinstein, San Diego, CA (US); Ryan M. Moslin, Princeton, NJ (US); Yanlei Zhang, Princeton, NJ (US); Daniel S. Gardner, Furlong, PA (US); Joseph B. Santella, Springfield, PA (US); Charles M. Langevine, Brooklyn, NY (US); Sylwia Stachura, Flemington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/776,094

(22) PCT Filed: Nov. 17, 2016

(86) PCT No.: PCT/US2016/062396
§ 371 (c)(1),
(2) Date: May 15, 2018

(87) PCT Pub. No.: WO2017/087590
PCT Pub. Date: May 26, 2017

(65) Prior Publication Data
US 2018/0325899 A1 Nov. 15, 2018

Related U.S. Application Data

(60) Provisional application No. 62/404,827, filed on Oct. 6, 2016, provisional application No. 62/256,784, filed on Nov. 18, 2015.

(51) Int. Cl.
| | | |
|---|---|---|
| C07D 487/04 | (2006.01) | |
| A61P 37/02 | (2006.01) | |
| A61P 29/00 | (2006.01) | |
| A61K 31/5025 | (2006.01) | |
| A61K 31/53 | (2006.01) | |
| A61K 31/5377 | (2006.01) | |

(52) U.S. Cl.
CPC ........ C07D 487/04 (2013.01); A61K 31/5025 (2013.01); A61K 31/53 (2013.01); A61K 31/5377 (2013.01); A61P 29/00 (2018.01); A61P 37/02 (2018.01)

(58) Field of Classification Search
CPC .................................................. C07D 487/04
See application file for complete search history.

(56) References Cited

U.S. PATENT DOCUMENTS

2010/0323994 A1* 12/2010 Fink ..................... C07D 487/04
514/157
2011/0046127 A1* 2/2011 Pevarello ............ C07D 487/04
514/230.8

FOREIGN PATENT DOCUMENTS

| | | | |
|---|---|---|---|
| WO | WO 2009/060197 A1 | 5/2009 | |
| WO | WO 2009/100375 A1 | 8/2009 | |
| WO | WO 2013/059587 A1 | 4/2013 | |
| WO | WO 2013/134219 A1 | 9/2013 | |
| WO | PCT/US2014/069476 | 12/2014 | |
| WO | WO 2015/089143 A1 | 6/2015 | |
| WO | WO-2015089143 A1 * | 6/2015 | ........... C07D 487/14 |
| WO | PCT/US2017/054710 | 10/2017 | |
| WO | PCT/US2017/061895 | 11/2017 | |

OTHER PUBLICATIONS

Cleveland Clinic, Psoriasis: Prevention, https://my.clevelandclinic.org/health/diseases/6866-psoriasis/prevention, accessed Mar. 4, 2019 (Year: 2019).*
Soeken et al. Rheumatology 2003, 42, 652-659 (Year: 2003).*
Mayo Clinic, Asthma—Prevention, http://www.mayoclinic.org/diseases-conditions/asthma/basics/prevention/con-20026992, accessed Mar. 4, 2019 (Year: 2019).*
Database Registry, Chemical Abstracts Service, May 29, 2009, XP-002766276.
Database Registry, Chemical Abstracts Service, May 29, 2009, XP-002766277.
Database Registry, Chemical Abstracts Serivice, May 29, 2009, XP-002766278.
Databaase Registry, Chemical Abstracts Service, May 29, 2009, XP002766279.
Database Registry, Chemical Abstracts Service, May 29, 2009, XP-002766280.
U.S. Appl. No. 15/102,991, filed Jun. 9, 2016, pending.

* cited by examiner

Primary Examiner — Matthew P Coughlin
(74) Attorney, Agent, or Firm — Elliott Korsen

(57) ABSTRACT

Compounds of formula I or a stereoisomer or pharmaceutically-acceptable salt thereof, are useful in the modulation of IL-12, IL-23 and/or IFNα, by acting on Tyk-2 to cause signal transduction inhibition.

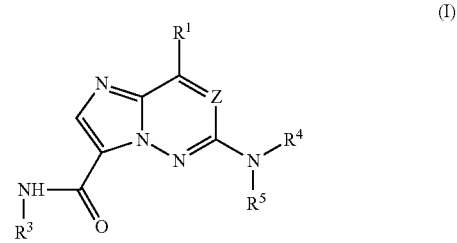

(I)

3 Claims, No Drawings

Specification includes a Sequence Listing.

SEQUENCE LISTING

<160> NUMBER OF SEQ ID NOS: 1

<210> SEQ ID NO 1
<211> LENGTH: 317
<212> TYPE: PRT
<213> ORGANISM: Homo sapiens

<400> SEQUENCE: 1

```
Met Gly Ser Ser His His His His His His Ser Ser Gly Glu Thr Val
1               5                   10                  15

Arg Phe Gln Gly His Met Asn Leu Ser Gln Leu Ser Phe His Arg Val
            20                  25                  30

Asp Gln Lys Glu Ile Thr Gln Leu Ser His Leu Gly Gln Gly Thr Arg
        35                  40                  45

Thr Asn Val Tyr Glu Gly Arg Leu Arg Val Glu Gly Ser Gly Asp Pro
    50                  55                  60

Glu Gly Lys Met Asp Asp Glu Asp Pro Leu Val Pro Gly Arg Asp
65                  70                  75                  80

Arg Gly Gln Glu Leu Arg Val Val Leu Lys Val Leu Asp Pro Ser His
                85                  90                  95

His Asp Ile Ala Leu Ala Phe Tyr Glu Thr Ala Ser Leu Met Ser Gln
            100                 105                 110

Val Ser His Thr His Leu Ala Phe Val His Gly Val Cys Val Arg Gly
        115                 120                 125

Pro Glu Asn Ile Met Val Thr Glu Tyr Val Glu His Gly Pro Leu Asp
    130                 135                 140

Val Trp Leu Arg Arg Glu Arg Gly His Val Pro Met Ala Trp Lys Met
145                 150                 155                 160

Val Val Ala Gln Gln Leu Ala Ser Ala Leu Ser Tyr Leu Glu Asn Lys
                165                 170                 175

Asn Leu Val His Gly Asn Val Cys Gly Arg Asn Ile Leu Leu Ala Arg
            180                 185                 190

Leu Gly Leu Ala Glu Gly Thr Ser Pro Phe Ile Lys Leu Ser Asp Pro
        195                 200                 205

Gly Val Gly Leu Gly Ala Leu Ser Arg Glu Glu Arg Val Glu Arg Ile
    210                 215                 220

Pro Trp Leu Ala Pro Glu Cys Leu Pro Gly Gly Ala Asn Ser Leu Ser
225                 230                 235                 240

Thr Ala Met Asp Lys Trp Gly Phe Gly Ala Thr Leu Leu Glu Ile Cys
                245                 250                 255

Phe Asp Gly Glu Ala Pro Leu Gln Ser Arg Ser Pro Ser Glu Lys Glu
            260                 265                 270
```

```
His Phe Tyr Gln Arg Gln His Arg Leu Pro Glu Pro Ser Cys Pro Gln
        275                 280                 285

Leu Ala Thr Leu Thr Ser Gln Cys Leu Thr Tyr Glu Pro Thr Gln Arg
        290                 295                 300

Pro Ser Phe Arg Thr Ile Leu Arg Asp Leu Thr Arg Leu
305                 310                 315
```

IMIDAZOPYRIDAZINE COMPOUNDS USEFUL AS MODULATORS OF IL-12, IL-23 AND/OR IFN ALPHA RESPONSES

CROSS-REFERENCE TO RELATED APPLICATIONS

This application claims the benefit of U.S. Provisional Application No. 62/256,784, filed Nov. 18, 2015, and U.S. Provisional Application No. 62/404,827, filed Oct. 6, 2016, the disclosures of which are incorporated herein by reference in their entirety.

FIELD OF THE INVENTION

This invention relates to compounds useful in the modulation of IL-12, IL-23 and/or IFNα by acting on Tyk-2 to cause signal transduction inhibition. Provided herein are imidazopyradazine compounds, compositions comprising such compounds, and methods of their use. The invention further pertains to pharmaceutical compositions containing at least one compound according to the invention that are useful for the treatment of conditions related to the modulation of IL-12, IL-23 and/or IFNα in a mammal.

BACKGROUND OF THE INVENTION

The heterodimeric cytokines interleukin IL-12 and IL-23, which share a common p40 subunit, are produced by activated antigen-presenting cells and are critical in the differentiation and proliferation of Th1 and Th17 cells, two effector T cell lineages which play key roles in autoimmunity. IL-23 is composed of the p40 subunit along with a unique p19 subunit. IL-23, acting through a heterodimeric receptor composed of IL-23R and IL-12Rβ1, is essential for the survival and expansion of Th17 cells which produce pro-inflammatory cytokines such as IL-17A, IL-17F, IL-6 and TNF-α (McGeachy, M. J. et al., "The link between IL-23 and Th17 cell-mediated immune pathologies", *Semin. Immunol.*, 19:372-376 (2007)). These cytokines are critical in mediating the pathobiology of a number of autoimmune diseases, including rheumatoid arthritis, multiple sclerosis, inflammatory bowel disease, and lupus. IL-12, in addition to the p40 subunit in common with IL-23, contains a p35 subunit and acts through a heterodimeric receptor composed of IL-12Rβ1 and IL-12Rβ2. IL-12 is essential for Th1 cell development and secretion of IFNγ, a cytokine which plays a critical role in immunity by stimulating MHC expression, class switching of B cells to IgG subclasses, and the activation of macrophages (Gracie, J. A. et al., "Interleukin-12 induces interferon-gamma-dependent switching of IgG alloantibody subclass", Eur. J. Immunol., 26:1217-1221 (1996); Schroder, K. et al., "Interferon-gamma: an overview of signals, mechanisms and functions", *J. Leukoc. Biol.*, 75(2):163-189 (2004)).

The importance of the p40-containing cytokines in autoimmunity is demonstrated by the discovery that mice deficient in either p40, p19, or IL-23R are protected from disease in models of multiple sclerosis, rheumatoid arthritis, inflammatory bowel disease, lupus and psoriasis, among others (Kyttaris, V. C. et al., "Cutting edge: IL-23 receptor deficiency prevents the development of lupus nephritis in C57BL/6-lpr/lpr mice", *J. Immunol.*, 184:4605-4609 (2010); Hong, K. et al., "IL-12, independently of IFN-gamma, plays a crucial role in the pathogenesis of a murine psoriasis like skin disorder", *J. Immunol.*, 162:7480-7491 (1999); Hue, S. et al., "Interleukin-23 drives innate and T cell-mediated intestinal inflammation", *J. Exp. Med.*, 203:2473-2483 (2006); Cua, D. J. et al., "Interleukin-23 rather than interleukin-12 is the critical cytokine for autoimmune inflammation of the brain", *Nature*, 421:744-748 (2003); Murphy, C. A. et al., "Divergent pro- and anti-inflammatory roles for IL-23 and IL-12 in joint autoimmune inflammation", J. Exp. Med., 198:1951-1957 (2003)).

In human disease, high expression of p40 and p19 has been measured in psoriatic lesions, and Th17 cells have been identified in active lesions in the brain from MS patients and in the gut mucosa of patients with active Crohn's disease (Lee, E. et al., "Increased expression of interleukin 23 p19 and p40 in lesional skin of patients with psoriasis vulgaris", *J. Exp. Med.*, 199:125-130 (2004); Tzartos, J. S. et al., "Interleukin-17 production in central nervous system infiltrating T cells and glial cells is associated with active disease in multiple sclerosis", *Am. J. Pathol.*, 172:146-155 (2008)). The mRNA levels of p19, p40, and p35 in active SLE patients were also shown to be significantly higher compared with those in inactive SLE patients (Huang, X. et al., "Dysregulated expression of interleukin-23 and interleukin-12 subunits in systemic lupus erythematosus patients", *Mod. Rheumatol.*, 17:220-223 (2007)), and T cells from lupus patients have a predominant Th1 phenotype (Tucci, M. et al., "Overexpression of interleukin-12 and T helper 1 predominance in lupus nephritis", *Clin. Exp. Immunol.*, 154:247-254 (2008)).

Moreover, genome-wide association studies have identified a number of loci associated with chronic inflammatory and autoimmune diseases that encode factors that function in the IL-23 and IL-12 pathways. These genes include IL23A, IL12A, IL12B, IL12RB1, IL12RB2, IL23R, JAK2, TYK2, STAT3, and STAT4 (Lees, C. W. et al., "New IBD genetics: common pathways with other diseases", *Gut*, 60:1739-1753 (2011); Tao, J. H. et al., "Meta-analysis of TYK2 gene polymorphisms association with susceptibility to autoimmune and inflammatory diseases", *Mol. Biol. Rep.*, 38:4663-4672 (2011); Cho, J. H. et al., "Recent insights into the genetics of inflammatory bowel disease", *Gastroenterology*, 140:1704-1712 (2011)).

Indeed, anti-p40 treatment, which inhibits both IL-12 and IL-23, as well as IL-23-specific anti-p19 therapies have been shown to be efficacious in the treatment of autoimmunity in diseases including psoriasis, Crohn's Disease and psoriatic arthritis (Leonardi, C. L. et al., "PHOENIX 1 study investigators. Efficacy and safety of ustekinumab, a human interleukin-12/23 monoclonal antibody, in patients with psoriasis: 76-week results from a randomized, double-blind, placebo-controlled trial (PHOENIX 1)", *Lancet*, 371:1665-1674 (2008); Sandbom, W. J. et al., "Ustekinumab Crohn's Disease Study Group. A randomized trial of Ustekinumab, a human interleukin-12/23 monoclonal antibody, in patients with moderate-to-severe Crohn's disease", *Gastroenterology*, 135:1130-1141 (2008); Gottlieb, A. et al., "Ustekinumab, a human interleukin 12/23 monoclonal antibody, for psoriatic arthritis: randomized, double-blind, placebo-controlled, crossover trial", *Lancet*, 373:633-640 (2009)). Therefore, agents which inhibit the action of IL-12 and IL-23 may be expected to have therapeutic benefit in human autoimmune disorders.

The Type I group of interferons (IFNs), which include the IFNα members as well as IFNβ, IFNε, IFNκ and IFNω, act through a heterodimer IFNα/β receptor (IFNAR). Type I IFNs have multiple effects in both the innate and adaptive immune systems including activation of both the cellular and humoral immune responses as well as enhancing the expression and release of autoantigens (Hall, J. C. et al., "Type I interferons: crucial participants in disease amplification in autoimmunity", *Nat. Rev. Rheumatol.*, 6:40-49 (2010)).

In patients with systemic lupus erythematosus (SLE), a potentially fatal autoimmune disease, increased serum levels of interferon (IFN)-α (a type I interferon) or increased expression of type I IFN-regulated genes (a so-called IFNα signature) in peripheral blood mononuclear cells and in affected organs has been demonstrated in a majority of patients (Bennett, L. et al., "Interferon and granulopoiesis signatures in systemic lupus erythematosus blood", *J. Exp. Med.*, 197:711-723 (2003); Peterson, K. S. et al., "Characterization of heterogeneity in the molecular pathogenesis of lupus nephritis from transcriptional profiles of laser-captured glomeruli", *J. Clin. Invest.*, 113:1722-1733 (2004)), and several studies have shown that serum IFNα levels correlate with both disease activity and severity (Bengtsson, A. A. et al., "Activation of type I interferon system in systemic lupus erythematosus correlates with disease activity but not with antiretroviral antibodies", *Lupus*, 9:664-671 (2000)). A direct role for IFNα in the pathobiology of lupus is evidenced by the observation that the administration of IFNα to patients with malignant or viral diseases can induce a lupus-like syndrome. Moreover, the deletion of the IFNAR in lupus-prone mice provides high protection from autoimmunity, disease severity and mortality (Santiago-Raber, M. L. et al., "Type-I interferon receptor deficiency reduces lupus-like disease in NZB mice", *J. Exp. Med.*, 197:777-788 (2003)), and genome-wide association studies have identified loci associated with lupus that encode factors that function in the type I interferon pathway, including IRF5, IKBKE, TYK2, and STAT4 (Deng, Y. et al., "Genetic susceptibility to systemic lupus erythematosus in the genomic era", *Nat. Rev. Rheumatol.*, 6:683-692 (2010); Sandling, J. K. et al., "A candidate gene study of the type I interferon pathway implicates IKBKE and IL8 as risk loci for SLE", *Eur. J. Hum. Genet.*, 19:479-484 (2011)). In addition to lupus, there is evidence that aberrant activation of type I interferon-mediated pathways are important in the pathobiology of other autoimmune diseases such as Sjögren's syndrome and scleroderma (Bave, U. et al., "Activation of the type I interferon system in primary Sjögren's syndrome: a possible etiopathogenic mechanism", *Arthritis Rheum.*, 52:1185-1195 (2005); Kim, D. et al., "Induction of interferon-alpha by scleroderma sera containing autoantibodies to topoisomerase I: association of higher interferon-alpha activity with lung fibrosis", *Arthritis Rheum.*, 58:2163-2173 (2008)). Therefore, agents which inhibit the action of type I interferon responses may be expected to have therapeutic benefit in human autoimmune disorders.

Tyrosine kinase 2 (Tyk2) is a member of the Janus kinase (JAK) family of nonreceptor tyrosine kinases and has been shown to be critical in regulating the signal transduction cascade downstream of receptors for IL-12, IL-23 and type I interferons in both mice (Ishizaki, M. et al., "Involvement of Tyrosine Kinase-2 in Both the IL-12/Th1 and IL-23/Th17 Axes In Vivo" *J. Immunol.*, 187:181-189 (2011); Prchal-Murphy, M. et al., "TYK2 kinase activity is required for functional type I interferon responses in vivo" *PLoS One*, 7:e39141 (2012)) and humans (Minegishi, Y. et al., "Human tyrosine kinase 2 deficiency reveals its requisite roles in multiple cytokine signals involved in innate and acquired immunity" *Immunity*, 25:745-755 (2006)). Tyk2 mediates the receptor-induced phosphorylation of members of the STAT family of transcription factors, an essential signal that leads to the dimerization of STAT proteins and the transcription of STAT-dependent pro-inflammatory genes. Tyk2-deficient mice are resistant to experimental models of colitis, psoriasis and multiple sclerosis, demonstrating the importance of Tyk2-mediated signaling in autoimmunity and related disorders (Ishizaki, M. et al., "Involvement of Tyrosine Kinase-2 in Both the IL-12/Th1 and IL-23/Th17 Axes In Vivo" *J. Immunol.*, 187:181-189 (2011); Oyamada, A. et al., "Tyrosine kinase 2 plays critical roles in the pathogenic CD4 T cell responses for the development of experimental autoimmune encephalomyelitis" *J. Immunol.* 183:7539-7546 (2009)).

In humans, individuals expressing an inactive variant of Tyk2 are protected from multiple sclerosis and possibly other autoimmune disorders (Couturier, N. et al., "Tyrosine kinase 2 variant influences T lymphocyte polarization and multiple sclerosis susceptibility" *Brain* 134:693-703 (2011)). Genome-wide association studies have shown other variants of Tyk2 to be associated with autoimmune disorders such as Crohn's Disease, psoriasis, systemic lupus erythematosus, and rheumatoid arthritis, further demonstrating the importance of Tyk2 in autoimmunity (Ellinghaus, D. et al., "Combined Analysis of Genome-wide Association Studies for Crohn Disease and Psoriasis Identifies Seven Shared Susceptibility Loci" *Am. J. Hum. Genet.* 90:636-647 (2012); Graham, D. et al. "Association of polymorphisms across the tyrosine kinase gene, TYK2 in UK SLE families" *Rheumatology* (Oxford) 46:927-930 (2007); Eyre, S. et al. "High-density genetic mapping identifies new susceptibility loci for rheumatoid arthritis" *Nat. Genet.* 44:1336-1340 (2012)).

In view of the conditions that may benefit by treatment involving the modulation of cytokines and/or interferons, new compounds capable of modulating cytokines and/or interferons, such as IL-12, IL-23 and/or IFNα, and methods of using these compounds may provide substantial therapeutic benefits to a wide variety of patients in need thereof.

SUMMARY OF THE INVENTION

The invention is directed to compounds of Formula I that are useful as modulators of IL-12, IL-23 and/or IFNα by inhibiting Tyk2-mediated signal transduction.

The present invention also provides processes and intermediates for making the compounds of the present invention.

The present invention also provides pharmaceutical compositions comprising a pharmaceutically acceptable carrier and at least one of the compounds of the present invention.

The present invention also provides a method for the modulation of IL-12, IL-23 and/or IFNα by inhibiting Tyk-2-mediated signal transduction comprising administering to a host in need of such treatment a therapeutically effective amount of at least one of the compounds of the present invention.

The present invention also provides a method for treating proliferative, metabolic, allergic, autoimmune and inflammatory diseases, comprising administering to a host in need of such treatment a therapeutically effective amount of at least one of the compounds of the present invention.

A preferred embodiment is a method for treating inflammatory and autoimmune diseases or diseases. For the purposes of this invention, an inflammatory and autoimmune disease or disorder includes any disease having an inflammatory or autoimmune component.

An alternate preferred embodiment is a method for treating metabolic diseases, including type 2 diabetes and atherosclerosis.

The present invention also provides the use of the compounds of the present invention for the manufacture of a medicament for the treatment of cancers.

The present invention also provides the compounds of the present invention for use in therapy.

These and other features of the invention will be set forth in the expanded form as the disclosure continues.

DETAILED DESCRIPTION OF THE INVENTION

In a first aspect of the present invention, there is provided a compound of formula (I)

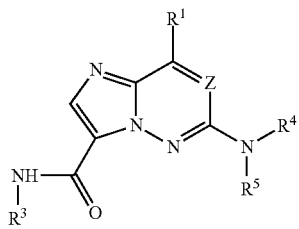

(I)

wherein

Z is —CH— or —N—

$R^1$ is H or —NHR$^2$;

$R^2$ is H, $C_1$-$C_6$ alkyl, $C_3$-$C_8$ cycloalkyl, hydroxy $C_1$-$C_6$ alkyl, alkoxy $C_1$-$C_6$ alkyl, $C_3$-$C_8$ cycloalkyl $C_1$-$C_6$ alkyl-, di ($C_1$-$C_4$) alkyl aminoalkyl-, aryl, heteroaryl, or heterocyclyl $C_1$-$C_6$ alkyl-, said heteroaryl group substituted with 0-2 $R^8$ $R^3$ is H, $C_3$-$C_{10}$-mono or bicyclic cycloalkyl, $C_1$-$C_6$ alkyl, $C_4$-$C_{10}$ mono or bicyclic aryl, or 4- to 10-membered mono or bicyclic heterocyclyl, each heterocyclyl containing 1-3 heteroatoms selected from N, O, and S, any of said groups other than H substituted with 0-4 $R^6$;

$R^4$ is H, $C_1$-$C_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-4 $R^7$;

$R^5$ is independently H or $C_1$-$C_4$ alkyl; or $R^4$ and $R^5$ are taken together with the nitrogen atom to which they are attached to form a 3-10 membered heterocyclyl ring substituted with 0-2 substituents selected from H, $C_1$-$C_4$ alkyl and OH;

$R^6$ is H, halo, CN, OH, $C_1$-$C_4$ alkyl, $(R^5)_n$N, —NR$^5$COR$^5$, $R^5$O, —CON($R^5)_n$, —SO$_n$R$^5$, n is 1 or 2;

$R^7$ is H, halo, CN, CF$_3$, $C_1$-$C_4$ alkyl, $C_1$-$C_4$ alkoxy, —CONH $C_1$-$C_6$ alkyl, —CONH halo $C_1$-$C_6$ alkyl, —CONH halo $C_1$-$C_6$ alkoxy, heteroaryl, alkynyl (—CCR$^5$), alkenyl-CR$^5$=C(R$^5)_n$ or aryl, said aryl and heteroaryl groups substituted with 0-2 $R^8$;

$R^8$ is H, halo, CF$_3$, $C_1$-$C_4$ alkyl or $C_1$-$C_4$ alkoxy;

or a pharmaceutically acceptable salt, tautomer or stereoisomer thereof.

In a second embodiment, there is provided a compound of formula II, wherein

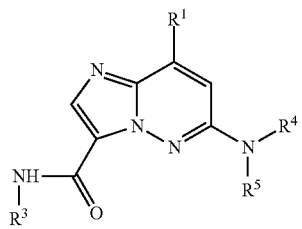

wherein $R^1$ is H or —NHR$^2$;

$R^2$ is H, $C_1$-$C_6$ alkyl, $C_3$-$C_8$ cycloalkyl, hydroxy $C_1$-$C_6$ alkyl, alkoxy $C_1$-$C_6$ alkyl, $C_3$-$C_8$ cycloalkyl $C_1$-$C_6$ alkyl-, di ($C_1$-$C_4$) alkyl aminoalkyl-, aryl, heteroaryl, or heterocyclyl $C_1$-$C_6$ alkyl-, said heteroaryl group substituted with 0-2 $R^8$ $R^3$ is H, $C_3$-$C_{10}$-mono or bicyclic cycloalkyl, $C_1$-$C_6$ alkyl, $C_4$-$C_{10}$ mono or bicyclic aryl, or 4- to 10-membered mono or bicyclic heterocyclyl, each heterocyclyl containing 1-3 heteroatoms selected from N, O, and S, any of said groups other than H substituted with 0-4 $R^6$;

$R^4$ is H, $C_1$-$C_6$ alkyl, 3- to 10-membered mono or bicyclic cycloalkyl, 6- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-4 $R^7$;

$R^5$ is H or $C_1$-$C_4$ alkyl; or $R^4$ and $R^5$ are taken together with the nitrogen atom to which they are attached to form a 3-10 membered heterocyclyl ring substituted with 0-2 substituents selected from H, $C_1$-$C_4$ alkyl and OH;

$R^6$ is H, halo, CN, OH, $C_1$-$C_4$ alkyl, $(R^5)_n$N, —NR$^5$COR$^5$, $R^5$O, —CON($R^5)_n$, —SO$_n$R$^5$, n is 1 or 2;

$R^7$ is H, halo, CN, CF$_3$, $C_1$-$C_4$ alkyl, $C_1$-$C_4$ alkoxy, —CONH $C_1$-$C_6$ alkyl, —CONH halo $C_1$-$C_6$ alkyl, —CONH halo $C_1$-$C_6$ alkoxy, heteroaryl, alkynyl (—CCR$^5$), alkenyl-CR$^5$=C(R$^5)_n$ or aryl, said aryl and heteroaryl groups substituted with 0-2 $R^8$;

$R^8$ is H, halo, CF$_3$, $C_1$-$C_4$ alkyl or $C_1$-$C_4$ alkoxy;

or a pharmaceutically acceptable salt, tautomer or stereoisomer thereof.

In a third embodiment, there is provided a compound of formula II

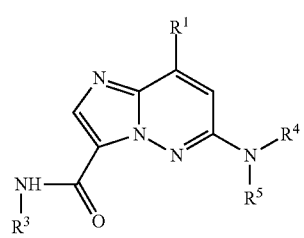

(II)

wherein $R^1$ is —NHR$^2$;

$R^2$ is H, $C_1$-$C_6$ alkyl, $C_3$-$C_8$ cycloalkyl, hydroxy $C_1$-$C_6$ alkyl, alkoxy $C_1$-$C_6$ alkyl, $C_3$-$C_8$ cycloalkyl $C_1$-$C_6$ alkyl-, di ($C_1$-$C_4$) alkyl aminoalkyl-, aryl, heteroaryl, or heterocyclyl $C_1$-$C_6$ alkyl-, said heteroaryl group substituted with 0-2 $R^8$ R³ is H, C₃-C₁₀-mono or bicyclic cycloalkyl, C₁-C₆ alkyl, C₄-C₁₀ mono or bicyclic aryl, or 4- to 10-membered mono or bicyclic heterocyclyl, each heterocyclyl containing 1-3 heteroatoms selected from N, O, and S, any of said groups other than H substituted with 0-4 R⁶;

R⁴ is H, C₁-C₆ alkyl, 3- to 10-membered mono or bicyclic cycloalkyl, 6- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-4 R⁷;

R⁵ is H or C₁-C₄ alkyl; or

R⁴ and R⁵ are taken together with the nitrogen atom to which they are attached to form a 3-10 membered heterocyclyl ring substituted with 0-2 substituents selected from H, C₁-C₄ alkyl and OH;

R⁶ is H, halo, CN, OH, C₁-C₄ alkyl, (R⁵)ₙN, —NR⁵COR⁵, R⁵O, —CON(R⁵)ₙ, —SOₙR⁵, n is 1 or 2;

R⁷ is H, halo, CN, CF₃, C₁-C₄ alkyl, C₁-C₄ alkoxy, —CONH C₁-C₆ alkyl, —CONH halo C₁-C₆ alkyl, —CONH halo C₁-C₆ alkoxy, heteroaryl, alkynyl (—CCR⁵), alkenyl-CR⁵=C(R⁵)ₙ, or aryl, said aryl and heteroaryl groups substituted with 0-2 R⁸;

R⁸ is H, halo, CF₃, C₁-C₄ alkyl or C₁-C₄ alkoxy;

or a pharmaceutically acceptable salt, tautomer or stereoisomer thereof.

In a 4th embodiment, there is provided a compound of formula II,

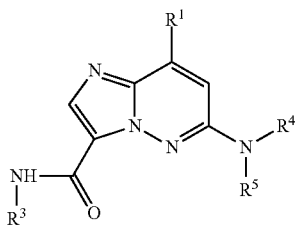

wherein

R¹ is —NHR²;

R² is H, C₁-C₆ alkyl, C₃-C₈ cycloalkyl, hydroxy C₁-C₆ alkyl, alkoxy C₁-C₆ alkyl, C₃-C₈ cycloalkyl C₁-C₆ alkyl-, di(C₁-C₄) alkyl aminoalkyl-, aryl, heteroaryl, or heterocyclyl C₁-C₆ alkyl-, said heteroaryl group substituted with 0-2 R⁸

R³ is H, C₃-C₁₀-mono or bicyclic cycloalkyl, C₁-C₆ alkyl, C₄-C₁₀ mono or bicyclic aryl, or 4- to 10-membered mono or bicyclic heterocyclyl, each heterocyclyl containing 1-3 heteroatoms selected from N, O, and S, any of said groups other than H substituted with 0-4 R⁶;

R⁴ is H, C₁-C₆ alkyl, 3- to 10-membered mono or bicyclic cycloalkyl, 6- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-4 R⁷;

R⁵ is H or C₁-C₄ alkyl;

R⁶ is H, halo, CN, OH, C₁-C₄ alkyl, (R⁵)ₙN, —NR⁵COR⁵, R⁵O, —CON(R⁵)ₙ, —SOₙR⁵, n is 1 or 2;

R⁷ is H, halo, CN, CF₃, C₁-C₄ alkyl, C₁-C₄ alkoxy, —CONH C₁-C₆ alkyl, —CONH halo C₁-C₆ alkyl, —CONH halo C₁-C₆ alkoxy, heteroaryl, alkynyl (—CCR⁵), alkenyl-CR⁵=C(R⁵)ₙ, or aryl, said aryl and heteroaryl groups substituted with 0-2 R⁸;

R⁸ is H, halo, CF₃, C₁-C₄ alkyl or C₁-C₄ alkoxy;

or a pharmaceutically acceptable salt, tautomer or stereoisomer thereof.

In a 5th embodiment, there is provided a compound of formula II

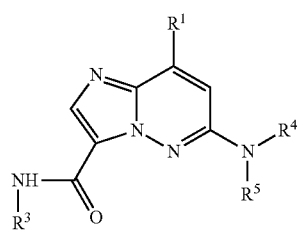

wherein

R¹ is —NHR²;

R² is C₁-C₆ alkyl or C₃-C₈ cycloalkyl;

R³ is H, C₁-C₆ alkyl, hydroxy C₁-C₆ alkyl or C₃-C₈ cycloalkyl;

R⁴ is H, C₁-C₆ alkyl, 3- to 10-membered mono or bicyclic cycloalkyl, 6- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-4 R⁷;

R⁵ is H or C₁-C₄ alkyl;

R⁶ is H, halo, CN, OH, C₁-C₄ alkyl, (R⁵)ₙN, —NR⁵COR⁵, R⁵O, —CON(R⁵)ₙ, —SOₙR⁵, n is 1 or 2;

R⁷ is H, halo, CN, CF₃, C₁-C₄ alkyl, C₁-C₄ alkoxy, —CONH C₁-C₆ alkyl, —CONH halo C₁-C₆ alkyl, —CONH halo C₁-C₆ alkoxy, heteroaryl, alkynyl (—CCR⁵), alkenyl-CR⁵=C(R⁵)ₙ, or aryl, said aryl and heteroaryl groups substituted with 0-2 R⁸;

R⁸ is H, halo, CF₃, C₁-C₄ alkyl or C₁-C₄ alkoxy;

or a pharmaceutically acceptable salt, tautomer or stereoisomer thereof.

In another embodiment, there is provided a compound of formula II,

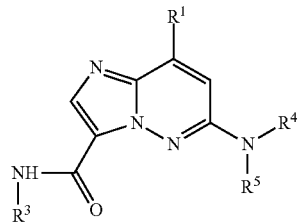

wherein

R¹ is —NHR²;

R² is C₁-C₆ alkyl or C₃-C₈ cycloalkyl;

R³ is H, C₁-C₆ alkyl, hydroxy C₁-C₆ alkyl or C₃-C₈ cycloalkyl;

R⁴ is H, C₁-C₆ alkyl, C₃-C₆ cycloalkyl, phenyl, or pyridyl, any of said groups other than H substituted with 0-4 R⁷;

R⁵ is H or C₁-C₄ alkyl;

$R^6$ is H, halo, CN, OH, $C_1$-$C_4$ alkyl, $(R^5)_nN$, —$NR^5COR^5$, $R^5O$, —$CON(R^5)_n$, —$SO_nR^5$, n is 1 or 2;

$R^7$ is H, halo, CN, $CF_3$, $C_1$-$C_4$ alkyl, $C_1$-$C_4$ alkoxy, —CONH $C_1$-$C_6$ alkyl, —CONH halo $C_1$-$C_6$ alkyl, —CONH halo $C_1$-$C_6$ alkoxy, heteroaryl, alkynyl (—$CCR^5$), alkenyl-$CR^5$=$C(R^5)_n$, or aryl, said aryl and heteroaryl groups substituted with 0-2 $R^8$;

$R^8$ is H, halo, $CF_3$, $C_1$-$C_4$ alkyl or $C_1$-$C_4$ alkoxy;

or a pharmaceutically acceptable salt, tautomer or stereoisomer thereof.

In another preferred embodiment, there is provided a compound of formula II, having the structure:

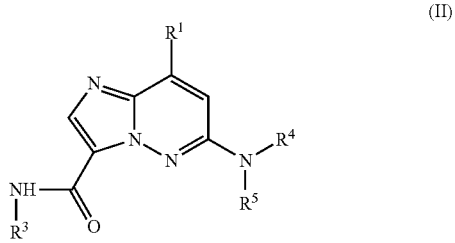

(II)

wherein $R^1$ is —$NHR^2$;

$R^2$ is $CH_3$ or cyclopropyl;

$R^3$ is H, $C_1$-$C_6$ alkyl, hydroxy $C_1$-$C_6$ alkyl or $C_3$-$C_8$ cycloalkyl;

$R^4$ is H, $C_1$-$C_6$ alkyl, $C_3$-$C_6$ cycloalkyl, phenyl, or pyridyl, any of said groups other than H substituted with 0-4 $R^7$;

$R^5$ is H or $C_1$-$C_4$ alkyl;

$R^6$ is H, halo, CN, OH, $C_1$-$C_4$ alkyl, $(R^5)_nN$, —$NR^5COR^5$, $R^5O$, —$CON(R^5)_n$, —$SO_nR^5$, n is 1 or 2;

$R^7$ is H, halo, CN, $CF_3$, $C_1$-$C_4$ alkyl, $C_1$-$C_4$ alkoxy, —CONH $C_1$-$C_6$ alkyl, —CONH halo $C_1$-$C_6$ alkyl, —CONH halo $C_1$-$C_6$ alkoxy, heteroaryl, alkynyl (—$CCR^5$), alkenyl-$CR^5$=$C(R^5)_n$, or aryl, said aryl and heteroaryl groups substituted with 0-2 $R^8$;

$R^8$ is H, halo, $CF_3$, $C_1$-$C_4$ alkyl or $C_1$-$C_4$ alkoxy;

or a pharmaceutically acceptable salt, tautomer or stereoisomer thereof.

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

In another embodiment, there is provided a pharmaceutical composition comprising one or more compounds of formula (I), or stereoisomers, tautomers, pharmaceutically acceptable salts, solvates, or prodrugs thereof, and a pharmaceutically acceptable carrier or diluent.

The present invention is also directed to pharmaceutical compositions useful in treating diseases associated with the modulation of IL-12, IL-23 and/or IFNα by acting on Tyk-2 to cause signal transduction inhibition, comprising compounds of formula I, or pharmaceutically-acceptable salts thereof, and pharmaceutically-acceptable carriers or diluents.

The invention further relates to methods of treating diseases associated with the modulation of IL-12, IL-23, and/or IFNα, comprising administering to a patient in need of such treatment a therapeutically-effective amount of a compound according to formula I.

The present invention also provides processes and intermediates for making the compounds of the present invention.

The present invention also provides a method for treating proliferative, metabolic, allergic, autoimmune and inflammatory diseases (or use of the compounds of the present invention for the manufacture of a medicament for the treatment of these diseases), comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method of treating an inflammatory or autoimmune disease (or use of the compounds of the present invention for the manufacture of a medicament for the treatment of these diseases) comprising administering to a patient in need of such treatment a therapeutically-effective amount of a compound of Formula I.

The present invention also provides a method for treating a disease (or use of the compounds of the present invention for the manufacture of a medicament for the treatment of these diseases), comprising administering to a patient in need of such treatment a therapeutically-effective amount of a compound of Formula I, wherein the disease is rheumatoid arthritis, multiple sclerosis, systemic lupus erythematosus (SLE), lupus nephritis, cutaneous lupus, inflammatory bowel disease, psoriasis, Crohn's Disease, psoriatic arthritis, Sjögren's syndrome, systemic scleroderma, ulcerative colitis, Graves' disease, discoid lupus erythematosus, adult onset Stills, systemic onset juvenile idiopathic arthritis, gout, gouty arthritis, type 1 diabetes, insulin dependent diabetes mellitus, sepsis, septic shock, Shigellosis, pancreatitis (acute or chronic), glomerulonephritis, autoimmune gastritis, diabetes, autoimmune hemolytic anemia, autoimmune neutropenia, thrombocytopenia, atopic dermatitis, myasthenia gravis, pancreatitis (acute or chronic), ankylosing spondylitis, pemphigus vulgaris, Goodpasture's disease, antiphospholipid syndrome, idiopathic thrombocytopenia, ANCA-associated vasculitis, pemphigus, Kawasaki disease, Chronic Inflammatory Demyelinating Polyneuropathy (CIDP), dermatomyositis, polymyositis, uveitis, Guillain-Barre syndrome, autoimmune pulmonary inflammation, autoimmune thyroiditis, autoimmune inflammatory eye disease, and chronic demyelinating polyneuropathy.

The present invention also provides a method of treating an inflammatory or autoimmune disease (or use of the compounds of the present invention for the manufacture of a medicament for the treatment of these diseases), comprising administering to a patient in need of such treatment a therapeutically-effective amount of a compound of Formula I, wherein the disease is selected from systemic lupus erythematosus (SLE), lupus nephritis, cutaneous lupus, Crohn's Disease, ulcerative colitis, type 1 diabetes, psoriasis, rheumatoid arthritis, systemic onset juvenile idiopathic arthritis, ankylosing spondylitis, and multiple sclerosis.

The present invention also provides a method for treating a rheumatoid arthritis (or use of the compounds of the present for the manufacture of a medicament for the treatment of rheumatoid arthritis, comprising administering to a patient in need of such treatment a therapeutically-effective amount of a compound of Formula I.

In addition, the present invention also provides a method of treating a condition (or use of the compounds of the present invention for the manufacture of a medicament for the treatment of these conditions) comprising administering to a patient in need of such treatment a therapeutically-effective amount of a compound of Formula I, wherein the condition is selected from acute myelogenous leukemia, chronic myelogenous leukemia, metastatic melanoma, Kaposi's sarcoma, multiple myeloma, solid tumors, ocular neovasculization, and infantile haemangiomas, B cell lymphoma, systemic lupus erythematosus (SLE), rheumatoid arthritis, psoriatic arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies, pemphigus vulgaris and asthma.

The present invention also provides a method of treating a IL-12, IL-23, and/or IFNα mediated disease (or use of the compounds of the present invention for the manufacture of a medicament for the treatment of said diseases), comprising administering to a patient in need of such treatment a therapeutically-effective amount of a compound of formula I The present invention also provides a method of treating a IL-12, IL-23 and/or IFNα mediated disease (or use of the compounds of the present invention for the manufacture of a medicament for the treatment of these diseases), comprising administering to a patient in need of such treatment a therapeutically-effective amount of a compound of formula I, wherein the IL-12, IL-23 and/or IFNα mediated disease is a disease modulated by IL-12, IL-23 and/or IFNα.

The present invention also provides a method of treating diseases, comprising administering to a patient in need of such treatment a therapeutically-effective amount of a compound of formula I in combination with other therapeutic agents.

The present invention also provides the compounds of the present invention use in therapy.

In another embodiment, compounds of formula I are selected from exemplified compounds or combinations of exemplified compounds or other embodiments herein.

In another embodiment are compounds having an $IC_{50}$<1000 nM in at least one of the assays described below.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —CONH$_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound."

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

One skilled in the field will understand that, when the designation "$CO_2$" is used herein, this is intended to refer to the group

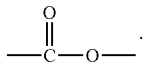

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl. The term "heteroarylalkyl" refers to a substituted alkyl group as defined above where at least one of the substituents is a heteroaryl.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—$C_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, $S(O)_2$H, or $S(O)$H group.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3, 4, 5, 6, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Accordingly, in compounds of formula I, the term "cycloalkyl" includes cyclopropyl, cyclobutyl, cyclopentyl, cyclohexyl, cycloheptyl, bicyclooctyl, etc., as well as the following ring systems:

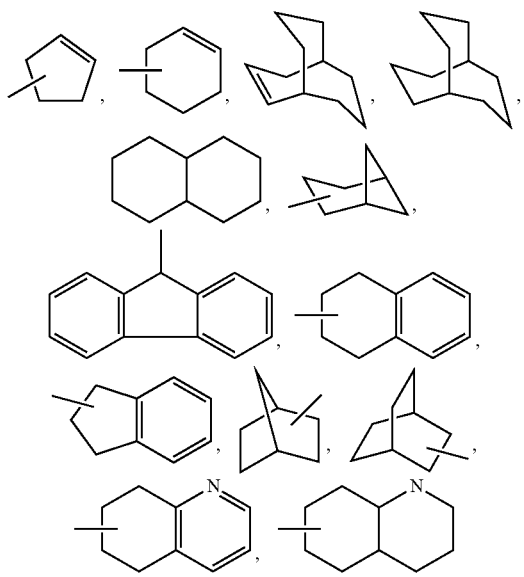

and the like, which optionally may be substituted at any available atoms of the ring(s).

Preferred cycloalkyl groups include cyclopropyl, cyclopentyl, cyclohexyl, and

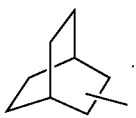

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

Thus, examples of aryl groups include:

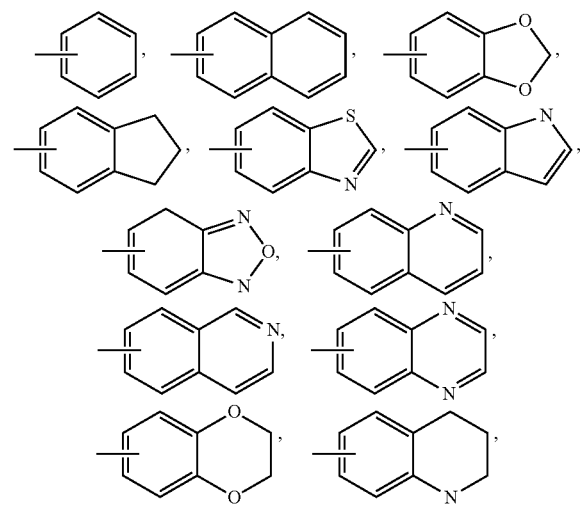

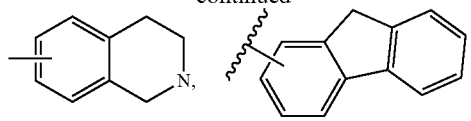

(fluorenyl) and the like, which optionally may be substituted at any available carbon or nitrogen atom. A preferred aryl group is optionally-substituted phenyl.

The terms "heterocycle", "heterocycloalkyl", "heterocyclo", "heterocyclic", or "heterocyclyl" may be used interchangeably and refer to substituted and unsubstituted 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or fully unsaturated. The heterocyclo group may be attached at any available nitrogen or carbon atom. As used herein the terms "heterocycle", "heterocycloalkyl", "heterocyclo", "heterocyclic", and "heterocyclyl" include "heteroaryl" groups, as defined below.

In addition to the heteroaryl groups described below, exemplary monocyclic heterocyclyl groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include and

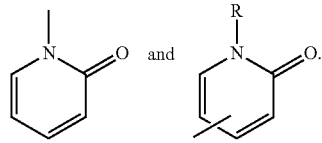

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

In compounds of formula I, preferred heteroaryl groups include

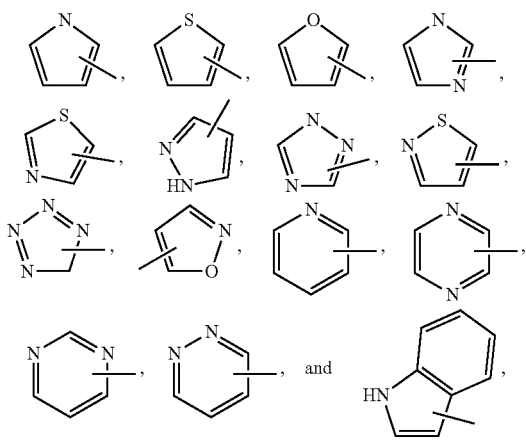

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0 to 2, substituents selected from those recited above for the aryl, cycloalkyl, heterocyclo and/or heteroaryl groups, as appropriate.

The term "carbocyclyl" or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl. The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula I may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s)" may include zwitterions (inner salts), e.g., when a compound of formula I, contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 18th Edition, Mack Publishing Company, Easton, Pa. (1990), the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula I, and/or a salt and/or solvate thereof. Any compound that will be converted in vivo to provide the bioactive agent (i.e., the compound for formula I) is a prodrug within the scope and spirit of the invention. For example, compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$alkanoyloxy-$C_{1-6}$alkyl, e.g, acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well-known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and c) Bundgaard, H., *Adv. Drug Deliv. Rev.*, 8:1-38 (1992), each of which is incorporated herein by reference.

Compounds of the formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers.

It should further be understood that solvates (e.g, hydrates) of the compounds of Formula I are also with the scope of the present invention. Methods of solvation are generally known in the art.

Utility

The compounds of the invention modulate IL-23-stimulated and IFNα-stimulated cellular functions, including gene transcription. Other types of cellular functions that may be modulated by the compounds of the instant invention include, but are not limited to, IL-12-stimulated responses.

Accordingly, compounds of formula I have utility in treating conditions associated with the modulation of the function of IL-23 or IFNα, and particularly the selective inhibition of function of IL-23, IL-12 and/or IFNα, by acting on Tyk2 to mediate signal transduction. Such conditions include IL-23-, IL-12-, or IFNα-associated diseases in which pathogenic mechanisms are mediated by these cytokines.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as modulators of IL-23-, IL-12 and IFNα-stimulated cellular responses, compounds of Formula I are useful in treating IL-23-, IL-12- or IFNα-associated diseases including, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosis, cutaneous lupus, lupus nephritis, discoid lupus erythematosus, psoriasis; auto-inflammatory diseases including CAPS, TRAPS, FMF, adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, cutaneous lupus, lupus nephritis, discoid lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's disease, ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

When the terms "IL-23-, IL-12- and/or IFNα-associated condition" or "IL-23-, IL-12- and/or IFNα-associated disease or disorder" are used herein, each is intended to encompass all of the conditions identified above as if repeated at length, as well as any other condition that is affected by IL-23, IL-12 and/or IFNα.

The present invention thus provides methods for treating such conditions, comprising administering to a subject in need thereof a therapeutically-effective amount of at least one compound of Formula I or a salt thereof. "Therapeutically effective amount" is intended to include an amount of a compound of the present invention that is effective when administered alone or in combination to inhibit IL-23, IL-12 and/or IFNα function and/or treat diseases.

The methods of treating IL-23-, IL-12 and/or IFNα-associated conditions may comprise administering compounds of Formula I alone or in combination with each other and/or other suitable therapeutic agents useful in treating such conditions. Accordingly, "therapeutically effective amount" is also intended to include an amount of the combination of compounds claimed that is effective to inhibit IL-23, IL-12 and/or IFN function and/or treat diseases associated with IL-23, IL-12 and/or IFNα.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating IL-23-, IL-12- or IFNα-associated conditions by inhibiting Tyk2-mediated signal transduction, including IL-23-, IL-12- and/or IFNα-mediated diseases, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula I and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Remington's Pharmaceutical Sciences, 17th Edition (1985), which is incorporated herein by reference in its entirety.

The compounds of Formula I may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5 250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species that are affected by modulation of IL-23, IL-12 and/or IFNα-mediated functions.

Biological Assays

Probe Displacement Assay

The probe displacement assay is conducted as follows: In a 385 well plate, test compounds along with recombinantly expressed His-tagged protein corresponding to amino acids 575-869 of human Tyk2 (sequence shown below) at 2.5 nM, 40 nM ((R)—N-(1-(3-(8-methyl-5-(methylamino)-8H-imidazo[4,5-d]thiazolo[5,4-b]pyridin-2-yl)phenyl)ethyl)-2-([$^3$H]methylsulfonyl)benzamide) (preparation described below) and 80 μg/mL Copper His-Tag scintillation proximity assay beads (Perkin Elmer, Catalog #RPNQ0095) in 50 mM HEPES, pH 7.5, containing 100 μg/mL bovine serum albumin and 5% DMSO were incubated for 30 minutes at room temperature. The amount of radiolabeled probe (preparation described below) bound to Tyk2 was then quantified by scintillation counting, and the inhibition by the test compound calculated by comparison to wells either with no inhibitor (0% inhibition) or without Tyk2 (100% inhibition). The IC50 value is defined as the concentration of test compound required to inhibit radiolabeled probe binding by 50%.

Protein Sequence of Recombinant Hig-Tagged Tyk2 (575-869):

```
                                        (SEQ ID NO: 1)
MGSSHHHHHH  SSGETVRFQG  HMNLSQLSFH  RVDQKEITQL

SHLGQGTRTN  VYEGRLRVEG  SGDPEEGKMDDEDPLVPGRD

RGQELRVVLK  VLDPSHHDIA  LAFYETASLM  SQVSHTHLAF

VHGVCVRGPE  NIMVTEYVEHGPLDVWLRRE  RGHVPMAWKM

VVAQQLASAL  SYLENKNLVH  GNVCGRNILL  ARLGLAEGTS

PFIKLSDPGVGLGALSREER  VERIPWLAPE  CLPGGANSLS

TAMDKWGFGA  TLLEICFDGE  APLQSRSPSE

KEHFYQRQHRLPEPSCPQLA  TLTSQCLTYE  PTQRPSFRTI

LRDLTRL..
```

The preparation of radiolabeled probe, (R)—N-(1-(3-(8-methyl-5-(methylamino)-8H-imidazo[4,5-d]thiazolo[5,4-b]pyridin-2-yl)phenyl)ethyl)-2-([$^3$H]methylsulfonyl)benzamide, was performed as described below:

2-([$^3$H]methylsulfonyl)benzoic acid

2-Mercaptobenzoic acid (2.3 mg, 0.015 mmol) and cesium carbonate (2 mg, 0.006 mmol) were added to a 5 mL round-bottomed flask. The flask was attached to a ported glass vacuum line and anhydrous DMF (0.5 mL) was introduced with magnetic stirring. An ampoule of tritiated methyl iodide (200 mCi, Perkin-Elmer lot 3643419) was added to the reaction flask and stirring was maintained at rt for 3 h. In-process HPLC analysis with radiometric detection indicated 80% conversion to the desired product by comparison with authentic standard. Without purification, the crude product was reacted with mCPBA (10 mg, 0.058 mmol) pre-dissolved in CH$_2$Cl$_2$ (1 mL) at room temperature with stirring. The reaction was stirred for 7 h and additional mCPBA (10 mg, 0.058 mmol) was added. The reaction was stirred for approximately 24 h and HPLC analysis indicated 35-40% conversion to the desired sulfonate product. The crude product was purified by semi-preparative HPLC (Luna 5 um C18 (10×250 cm); A: MeOH/H$_2$O=15/85 (0.1% TFA); B: MeOH; 270 nm; 0-8 min 0% B 1 ml/min; 8-10 min 0% B 1-3 ml/min; 10-55 min 0% B 3 ml/min; 55-65 min 0-10% B 3 ml/min; 65-75 min 10-50% B 3 ml/min; 75-80 min 50-100% B 3 ml/min) to give 81 mCi (40% radiochemical yield) of 2-([$^3$H]methylsulfonyl)benzoic acid product identified by its HPLC co-elution with an authentic standard. The radiochemical purity was measured by HPLC to be 99% (Luna 5u C18 (4.6×150 cm); A: H$_2$O (0.1% TFA); B: MeOH; 1.2 ml/min; 270 nm; 0-10 min 20% B; 10-15 min 20-100% B; 15-25 min 100% B. The product was dissolved in anhydrous acetonitrile to give a final solution activity of 5.8 mCi/mL. (R)—N-(1-(3-(8-methyl-5-(methylamino)-8H-imidazo[4,5-d]thiazolo[5,4-b]pyridin-2-yl)phenyl)ethyl)-2-([$^3$H]methylsulfonyl)benzamide: A solution of 2-([$^3$H]methylsulfonyl)benzoic acid (23.2 mCi) in acetonitrile was added to a 5 mL round-bottomed flask which was then attached to a vacuum line and carefully evaporated to dryness. (R)-2-(3-(1-aminoethyl)phenyl)-N, 8-dimethyl-8H-imidazo[4,5-d]thiazolo[5,4-b]pyridin-5-amine (prepared as described in WO 2004/106293 and Dyckman et al., *Bioorganic and Medicinal Chemistry Letters*, 383-386 (2011)) (1.1 mg, 0.0033 mmol) and PyBOP (2 mg, 0.0053 mmol) dissolved in anhydrous DMF (1.5 mL) were added to the flask followed by N,N-diisopropylethylamine (0.010 mL). The resulting clear solution was stirred at room temperature for 18 h. HPLC analysis (Luna 5u C18 (4.6×150 cm); A: H$_2$O (0.1% TFA); B: MeOH; 1.2 ml/min; 335 nm; 0-20 min 50% B; 20-25 min 50-100% B; 25-30 min 100% B) indicated approximately a 20% conversion to the desired product by retention time comparison to a sample of non-radiolabeled (R)—N-(1-(3-(8-methyl-5-(methylamino)-8H-imidazo[4,5-d]thiazolo[5,4-b]pyridin-2-yl)phenyl)ethyl)-2-(methylsulfonyl)benzamide. The crude reaction mixture was purified by semi-preparative HPLC (Luna 5u C18 (10×250 cm); A: MeOH/H$_2$O=50/50 (0.1% TFA); B: MeOH; 335 nm; 0-40 min 0% B 3 ml/min; 40-45 min 0-100% B 3 ml/min). The purification routine was performed a second time to yield a total of 1.7 mCi (7% radiochemical yield) of the desired product in 99.9% radiochemical purity. Mass spectral analysis of the tritiated product (m/z M+H 527.33) was used to establish the specific activity at 80.6 Ci/mmol.

| Probe Displacement Data | |
|---|---|
| Example | Probe Displacement (EC50, uM) |
| 1 | 7.05E-03 |
| 2 | 3.24E-03 |
| 3 | 0.06 |
| 4 | 6.85E-03 |
| 5 | 7.29E-03 |
| 6 | 4.21E-03 |
| 7 | 0.25 |
| 8 | 3.61E-03 |
| 9 | 5.91E-03 |
| 10 | 7.57E-03 |
| 11 | 0.09 |
| 12 | 2.22E-03 |

Probe Displacement Data

| Example | Probe Displacement (EC50, uM) |
|---|---|
| 13 | 2.97E−03 |
| 14 | 7.03E−03 |
| 15 | 0.02 |
| 16 | 7.04E−03 |
| 17 | 0.02 |
| 18 | 3.72E−03 |
| 19 | 5.86E−03 |
| 20 | 3.97E−03 |
| 21 | 0.03 |
| 22 | 5.46E−03 |
| 23 | 0.04 |
| 24 | 7.25E−03 |
| 25 | 6.05E−03 |
| 26 | 2.93E−03 |
| 27 | 2.70E−03 |
| 28 | 0.06 |
| 29 | 0.04 |
| 30 | 0.02 |
| 31 | 0.13 |
| 32 | 0.05 |
| 33 | 0.19 |
| 34 | 0.48 |
| 35 | 0.16 |
| 36 | 0.35 |
| 37 | 0.02 |
| 38 | 0.02 |
| 44 | 0.06 |
| 45 | 0.03 |
| 46 | 0.02 |
| 47 | 0.04 |
| 48 | 0.11 |
| 49 | 0.50 |
| 50 | 0.07 |
| 51 | 0.07 |
| 52 | 0.07 |
| 53 | 0.20 |
| 54 | 0.03 |
| 55 | 0.08 |
| 56 | 0.07 |
| 58 | 0.08 |
| 59 | 0.16 |
| 60 | 0.05 |
| 61 | 0.05 |
| 62 | 0.30 |
| 63 | 0.28 |
| 64 | 0.07 |
| 65 | 0.02 |
| 66 | 3.58E−03 |
| 67 | 0.01 |
| 68 | 2.26E−03 |
| 69 | 5.44E−03 |
| 70 | 0.08 |
| 71 | 0.14 |
| 73 | 7.75E−03 |
| 74 | 0.01 |
| 75 | 2.09E−03 |
| 76 | 0.05 |
| 77 | 4.02E−03 |
| 78 | 8.17E−03 |
| 79 | 6.95E−03 |
| 80 | 4.83E−03 |
| 81 | 7.26E−03 |
| 82 | 0.01 |
| 83 | 5.76E−03 |
| 84 | 6.13E−03 |
| 85 | 9.31E−03 |
| 86 | 0.02 |
| 87 | 4.31E−03 |
| 88 | 8.34E−03 |
| 89 | 0.01 |
| 90 | 3.90E−03 |
| 91 | 0.20 |
| 92 | 0.03 |
| 93 | 0.01 |
| 94 | 1.37E−03 |
| 95 | 0.02 |
| 96 | 7.18E−03 |
| 97 | 0.03 |
| 98 | 0.03 |
| 99 | 0.57 |
| 100 | 0.14 |
| 101 | 0.27 |
| 102 | 6.10E−03 |
| 103 | 0.16 |
| 105 | 0.01 |
| 106 | 0.08 |
| 107 | 9.39E−03 |
| 108 | 7.59E−03 |
| 108 | 2.91E−03 |
| 110 | 7.52E−03 |
| 111 | 3.84E−03 |
| 112 | 7.70E−03 |
| 113 | 7.62E−03 |
| 114 | 7.93E−03 |
| 115 | 1.50E−02 |
| 116 | 6.55E−02 |
| 117 | 1.26E−02 |
| 118 | 2.48E−02 |
| 119 | 0.22 |

Kit225 T Cell Assay

Kit225 T cells with a stably-integrated STAT-dependent luciferase reporter were plated in RPMI (GIBCO) containing 10% heat-inactivated FBS (GIBCO) and 100 U/mL PenStrep (GIBCO). The cells were then stimulated with either 20 ng/mL human recombinant IL-23 or 200 U/mL human recombinant IFNα (PBL InterferonSource) for 5-6 hours. Luciferase expression was measured using the STEADY-GLO Luciferase Assay System (PROMEGA) according to the manufacturer's instructions. Inhibition data were calculated by comparison to no inhibitor control wells for 0% inhibition and non-stimulated control wells for 100% inhibition. Dose response curves were generated to determine the concentration required to inhibit 50% of cellular response (IC50) as derived by non-linear regression analysis.

Kit225 T Cell Inhibition Data

| Ex # | IL-23 Kit225 Reporter, (IC50, uM) | IFNa Kit225 Reporter, (IC50, uM) |
|---|---|---|
| 1 | 0.10 | 0.05 |
| 2 | 0.03 | 0.03 |
| 3 | 2.82 | 1.92 |
| 4 | 0.81 | 0.32 |
| 5 | 0.50 | 0.50 |
| 6 | 0.12 | 0.09 |
| 7 |  | 3.30 |
| 8 | 0.03 | 0.03 |
| 9 | 0.25 | 0.17 |
| 10 | 0.16 | 0.08 |
| 11 | 2.90 | 2.27 |
| 12 | 0.30 | 0.11 |
| 13 | 0.05 | 0.03 |
| 14 | 0.37 | 0.26 |
| 15 | 0.56 | 0.40 |

Kit225 T Cell Inhibition Data

| Ex # | IL-23 Kit225 Reporter, (IC50, uM) | IFNa Kit225 Reporter, (IC50, uM) |
| --- | --- | --- |
| 16 | 0.24 | 0.09 |
| 17 | 0.55 | 0.48 |
| 18 | 0.04 | 0.01 |
| 19 | 0.27 | 0.17 |
| 20 | 0.06 | 0.05 |
| 21 | 0.39 | 0.21 |
| 22 | 0.25 | 0.18 |
| 23 | 0.42 | 0.66 |
| 24 | 0.04 | 0.05 |
| 25 | 0.05 | 0.09 |
| 26 | 0.09 | 0.06 |
| 27 | 0.04 | 0.01 |
| 28 | 0.33 | 0.45 |
| 29 | 0.27 | 0.41 |
| 30 | 0.35 | 0.21 |
| 31 | 0.58 | 2.58 |
| 32 | 0.54 | 0.31 |
| 33 | 12.50 | 12.50 |
| 34 | 8.24 | 12.60 |
| 35 | 8.07 | 8.48 |
| 36 | 3.33 | 12.50 |
| 37 | 1.42 | 1.75 |
| 38 | 0.79 | 0.58 |
| 44 | 1.46 | 1.39 |
| 45 | 1.10 | 1.49 |
| 46 | 0.72 | 1.45 |
| 47 | 1.12 | 1.13 |
| 48 | 6.18 | 4.10 |
| 49 | 7.29 | 4.75 |
| 50 | 2.32 | 1.28 |
| 51 | 3.74 | 2.90 |
| 52 | 7.04 | 12.76 |
| 53 | 9.72 | 12.40 |
| 54 | 1.25 | 1.17 |
| 55 | 2.38 | 3.62 |
| 56 | 2.12 | 1.79 |
| 58 | 1.55 | 2.96 |
| 59 | 9.48 | 12.50 |
| 60 | 4.94 | 3.68 |
| 61 | 2.63 | 1.94 |
| 62 | 13.19 | 11.02 |
| 63 | 12.50 | 12.50 |
| 64 | 12.50 | 12.50 |
| 65 | 0.58 | 0.59 |
| 66 | 0.33 | 0.20 |
| 67 | 0.70 | 0.73 |
| 68 | 0.95 | 0.86 |
| 69 | 0.42 | 0.15 |
| 70 | 11.23 | 12.50 |
| 71 | 2.97 | 12.50 |
| 73 | 0.28 | 0.14 |
| 74 | 0.30 | 0.20 |
| 75 | 0.10 | 0.05 |
| 76 | 3.55 | 2.79 |
| 77 | 0.03 | 0.01 |
| 78 | 0.18 | 0.07 |
| 79 | 0.07 | 0.05 |
| 80 | 0.15 | 0.12 |
| 81 | 0.27 | 0.23 |
| 82 | 0.18 | 0.09 |
| 83 | 0.17 | 0.06 |
| 84 | 0.02 | 0.01 |
| 85 | 0.04 | 0.03 |
| 86 | 0.29 | 0.30 |
| 87 | 0.09 | 0.06 |
| 88 | 0.01 | 0.02 |
| 89 | 0.39 | 0.44 |
| 90 | 0.70 | 0.14 |
| 91 | 8.69 | 8.81 |
| 92 | 0.40 | 0.21 |
| 93 | 1.10 | 0.41 |
| 94 | 0.02 | 0.03 |
| 95 | 0.37 | 0.27 |
| 96 | 0.51 | 0.60 |
| 97 | 0.42 | 0.65 |
| 98 | 0.50 | 0.53 |
| 100 | 12.50 | 12.50 |
| 101 | 7.19 | 5.79 |
| 102 | 0.38 | 0.65 |
| 103 | 0.47 | 0.36 |
| 104 | 0.18 | 0.18 |
| 106 | 0.44 | 1.26 |
| 107 | 0.47 | 1.42 |
| 108 | 0.61 | 0.28 |
| 108 | 0.12 | 0.09 |
| 110 | 0.16 | 0.12 |
| 111 | 0.16 | 0.24 |
| 112 | 0.45 | 0.30 |
| 113 | 0.75 | 0.78 |
| 114 | 0.11 | 0.10 |
| 115 | 0.34 | 0.48 |
| 116 | 1.1 | 1.2 |
| 117 | 0.41 | 0.51 |
| 118 | 0.32 | 0.41 |
| 119 | 3.2 | 3.4 |

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the preparations and examples section set out hereinafter. Several of the compounds described were chiral, some were prepared as racemic mixtures, while others were prepared as a single enantiomer. In each case the preparation of the homochiral examples, or the preparation of the opposite enantiomer, may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

Scheme 1

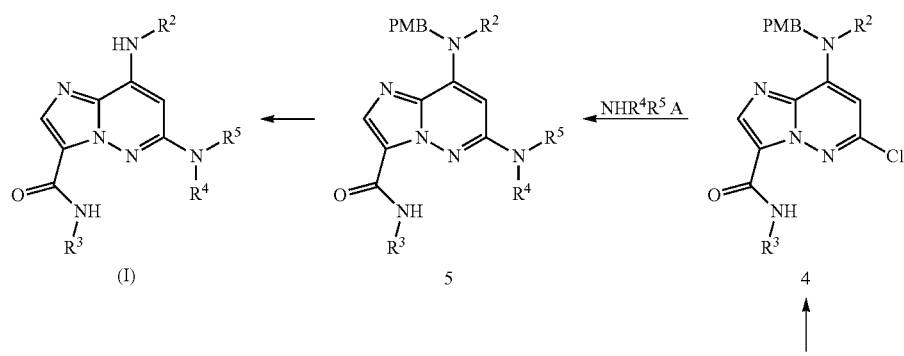

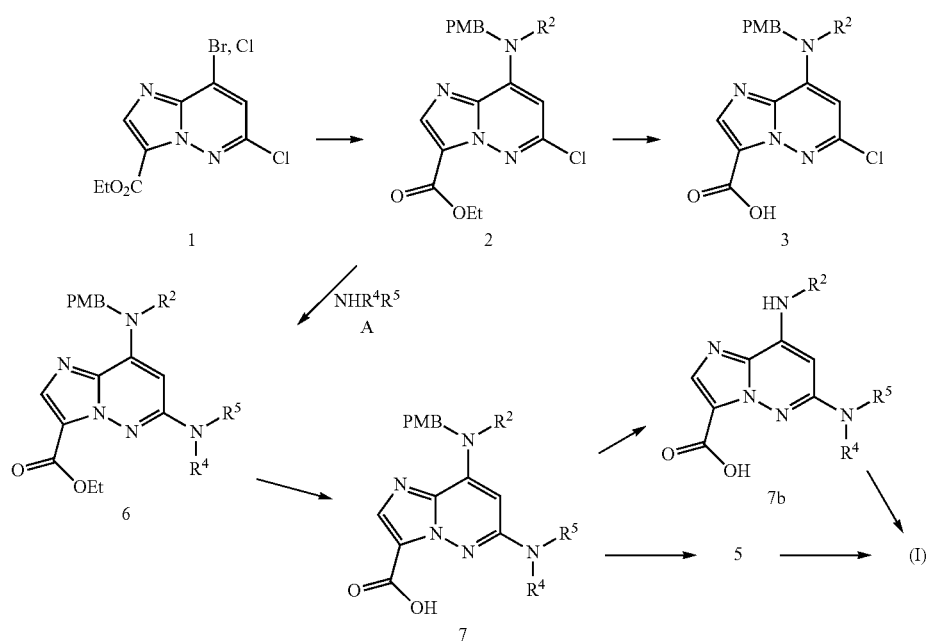

The compounds of Formula (I) can be prepared according to Scheme 1. Treatment of imidazopyridazine derivative (1) (WO 2009/100375) with p-methoxybenzyl protected amine (R¹NHPMB) provides ester 2. The latter is hydrolyzed to acid 3, which is subsequently converted to amide 4 by standard coupling reaction. Buchwald reaction of 4 with A, promoted by catalysts such as tris(dibenzylideneacetone)dipalladium(0)/XantPhos and palladium(II) acetate/BrettPhos, affords 5. Removal of the PMB protection group from 5 (HCl or other conditions known to effect deprotection of PMB-protected amines) leads to the formation of compound (I). Alternatively, Buchwald reaction can be performed with 2 and A to give rise to intermediate 6, which is then transformed to compound (I) by hydrolysis, to give acid 7, followed by amide formation and deprotection. In another mode, the PMB group of 7 may be removed (as with 5) to give an amino acid 7b, which may then be treated with amine $R_2NH_2$ under amide bond coupling conditions to give (I).

Scheme 2

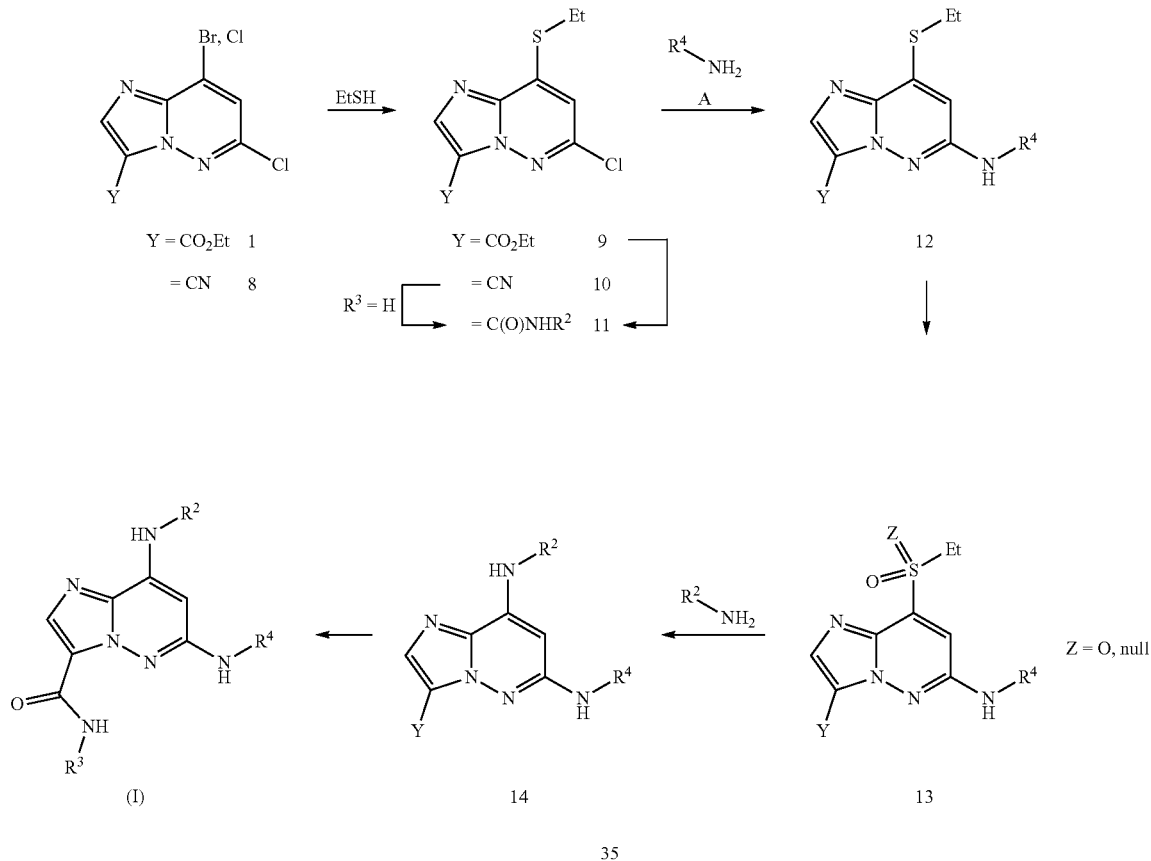

Compounds with formula (I) can also be prepared in a manner whereby the C8 group is introduced at, or near, the end of the synthesis (Scheme 2). This is accomplished via the addition of ethanethiol to 1 (or the related cyano compound 8 WO2010/042699) in the presence of an amine base in a polar aprotic solvent such as tetrahydrofuran. At this stage the compound can either be carried on further (to 12) or converted to the C3 amide, either by hydrolysis (from 10) using an alkoxide base such as potassium or lithium hydroxide along with aqueous hydrogen peroxide, or via saponification (from 9) to the corresponding acid using an aqueous alkoxide base and subsequent conversion to the amide. It is also possible to perform these conversions at the C3 position on intermediate 12 or on the penultimate compound 14. Compound 12 is prepared via the coupling with amine A as previously described in Scheme 1. Oxidation of 12 to 13 can be performed using 3-chloroperbenzoic acid, and while a mixture of the sulfoxide (Z=null) and sulfone (Z=O) may result, both versions of 13 are viable substrates for the subsequent displacement. Addition of a basic or aliphatic amine can be accomplished simply by combining them with 13, either neat or with a polar aprotic solvent, at an elevated temperature. Non-basic amines such as anilines must be combined with a strong non-nucleophilic base such as sodium hydride in an appropriate anhydrous solvent, note that in this case the displacement works only if the C3 substituent is in the form of an amide. Conversion of Y to the amide to provide (I) can be accomplished as described above.

Scheme 3

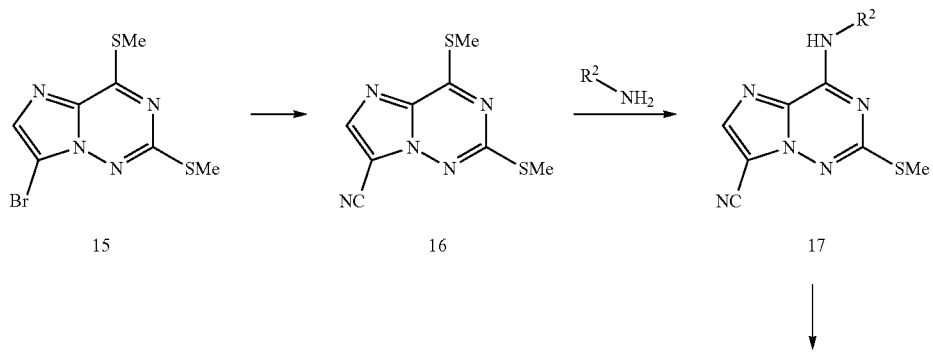

-continued

[Structure 19: imidazo-triazine with HN-R2, NH-R4, and C(=O)NH2 substituent]

19

[Structure 18: imidazo-triazine with HN-R2, S(=O)Me (sulfoxide), and NC substituent]

18

Reagent: R4-NH2 (A)

Scheme 3 illustrates the preparation of imidatriazines (19). A Negishi coupling of 15 (WO 2008/116064) with zinc cyanide in the presence of zinc powder and a palladium source (such as bis(tri-t-butylphosphine)palladium (0)) can be used to provide 16. Addition of an amine to 16 results in the regioselective displacement of one of the C8 sulfide to provide 17. Oxidation of the remaining sulfide can be accomplished using 3-chloroperbenzoic acid to provide the sulfoxide (18), which is then combined with aniline (A) in the presence of wet 1-methyl-2-pyrrolidinone and sodium hydride to provide the target ligand 19.

Preparations

The preparations set out below are for the synthesis of reagents that were not obtained from commercial sources and were employed for the preparation of compounds of formula I of the invention. All chiral compounds in the tables and schemes are racemic unless specified otherwise.

Reverse-phase preparative high performance liquid chromatography ("HPLC") was performed with Shimadzu 8A liquid chromatographs using YMC S5 ODS columns (20× 100, 20×250, or 30×250 millimeter ("mm")). Gradient elution was performed with methanol ("MeOH")/water mixtures in the presence of 0.1% trifluoroacetic acid ("TFA").

Analytical HPLC Method Employed in Characterization of Examples

Analytical HPLC was performed on Shimadzu LC10AS liquid chromatographs using the following methods:

Method A (Used in all Cases, Unless Otherwise Indicated):
  Linear gradient of 0 to 100% solvent B over 4 minutes ("min"), with 1 minute ("min") hold at 100% B.
  Ultraviolet ("UV") visualization at 220 nanometers ("nm")
  Column: YMC S5 ODS Ballistic 4.6×50 mm
  Flow rate: 4 milliliters ("mL")/min
  Solvent A: 0.2% phosphoric acid, 90% water, 10% methanol
  Solvent B: 0.2% phosphoric acid, 90% methanol, 10% water Method B:
  Column: Phenomenex Luna C18(2), 4.6×50 mm×5 um
  Mobile Phase: (A) 10:90 methanol:water; (B) 90:10 methanol:water
  Buffer: 0.1% TFA
  Gradient Range: 0-100% B
  Gradient Time: 4 min
  Flow Rate: 4 mL/min
  Analysis Time: 5 min
Detection:
  Detector 1: UV at 220 nm
  Detector 2: MS (ESI+)
  Detector 3: ELSD Method C:
  Column: Waters SunFire C18, 4.6×50 mm×5 um
  Mobile Phase: (A) 10:90 methanol:water; (B) 90:10 methanol:water
  Buffer: 0.1% TFA
  Gradient Range: 0-100% B
  Gradient Time: 4 min
  Flow Rate: 4 mL/min
  Analysis Time: 5 min
Detection:
  Detector 1: UV at 220 nm
  Detector 2: MS (ESI+)
  Detector 3: ELSD Method D:
  Column: Phenomenex Luna C18(2), 4.6×50 mm×5 um
  Mobile Phase: (A) 10:90 methanol:water; (B) 90:10 methanol:water
  Buffer: 0.1% TFA
  Gradient Range: 0-100% B
  Gradient Time: 4 min
  Flow Rate: 4 mL/min
  Analysis Time: 5 min
Detection:
  Detector 1: UV at 220 nm
  Detector 2: MS (ESI+)
  Detector 3: ELSD Method E:
  Column: Waters Acquity UPLC BEH C18, 2.1×50 mm, 1.7 m particles
  Mobile Phase: (A) 5:95 acetonitrile:water; (B) 95:5 acetonitrile:water
  Buffer: 10 mM ammonium acetate
  Gradient Range: 0-100% B
  Gradient Time: 3 min
  Flow Rate: 1.11 mL/min
  Analysis Time: 4 min
Detection:
  Detector 1: UV at 220 nm
  Detector 2: MS (ESI+)
  Detector 3: ELSD Method F:
  Column: Waters Sunfire C18 (3.0×150 mm), 3.5 µm
  Mobile Phase: (A) 5:95 acetonitrile:water; (B) 95:5 acetonitrile:water
  Buffer: 0.1% TFA
  Gradient Range: 0-100% B
  Gradient Time: 12 min
  Flow Rate: 1 mL/min
  Analysis Time: 15 min
Detection:
  Detector 1: UV at 220 nm
  Detector 2: UV at 254 nm Method G:
Column: Waters Acquity UPLC BEH C18, 2.1×50 mm, 1.7 µm particles
Mobile Phase: (A) 5:95 acetonitrile:water; (B) 95:5 acetonitrile:water
Buffer: 0.05% TFA
Gradient Range: 0-100% B
Gradient Time: 3 min
Flow Rate: 1.11 mL/min
Analysis Time: 4 min
  Detection:
Detector 1: UV at 220 nm
Detector 2: MS (ESI+)
Detector 3: ELSD
Method H:
Column: (LCMS) Ascentis Express C18, 4.6×50 mm, 2.7 µm particles
Mobile Phase: (A) 5:95 acetonitrile:water; (B) 95:5 acetonitrile:water
Buffer: 10 mM ammonium acetate
Gradient Range: 0-100% B
Gradient Time: 4 min
Flow Rate: 4 mL/min
Analysis Time: 5 min
  Detection:
Detector 1: UV at 220 nm
Detector 2: MS (ESI+)
Method I:
Column: Waters Xbridge C18, 4.6×50 mm, 5 µm particles
Mobile Phase: (A) 5:95 acetonitrile:water; (B) 95:5 acetonitrile:water
Buffer: 10 mM NH$_4$OAc
Gradient Range: 0-100% B
Gradient Time: 4 min
Flow Rate: 4 mL/min
Analysis Time: 5 min
  Detection:
Detector 1: UV at 220 nm
Detector 2: MS (ESI+)
Method J:
Column: (LCMS) BEH C18, 2.1×50 mm, 1.7 m particles
Mobile Phase: (A) water; (B) acetonitrile
Buffer: 0.05% TFA
  2%-98% B (0 to 1 min) 98% B (to 1.5 min) 98%-2% B (to 1.6
Gradient Range: min)
Gradient Time: 1.6 min
Flow Rate: 0.8 mL/min
Analysis Time: 2.2 min
Detection:
Detector 1: UV at 254 nm
Detector 2: MS (ESI+)
Method K:
Column: (LCMS) BEH C18, 3.0×50 mm, 1.7 m particles
Mobile Phase: (A) 5:95 acetonitrile:water; (B) 95:5 acetonitrile:water
Buffer: 10 mM ammonium acetate
Gradient Range: 0-100% B
Gradient Time: 1.8 min
Flow Rate: 1.2 mL/min
Analysis Time: 4 min
  Detection:
Detector 1: UV at 220 nm
Detector 2: MS (ESI+)

Method L:
Column: (LCMS) Sunfire C18 2.1×30 mm, 2.5 m particles
Mobile Phase: (A) 10:90 methanol:water; (B) 90:10 methanol:water
Buffer: 0.1% TFA
Gradient Range: 0-100% B
Gradient Time: 2 min
Flow Rate: 1 mL/min
Analysis Time: 3 min
  Detection:
Detector 1: UV at 220 nm
Detector 2: MS (ESI+)
Method M:
Column: (LCMS) Sunfire C18 2.1×30 mm, 3.5 m particles
Mobile Phase: (A) 10:90 methanol:water; (B) 90:10 methanol:water
Buffer: 0.1% TFA
Gradient Range: 0-100% B
Gradient Time: 4 min
Flow Rate: 1 mL/min
Analysis Time: 5 min
Detection:
Detector 1: UV at 220 nm
Detector 2: MS (ESI+)
Method N:
Column: YMC ProC18 ODS, 4.6×50 mm
Mobile Phase: (A) 10:90 MeOH:water; (B) 90:10 MeOH:water
Buffer: 0.2% H3PO4
Gradient Range: 0-100% B
Gradient Time: 4 min
Flow Rate: 4 mL/min
Analysis Time: 4 min
Detection: 220 nm
Method O:
Column: (LCMS) Zorbax SB C18 (30×2.1 mm; 3.5 uM)
Mobile Phase: (A) buffer+acetonitrile (98:2); (B) buffer+acetonitrile (2:98)
Buffer: 10 mM Ammonium formate in water (pH 4.5)
  6%-100% B (0 to 1.5 min) 100% B (to 2.2 min) 100%-6% B (to
Gradient Range: 2.6 min) 6% B (to 3 min)
Gradient Time: 3 min
Flow Rate: 1.5 mL/min
Analysis Time: 3 min
Detection:
Detector 1: UV at 254 nm
Detector 2: MS (ESI+)
Method P:
Column: (LCMS) Ascentis Express C18, 5×2.1 mm, 2.7 µm particles
Mobile Phase: (A) 2:98 acetonitrile:water; (B) 98:2 acetonitrile:water
Buffer: 10 mM ammonium formate
Gradient Range: 0-100% B
Gradient Time: 1.5 min
Flow Rate: 1 mL/min
Analysis Time: 4 min
Detection:
Detector 1: UV at 220 nm
Detector 2: MS (ESI+)
Method Q:
Column: Waters Sunfire C18 (4.6×150 mm), 3.5 µm
Mobile Phase: (A) 5:95 acetonitrile:water; (B) 95:5 acetonitrile:water
Buffer: 0.1% TFA
Gradient Range: 10-100% B Gradient Time: 12 min
Flow Rate: 1 mL/min
Analysis Time: 15 min
Detection:
Detector 1: UV at 220 nm
Detector 2: UV at 254 nm Preparation 1

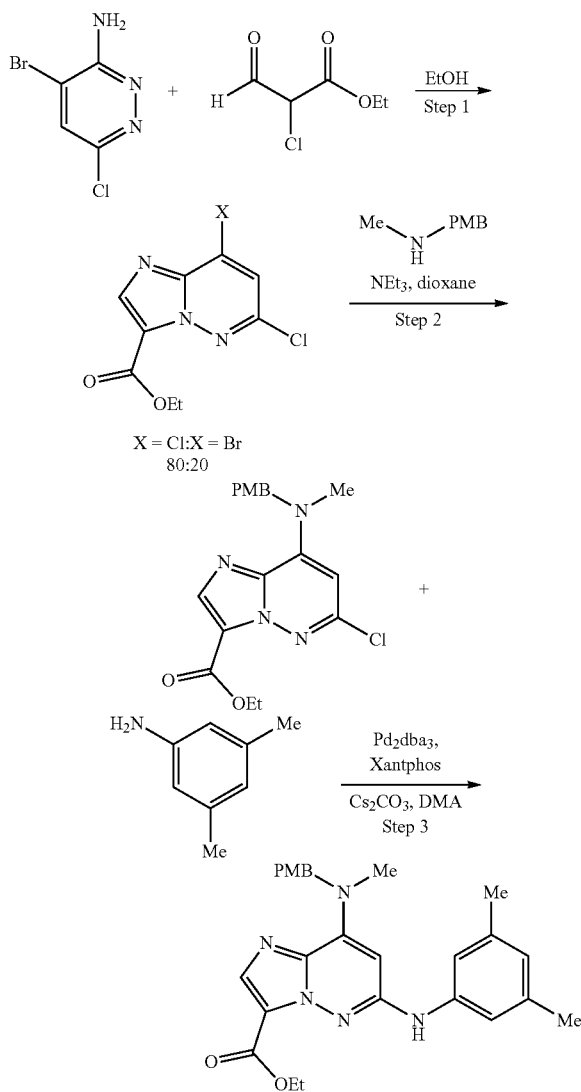

Step 1

To a solution of 4-bromo-6-chloropyridazin-3-amine (175 g, 840 mmol) in ethanol (2 L) was added ethyl 2-chloro-3-oxopropanoate (202 g, 1343 mmol) and the reaction was heated to 80° C. for 16 hours. The solvent was removed in vacuo and the residual material was diluted with water and dichloromethane. The biphasic mixture was passed through a celite bed and the filtrate was separated into two layers. The dichloromethane layer was separated and then washed with water and saturated aqueous sodium chloride (brine), it was then dried over anhydrous sodium sulfate, filtered and concentrated. The resulting crude product was purified using silica gel chromatography (0 to 20% ethyl acetate in petroleum ether). The product fractions were dried and then triturated with 10% methyl tert-butyl ether in petroleum ether (500 mL). The product was filtered off and rinsed with petroleum ether to provide the product (73 g, 33% yield) as a mixture of the C8-bromo and C8-chloro species (~80:20), the mixture was used as such in the subsequent steps (referred to as the chloride for simplicity).

$^1$H NMR (300 MHz, CDCl$_3$):

Chloro: δ 8.37 (s, 1H), 7.38 (s, 1H), 4.47 (q, J=7.2 Hz, 2H), 1.44 (t, J=7.2 Hz, 3H).

Bromo: δ 8.38 (s, 1H), 7.57 (s, 1H), 4.47 (q, J=7.2 Hz, 2H), 1.44 (t, J=7.2 Hz, 3H). LC retention time chloro: 1.04 min [O]; bromo: 1.07 [O]. Mass Spectrometry ("MS") (E+) m/z: 260 (chloro); 304 (bromo) (MH$^+$).

Step 2

A solution of ethyl 8-chloro-6-chloroimidazo[1,2-b]pyridazine-3-carboxylate (7.35 g, 28.3 mmol), 1-(4-methoxyphenyl)-N-methylmethanamine (4.74 g, 31.4 mmol) and triethylamine (6.73 mL, 48.3 mmol) in dioxane (75 mL) was heated in an oil bath at 90° C. for 2.5 hours. The reaction was cooled to room temperature and concentrated to provide a sludge that was triturated with water to provide a solid which was filtered, rinsed with water and then collected with dichloromethane. The solution was dried over anhydrous sodium sulfate, filtered and concentrated to provide the product (8.95 g, 84% yield). $^1$H NMR (400 MHz, CHLOROFORM-d) δ 8.13 (s, 1H), 7.17 (d, J=8.6 Hz, 2H), 6.87 (d, J=8.6 Hz, 2H), 6.12 (s, 1H), 5.50 (s, 2H), 4.46 (q, J=7.1 Hz, 2H), 3.81 (s, 3H), 3.18 (s, 3H), 1.74-1.58 (m, 1H), 1.44 (t, J=7.2 Hz, 3H). LC retention time 1.04 min [J]. MS (E+) m/z: 375 (MH$^+$).

Step 3

Nitrogen was bubbled through a solution of ethyl 6-chloro-8-((4-methoxybenzyl)(methyl)amino)imidazo[1,2-b]pyridazine-3-carboxylate (1.00 g, 2.67 mmol) in dimethylacetamide (DMA, 10 mL) for 15 minutes and then 3,5-dimethylaniline (0.647 g, 5.34 mmol) was added to the reaction followed by tris(dibenzylideneacetone)dipalladium (0) (Pd$_2$dba$_3$, 489 mg, 0.534 mmol), 4,5-bis(diphenylphosphino)-9,9-dimethylxanthene (Xantphos, 617 mg, 1.07 mmol) and cesium carbonate (Cs$_2$CO$_3$, 3.48 g, 10.67 mmol). The reaction was sealed and heated to 100° C. for 4 hours, after which the reaction was cooled to room temperature and ethyl acetate and water were added. The slurry was filtered and the filtrate layers were separated, the organic layer was rinsed three times with brine, dried over sodium sulfate, filtered and concentrated to provide the crude product, which was then purified using automated chromatography providing the product (710 mg, 58% yield). $^1$H NMR (400 MHz, CHLOROFORM-d) δ 8.04 (s, 1H), 7.15 (d, J=8.8 Hz, 2H), 7.10 (s, 2H), 6.84 (d, J=8.6 Hz, 2H), 6.69 (s, 1H), 6.35 (s, 1H), 5.78 (s, 1H), 5.35 (s, 2H), 4.45 (q, J=7.0 Hz, 2H), 3.79 (s, 3H), 3.10 (s, 3H), 2.31 (d, J=0.4 Hz, 6H), 1.42 (t, J=7.0 Hz, 3H). LC retention time 1.17 min [J]. MS (E+) m/z: 460 (MH$^+$).

Example 1

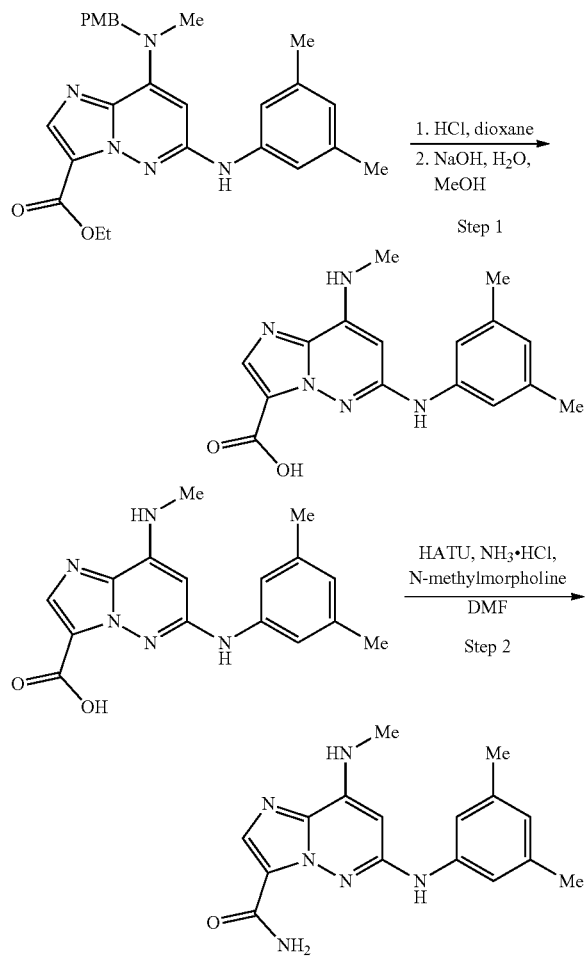

Step 1

To a solution of ethyl 6-((3,5-dimethylphenyl)amino)-8-((4-methoxybenzyl)(methyl)amino)imidazo[1,2-b]pyridazine-3-carboxylate (710 mg, 1.545 mmol) in dioxane (2 mL) was added hydrochloric acid (4 M in dioxane, 3.86 mL, 15.45 mmol). The solution was stirred at room temperature for two hours and then concentrated in vacuo. Dichloromethane was added and the solution was re-concentrated, and then more dichloromethane was added and the solution was concentrated again (repeated 5 times). The intermediate was then dissolved in methanol (5 mL) and sodium hydroxide (1 M in water, 3.09 mL, 3.09 mmol) was added. The reaction was stirred overnight and then the reaction was diluted with water and the methanol was removed in vacuo. Hydrochloric acid (1 M in water) was added until the pH measured ~3. The product was extracted with ethyl acetate (twice) and then once with dichloromethane. The combined organic layers were dried over sodium sulfate, filtered, and concentrated, providing the crude acid (480 mg, 90% yield) which was used without further purification. LC retention time 0.88 min [J]. MS (E+) m/z: 312 (MH+).

Step 2

To a solution of 6-((3,5-dimethylphenyl)amino)-8-(methylamino)imidazo[1,2-b]pyridazine-3-carboxylic acid (30 mg, 0.096 mmol) and ammonium chloride (10.31 mg, 0.193 mmol) in dimethylformamide (DMF, 1 mL) was added 1-[bis(dimethylamino)methylene]-1H-1,2,3-triazolo[4,5-b]pyridinium 3-oxid hexafluorophosphate (HATU, 44.0 mg, 0.116 mmol) and 4-methylmorpholine (48.7 mg, 0.482 mmol) and the reaction was stirred for 1 hour. The reaction was then filtered through a micropore filter, diluted with DMF and purified by preparative LC to provide the title compound (6.7 mg, 9% yield). $^1$H NMR (500 MHz, DMSO-$d_6$) δ 8.97 (s, 1H), 8.34 (d, J=2.5 Hz, 1H), 7.93 (d, J=2.5 Hz, 1H), 7.81 (s, 1H), 7.44 (d, J=5.0 Hz, 1H), 7.06 (s, 2H), 6.62 (s, 1H), 5.74 (s, 1H), 2.87 (d, J=4.5 Hz, 3H), 2.25 (s, 6H). LC retention time 1.39 min [E]. MS (E+) m/z: 312 (MH+).

The following Examples were prepared in a similar manner to the product of Example 1

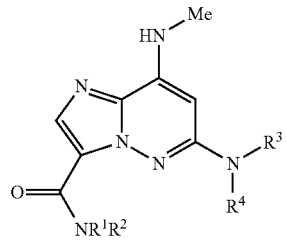

| Example number | NR$^1$R$^2$ | NR$^3$R$^4$ | Rt (min) [Method] | m/z [M + H]$^+$ |
|---|---|---|---|---|
| 2 | | | 7.90 [F] | 355 |

-continued

| Example number | NR¹R² | NR³R⁴ | Rt (min) [Method] | m/z [M + H]⁺ |
|---|---|---|---|---|
| 3 | azetidinyl | 3-fluoro-5-methylphenyl-NH- | 1.46 [E] | 355 |
| 4 | cyclobutyl-NH- | 3-fluoro-5-(trifluoromethyl)phenyl-NH- | 1.93 [E] | 423 |
| 5 | cyclobutyl-NH- | 3-(trifluoromethoxy)phenyl-NH- | 1.89 [E] | 421 |
| 6 | -NH₂ | 2,5-difluorophenyl-NH- | 1.17 [E] | 319 |
| 7 | 3-hydroxyazetidinyl | 3,5-dimethylphenyl-NH- | 1.25 [E] | 367 |
| 8 | cyclopropyl-NH- | 2,5-difluorophenyl-NH- | 1.45 [E] | 359 |
| 9 | (2-hydroxy-2-methylpropyl)-NH- | 3-fluoro-5-methylphenyl-NH- | 1.46 [E] | 387 |
| 10 | cyclobutyl-NH- | indolin-1-yl | 1.91 [E] | 363 |

-continued

| Example number | NR¹R² | NR³R⁴ | Rt (min) [Method] | m/z [M + H]⁺ |
|---|---|---|---|---|
| 11 | –NH–C(Me)₂–CH₂OH (2-hydroxy-2-methylpropyl amino) | indolin-1-yl | 1.52 [E] | 381 |
| 12 | –NH–CH₂–C(Me)₂–CH₂OH | –NH–(3,5-dimethylphenyl) | — | — |
| 13 | –NH–cyclopropyl | –NH–(2,3,5-trifluorophenyl) | 3.16 [M] | 377 |
| 14 | –NH–C(Me)₂–CH₂OH | –NH–(2,3,5-trifluorophenyl) | 2.93 [M] | 409 |
| 15 | –NH–CH₂–C(Me)₂–CH₂OH | –NH–(3,5-difluorophenyl) | 1.52 [E] | 405 |
| 16 | –NH–CH₂–C(Me)₃ (neopentylamino) | –NH–(2-methoxy-3,5-difluorophenyl) | 2.29 [E] | 419 |
| 17 | –NH–CH₂–C(Me)₂–CH₂OH | –NH–(2-methoxy-3,5-difluorophenyl) | 1.60 [E] | 435 |

-continued
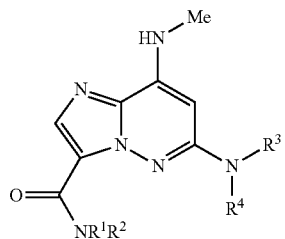
| Example number | NR¹R² | NR³R⁴ | Rt (min) [Method] | m/z [M + H]⁺ |
|---|---|---|---|---|
| 18 | ⸺NH–CH₂–C(Me)₂–CH₂OH | –NH–(2,3,5-trifluorophenyl) | 1.53 [E] | 423 |
| 19 | –NH₂ | –NH–(2,3,5-trifluorophenyl) | 1.79 [M] | 355 |
| 20 | –NH–cyclopropyl | –NH–(2,3,5-trifluorophenyl) | 0.80 [J] | 395 |
| 21 | ⸺NH–CH₂–C(OH)(Me)₂ | –NH–(2,3,5-trifluorophenyl) | 2.18 [E] | 427 |

Example 22

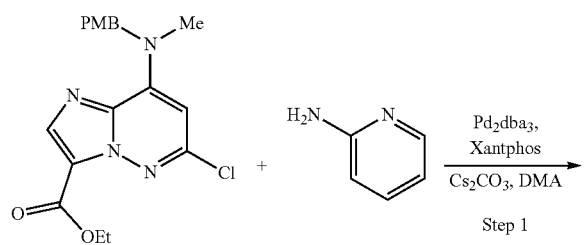

Step 1

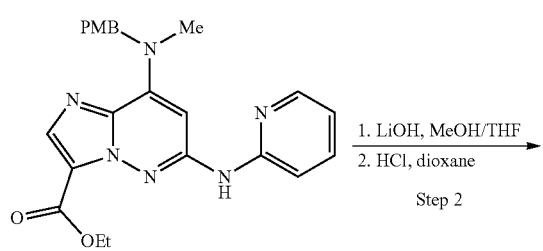

Step 2

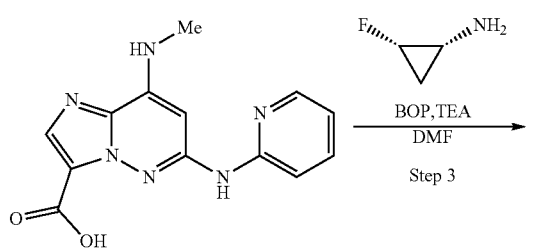

Step 1

Ethyl 6-chloro-8-((4-methoxybenzyl)(methyl)amino)imidazo[1,2-b]pyridazine-3-carboxylate (200 mg, 0.534 mmol) was dissolved in dimethylacetamide (DMA, 5 mL) at room temperature with stirring under nitrogen. Nitrogen was bubbled through the solution for 15 min. Pyridin-2-amine (100 mg, 1.067 mmol) was added to the reaction followed by $Pd_2(dba)_3$ (98 mg, 0.107 mmol), Xantphos (123 mg, 0.213 mmol) and cesium carbonate (695 mg, 2.134 mmol). The reaction vessel was sealed and heated at 100° C. for 23 hours.

The reaction was filtered then stripped to dryness under high vacuum to give an amber oil as crude product. It was purified with silica gel chromatography to obtain ethyl 8-((4-methoxybenzyl)(methyl)amino)-6-(pyridin-2-ylamino)imidazo[1,2-b]pyridazine-3-carboxylate (79 mg, 0.179 mmol, 33.5% yield) of an amber oil as product. LC retention time 0.92 min [J]. MS (E+) m/z: 433 (MH+).

Step 2

Ethyl 8-((4-methoxybenzyl)(methyl)amino)-6-(pyridin-2-ylamino)imidazo[1,2-b]pyridazine-3-carboxylate (75 mg, 0.173 mmol) was dissolved in methanol (2 mL) at room temperature with stirring then 0.5 M Lithium hydroxide (LiOH, 0.694 mL, 0.347 mmol) was added. It was heated at 50° C. for 2 hours. Solids were present. LC retention time 0.79 min [J]. MS (E+) m/z: 405 (MH+). The reaction mixture was concentrated in vacuo, and the residue was concentrated twice from methanol to remove residual water. The residue was suspended in methylene chloride, the mixture was treated with 4N hydrochloric acid (HCl) in dioxane (0.434 mL, 1.734 mmol) at 25° C. with stirring overnight reaction essentially complete. Workup entailed stripping the reaction 5 times from methylene chloride to obtain 8-(methylamino)-6-(pyridin-2-ylamino)imidazo[1,2-b]pyridazine-3-carboxylic acid, 2 HCl (50 mg, 0.126 mmol, 72.6% yield) of tan solids as product. LC retention time 0.52 min [J]. MS (E+) m/z: 285 (MH+).

Step 3

8-(methylamino)-6-(pyridin-2-ylamino)imidazo[1,2-b]pyridazine-3-carboxylic acid, 2 HCl (15 mg, 0.042 mmol), (Benzotriazol-1-yloxy)tris(dimethylamino)phosphonium hexafluorophosphate (BOP, 20.43 mg, 0.046 mmol), triethylamine (0.018 ml, 0.126 mmol) and (1R,2S)-2-fluorocyclopropanamine, pTSA (10.38 mg, 0.042 mmol) were mixed in DMF (1 mL) at 25° C. with stirring. After 1 hour the reaction completed. The reaction mixture containing the product was purified with prep HPLC to provide the title compound (4.8 mg, 0.014 mmol, 33.5% yield). LC retention time 0.76 min [J]. MS (E+) m/z: 342 (MH+). $^1$H NMR (500 MHz, METHANOL-$d_4$) δ 8.28-8.25 (m, 1H), 8.02-7.99 (m, 1H), 7.73-7.67 (m, 1H), 7.44 (d, J=7.9 Hz, 1H), 7.00-6.94 (m, 1H), 6.24-6.19 (m, 1H), 4.83-4.63 (m, 1H), 3.02 (s, 3H), 2.98-2.92 (m, 1H), 1.23 (dtd, J=14.7, 8.6, 6.2 Hz, 1H), 1.07-0.96 (m, 1H)

The following Example was prepared in a similar manner to the product of Example 22.

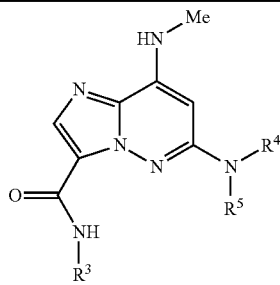

| Example number | NHR³ | NR⁴R⁵ | Reaction temperature (° C.)/time (hour) for step 1 | Rt (min) [Method] | m/z [M + H]⁺ |
|---|---|---|---|---|---|
| 23 | ![cyanocyclopropyl amine] | ![OCF3 phenylpyridinyl amine] | 100/1 | 0.99 [J] | 509 |

Example 24

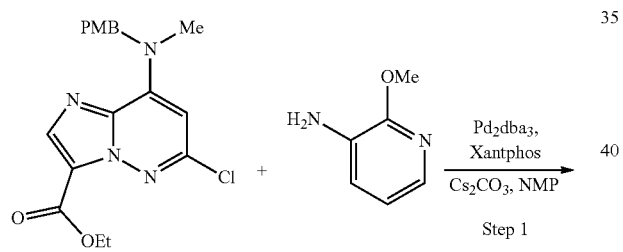

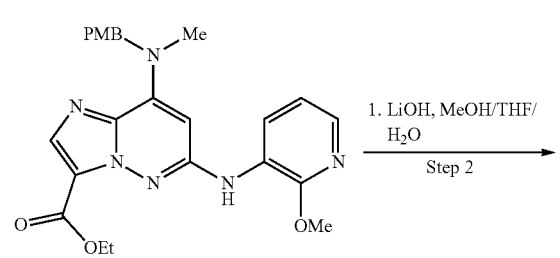

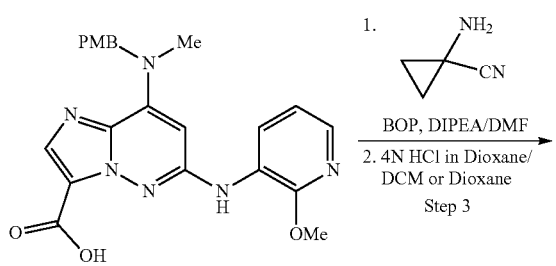

-continued

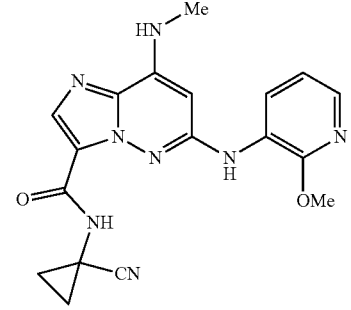

Step 1

A stirred mixture of 2-methoxypyridin-3-amine (0.149 g, 1.197 mmol), 2-methoxypyridin-3-amine (0.149 g, 1.197 mmol), $Pd_2(dba)_3$ (10.96 mg, 0.012 mmol), Xantphos (6.93 mg, 0.012 mmol) and cesium carbonate (0.975 g, 2.99 mmol) in N-Methyl-2-pyrrolidone (NMP, 25 mL) was heated at 125° C. for two hours. LC-MS showed complete conversion to the desired product mass. The reaction mixture was diluted with ethyl acetate (100 mL), and filtered. The filtrate was washed with water, dried and concentrated. The residue was dissolved in 2 mL 4M HCl in 1,4-dioxane and stirred at room temperature for 2 hours and concentrated. The concentrate was purified using Reverse-Phase PREP LC. Fractions containing product were combined and concentrated to give the product as a tan solid (0.296 g, 0.640 mmol, 64.1% yield). LC retention time 1.09 min [J]. MS (E+) m/z: 463 (MH⁺).

Step 2

A mixture of ethyl 8-((4-methoxybenzyl)(methyl)amino)-6-((2-methoxypyridin-3-yl)amino)imidazo[1,2-b]pyridazine-3-carboxylate (0.280 g, 0.605 mmol) and lithium hydroxide (0.072 g, 3.03 mmol) in THF (11 mL), methanol (5.50 mL) and water (5.00 mL) was stirred at room temperature overnight. The reaction mixture was concentrated to approximately 2 ml solution, then acidified to pH 3-4 with 1N HCl solution, stirred and filtered. The resulting tan solid was air-dried to give the desired product (0.205 g, 0.472 mmol, 78% yield). LC retention time 0.92 min [J]. MS (E+) m/z: 435 (MH$^+$).

Step 3

8-((4-methoxybenzyl)(methyl)amino)-6-((2-methoxypyridin-3-yl)amino)imidazo[1,2-b]pyridazine-3-carboxylic acid (10 mg, 0.023 mmol) was dissolved in 1.95 mL of DMF. 1-aminocyclopropanecarbonitrile (2.266 mg, 0.028 mmol), BOP (12.20 mg, 0.028 mmol) and DIPEA (0.012 mL, 0.069 mmol) were added to the reaction. The reaction was stirred at room temperature until complete. The reaction sample was blown down in the Zymark tabletop dryer at 45° C. for 2 hours. The crude reaction was dissolved in DCM (0.5 mL) and 4N HCl in dioxane (150 µL) was added to it. The reaction was stirred at room temperature. The desired product was observed. The reaction sample was placed in the SpeedVac to dry for 2 hours at 45° C. The crude sample with final volume of 1.8 mL in DMF was purified with prep HPLC to provide the title compound (2.3 mg, 6.08 µmol, 30.8% yield). LC retention time 1.18 min. MS (E+) m/z: 379 (MH$^+$). $^1$H NMR (500 MHz, DMSO-d$_6$) δ 9.21 (s, 1H), 8.58 (s, 1H), 8.27-8.09 (m, 1H), 8.03-7.78 (m, 2H), 7.55 (d, J=4.3 Hz, 1H), 7.07 (dd, J=7.3, 4.9 Hz, 1H), 6.10 (s, 1H), 3.97 (s, 3H), 2.88 (s, 3H), 1.78-1.30 (m, 2H), 1.33-0.86 (m, 2H)

The following Examples were prepared in a similar manner to the product of Example 24.

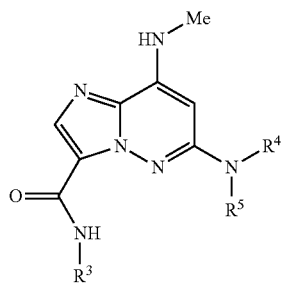

| Example number | NHR$^3$ | NR$^4$R$^5$ | Reaction temperature (° C.)/time (hour) for step 1 | Rt (min) [Method] m/z [M + H]$^+$ |
|---|---|---|---|---|
| 25 | ⸺NH-CH$_2$CH$_2$-OH | 2-methoxy-pyridin-3-ylamino | 125/2 | 358 |
| 26 | ⸺NH-CH$_2$CH$_2$-F | 2-methoxy-pyridin-3-ylamino | 125/2 | 360 |
| 27 | ⸺NH-cyclobutyl | 2-methoxy-pyridin-3-ylamino | 125/2 | 368 |
| 28 | ⸺NH-(2-hydroxycyclopentyl) | 2-(pyrazol-1-yl)pyridin-3-ylamino | 125/2 | 434 |

-continued
| Example number | NHR³ | NR⁴R⁵ | Reaction temperature (° C.)/time (hour) for step 1 | Rt (min) [Method] | m/z [M + H]⁺ |
|---|---|---|---|---|---|
| 29 | propan-2-ylamino with CH(Me)CH2OH | pyrazolyl-pyridinyl-NH | 125/2 | | 408 |
| 30 | NHCH2CH2OH | pyrazolyl-pyridinyl-NH | 125/2 | 0.71[J] | 394 |
| 31 | NHCH2C(Me)2OH | pyrazolyl-pyridinyl-NH | 125/2 | | 422 |
| 32 | NH-CH(Me)CH2OH (chiral) | pyrazolyl-pyridinyl-NH | 125/2 | 0.70[J] | 408 |
Preparation 2
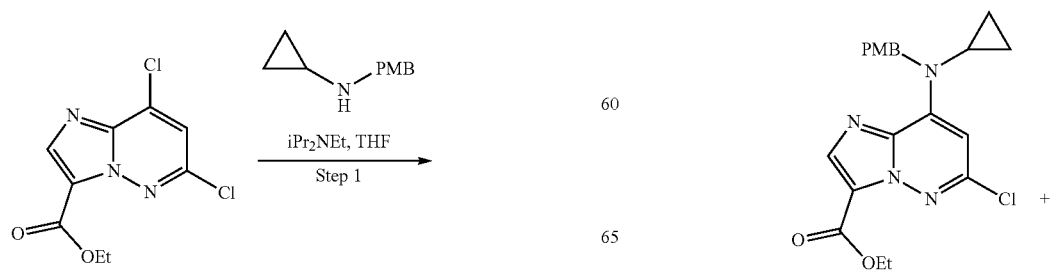

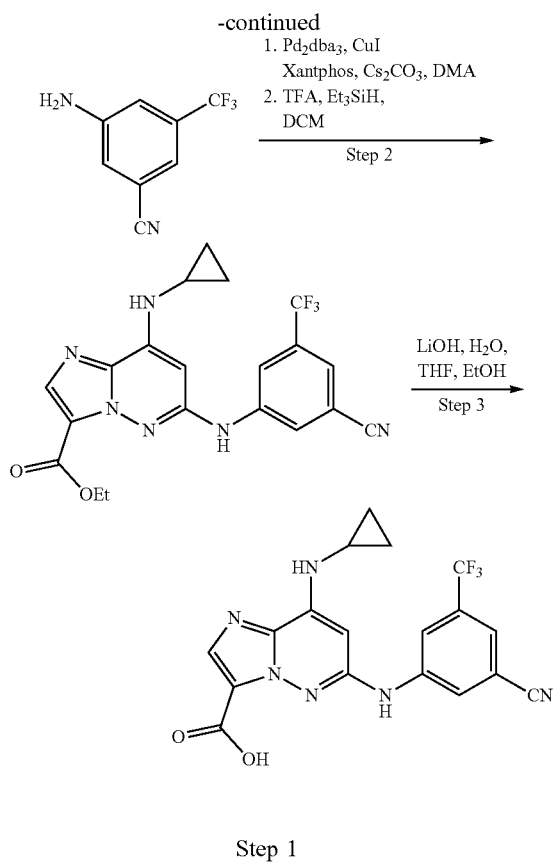

Step 1

A solution of ethyl 6,8-dichloroimidazo[1,2-b]pyridazine-3-carboxylate (4.0 g, 15.38 mmol), N-(4-methoxybenzyl)cyclopropanamine (4.09 g, 23.07 mmol) and diisopropylethyl amine (5.37 mL, 30.8 mmol) in tetrahydrofuran (THF, 5 mL) was refluxed at 70° C. overnight. The reaction was concentrated and the crude product was purified using silica gel chromatography (25-30% ethyl acetate: petroleum ether), to provide ethyl 6-chloro-8-(cyclopropyl(4-methoxybenzyl)amino)imidazo[1,2-b]pyridazine-3-carboxylate (4.3 g, 56% yield). 1H NMR (400 MHz, CHLOROFORM-D) δ ppm 8.14 (1H, s), 7.05-7.07 (1H, m), 7.02-7.05 (1H, m), 6.76-6.79 (1H, m), 6.74-6.76 (1H, m), 6.60 (1H, s), 5.61 (2H, s), 4.43 (2H, q, J=7.22 Hz), 3.75 (3H, s), 2.45-2.54 (1H, m), 1.41 (3H, t, J=7.05 Hz), 0.96-1.04 (2H, m), 0.76-0.84 (2H, m). LC retention time 2.22 min [O]. MS (E+) m/z: 401 (MH+).

Step 2

A solution of ethyl 6-chloro-8-(cyclopropyl(4-methoxybenzyl)amino) imidazo[1,2-b]pyridazine-3-carboxylate (400 mg, 1.0 mmol) in dimethylacetamide (DMA, 4 mL) was purged with nitrogen for 10 minutes at which point 3-amino-5-(trifluoromethyl)benzonitrile (371 mg, 2.00 mmol), Pd$_2$dba$_3$ (91 mg, 0.10 mmol), Xantphos (289 mg, 0.50 mmol), cesium carbonate (1300 mg, 3.99 mmol) and copper(I) iodide (38.0 mg, 0.200 mmol) were added. The tube was sealed and then heated to 125° C., after one hour the reaction was filtered through celite, eluting with ethyl acetate and the ethyl acetate was washed with brine, dried over sodium sulfate, filtered and concentrated. The crude product was then purified using automated chromatography. The collected fractions were concentrated and then suspended in dichloromethane (4 mL), triethylsilane (1.59 mL, 9.98 mmol) and trifluoroacetic acid (TFA, 2 mL) were then added and the reaction was stirred for 30 minutes. The solvent was removed in vacuo and the crude product was purified using automated chromatography (25-30% ethyl acetate:petroleum ether) to provide ethyl 6-(3-cyano-5-(trifluoromethyl)phenylamino)-8-(cyclopropylamino)imidazo[1,2-b]pyridazine-3-carboxylate (200 mg, 47% yield). 1H NMR (400 MHz, DMSO-d$_6$) δ 9.96 (s, 1H), 8.81 (s, 1H), 8.45 (s, 1H), 8.04 (s, 1H), 7.88 (s, 1H), 7.79 (s, 1H), 6.22 (s, 1H), 4.41 (q, J=7.0 Hz, 2H), 2.59 (m, 1H), 1.36 (t, J=7.0 Hz, 3H), 0.84 (m, 2H), 0.70 (m, 2H).

Step 3

To a solution of ethyl 6-((3-cyano-5-(trifluoromethyl)phenyl)amino)-8-(cyclopropylamino)imidazo[1,2-b]pyridazine-3-carboxylate (250 mg, 0.581 mmol) in ethanol (3 mL) and tetrahydrofuran (THF, 3 mL) was added a solution of lithium hydroxide (139 mg, 5.81 mmol) in water (3 mL). The reaction was stirred at room temperature for three hours and then the organic solvents were removed in vacuo. Hydrochloric acid (1.5 M, aqueous) was added to adjust the pH to ~2 resulting in a precipitate. The precipitate was collected via filtration and then purified using preparative LC to afford 6-((3-cyano-5-(trifluoromethyl)phenyl)amino)-8-(cyclopropylamino)imidazo[1,2-b]pyridazine-3-carboxylic acid (100 mg, 43% yield). 1H NMR (400 MHz, DMSO-d$_6$) δ 12.88 (s, 1H), 9.93 (s, 1H), 8.77 (s, 1H), 8.58 (s, 1H), 7.96 (s, 1H), 7.85 (d, J=1.5 Hz, 1H), 7.75 (s, 1H), 6.19 (s, 1H), 2.58 (dd, J=5.6, 3.4 Hz, 1H), 0.89-0.75 (m, 2H), 0.74-0.59 (m, 2H). C retention time 2.02 min [O]. MS (E+) m/z: 403 (MH+).

Example 33

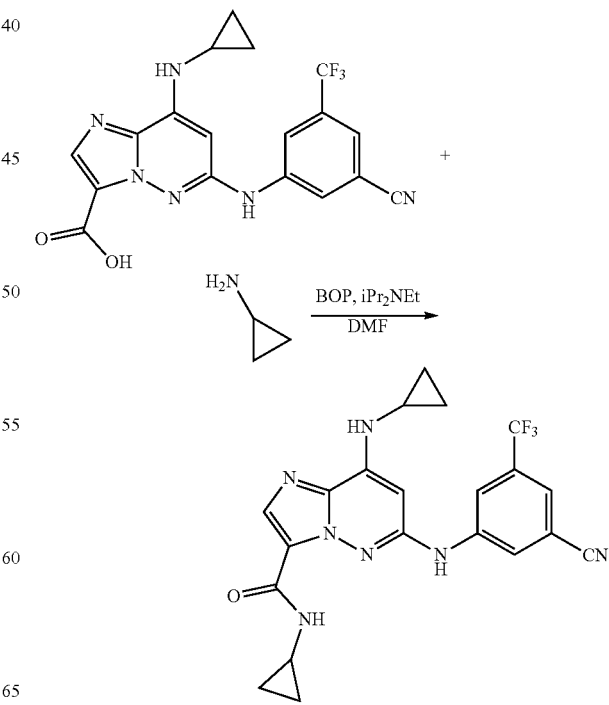

To a solution of 6-((3-cyano-5-(trifluoromethyl)phenyl)amino)-8-(cyclopropylamino)imidazo[1,2-b]pyridazine-3-carboxylic acid (10 mg, 0.025 mmol) and cyclopropanamine (2.84 mg, 0.050 mmol) in dimethylformamide (DMF, 1 mL) was added (benzotriazol-1-yloxy)tris(dimethylamino)phosphonium hexafluorophosphate (BOP, 16.5 mg, 0.037 mmol) and diisopropylethylamine (10.85 μl, 0.062 mmol). The reaction was stirred at room temperature for 4 hours and then water and ethyl acetate were added. The layers were separated and the aqueous layer extracted with ethyl acetate three times. The combined organic layers were washed with saturated sodium chloride, dried over sodium sulfate, filtered and concentrated. The crude product was purified using preparative LC to provide the title compound (4.0 mg, 36% yield). $^1$H NMR (400 MHz, DMSO-$d_6$) δ 9.81 (s, 1H), 8.46 (s, 1H), 8.34 (s, 1H), 8.04 (s, 1H), 7.94 (s, 1H), 7.87 (s, 2H), 6.14 (s, 1H), 2.80 (m, 1H), 2.58 (m, 1H), 0.84 (m, 2H), 0.81 (m, 4H), 0.73 (m, 2H). LC retention time 2.13 min [O]. MS (E+) m/z: 442 (MH$^+$).

The following Examples were prepared in a similar manner to the product of Example 33.

| Example number | NHR³ | Ar | Rt (min) [Method] | m/z [M + H]⁺ |
|---|---|---|---|---|
| 34 | NH₂ (tert-butyl) | 3-CF₃-5-CN-phenyl | 8.43 [F] | 402 |
| 35 | NH-CH₂CH₂-OH (tert-butyl) | 3-CF₃-5-CN-phenyl | 2.04 [H] | 446 |
| 36 | NH-Me (tert-butyl) | 3-CF₃-5-CN-phenyl | 2.36 [H] | 430 |
| 37 | NH₂ (tert-butyl) | 3-F-5-Me-phenyl | 2.62 [A] | 341 |
| 38 | NH-cyclopropyl (tert-butyl) | 3-F-5-Me-phenyl | 0.88 [J] | 381 |

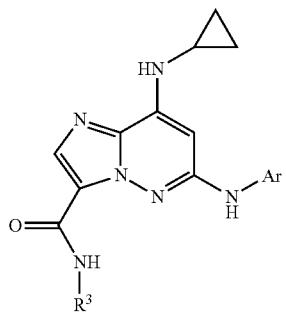

| Example number | NHR³ | Ar | Rt (min) [Method] | m/z [M + H]⁺ |
|---|---|---|---|---|
| 44 | cyclobutyl-NH- | 2,3,5-trifluorophenyl | 2.04 [P] | 417 |

Preparation 3

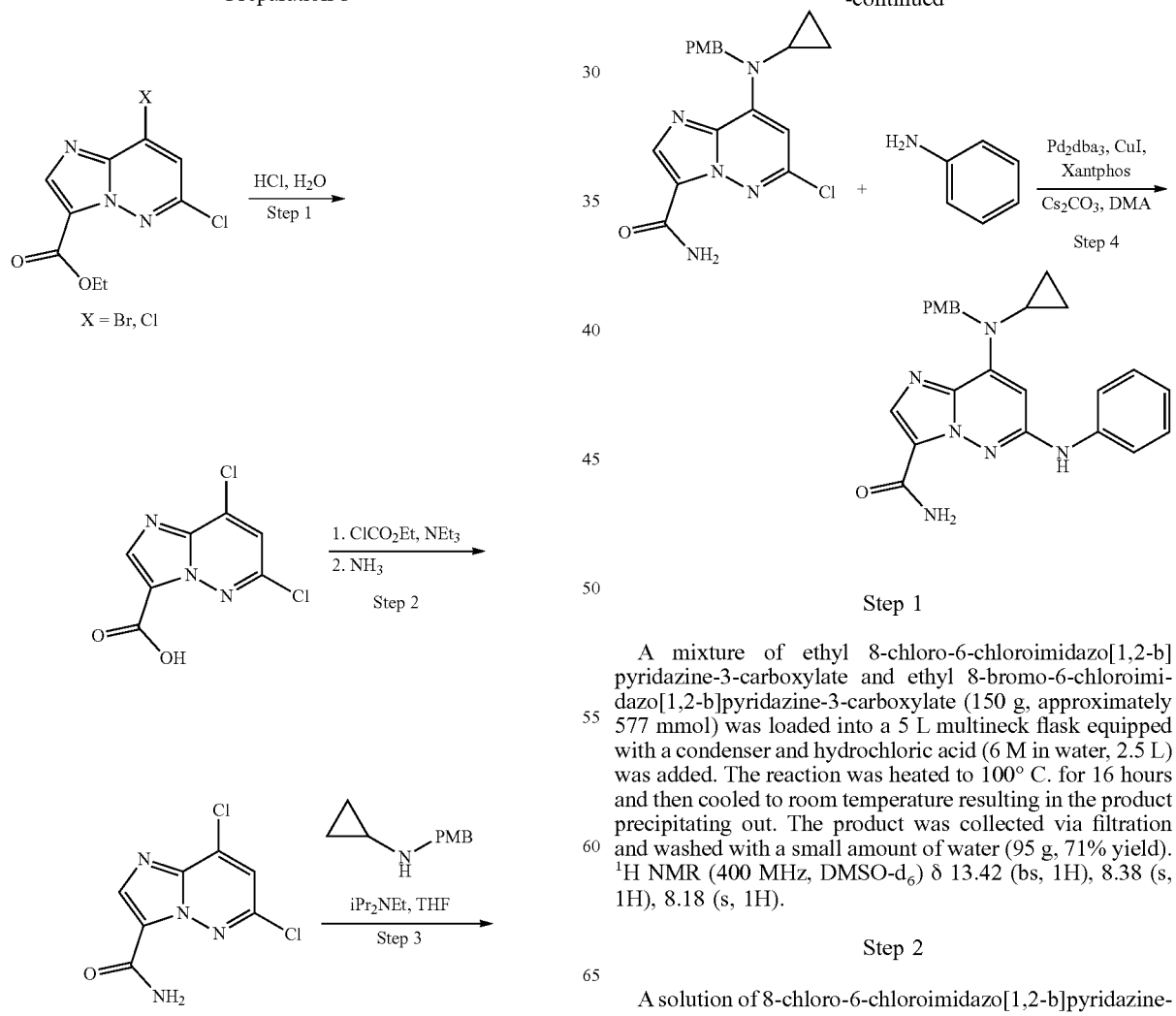

Step 1

A mixture of ethyl 8-chloro-6-chloroimidazo[1,2-b]pyridazine-3-carboxylate and ethyl 8-bromo-6-chloroimidazo[1,2-b]pyridazine-3-carboxylate (150 g, approximately 577 mmol) was loaded into a 5 L multineck flask equipped with a condenser and hydrochloric acid (6 M in water, 2.5 L) was added. The reaction was heated to 100° C. for 16 hours and then cooled to room temperature resulting in the product precipitating out. The product was collected via filtration and washed with a small amount of water (95 g, 71% yield). ¹H NMR (400 MHz, DMSO-d₆) δ 13.42 (bs, 1H), 8.38 (s, 1H), 8.18 (s, 1H).

Step 2

A solution of 8-chloro-6-chloroimidazo[1,2-b]pyridazine-3-carboxylic acid (180 g, 776 mmol) and triethylamine (151 mL, 1085 mmol) in tetrahydrofuran (THF, 1.8 L) was cooled to 0° C. Next ethyl chloroformate (118 g, 1085 mmol) in 400 ml of THF was added slowly to the reaction mixture. Once the addition was complete the reaction was warmed to room temperature and stirred for 1 hour. In a separate flask ammonia was bubbled through cooled (−30° C.) THF (1.2 L) for 30 minutes, this solution was then added gradually to the acid chloride solution at 0° C., once the addition was complete the reaction was warmed to room temperature and stirred for 1 hour. The reaction was concentrated, suspended in and stirred with water (800 mL) and then filtered, rinsing with water. The solid was air dried and collected (160 g, 90% yield). $^1$H NMR (400 MHz, DMSO-d$_6$) δ 8.33 (s, 1H), 8.14 (s, 1H), 7.99 (bs, 1H), 7.77 (bs, 1H).

Step 3

6,8-Dichloroimidazo[1,2-b]pyridazine-3-carboxamide (2.5 g, 10.9 mmol), N-(4-methoxybenzyl)cyclopropanamine (3.36 g, 18.98 mmol) and diisopropylethylamine (4.42 ml, 25.3 mmol) were dissolved in tetrahydrofuran (THF, 100 mL) and then refluxed overnight. The solvent was removed in vacuo and the crude product was taken up in chloroform and purified via chromatography to provide the product (2.6 g, 64% yield). $^1$H NMR (400 MHz, DMSO-D6) δ ppm 8.10 (1H, s), 7.96 (2H, s), 7.11 (2H, d, J=8.56 Hz), 6.83 (2H, d, J=8.81 Hz), 6.73 (1H, s), 5.65 (2H, s), 3.68 (3H, s), 2.55-2.63 (1H, m), 0.93-1.03 (2H, m), 0.76-0.84 (2H, m).

Step 4

To a solution of 6-chloro-8-(cyclopropyl(4-methoxybenzyl)amino)imidazo[1,2-b]pyridazine-3-carboxamide (125 mg, 0.337 mmol) in dimethylacetamide (DMA, 1 mL) in a nitrogen purged pressure tube, was added Xantphos (38.7 mg, 0.067 mmol), copper(I) iodide (31.8 mg, 0.167 mmol), cesium carbonate (436 mg, 1.337 mmol), and Pd$_2$(dba)$_3$ (30.6 mg, 0.033 mmol). The reaction was again purged with nitrogen (5 minutes) and then aniline (62.3 mg, 0.669 mmol) was added. The reaction was once more purged with nitrogen and then sealed and heated to 125° C. for 45 minutes. The reaction was filtered through Celite, rinsing with ethyl acetate. The filtrate was concentrated and then diluted with water and ethyl acetate, the layers were separated and the aqueous layer extracted three times with ethyl acetate. The combined organic layers were dried over sodium sulfate, filtered, concentrated and then purified using automated chromatography to provide the title compound (40 mg, 64% pure by LCMS, 18% yield), which was carried onto the next step without further purification. LC retention time 1.96 min [P]. MS (E+) m/z: 429 (MH$^+$).

Example 45

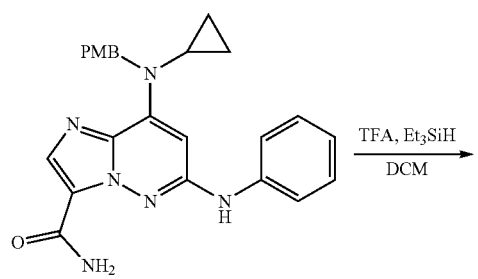

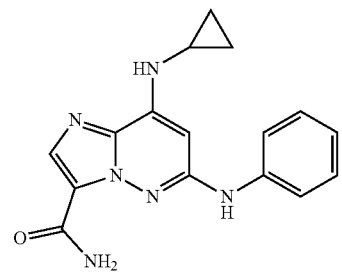

To a solution of 8-(cyclopropyl(4-methoxybenzyl) amino)-6-(phenylamino) imidazo[1,2-b]pyridazine-3-carboxamide (40 mg, 64% pure, 0.060 mmol) in dichloromethane (DCM, 1 mL) at room temperature was added triethylsilane (109 mg, 0.934 mmol) and trifluoroacetic acid (TFA, 0.3 mL). The reaction was stirred at room temperature for 20 minutes and then concentrated under reduced pressure. The crude product was purified using preparative LC to give the title compound which was isolated as the TFA salt (6.7 mg, 26% yield). $^1$H NMR (400 MHz, DMSO-d$_6$) δ 9.16 (s, 1H), 8.32 (s, 1H), 8.28 (m, 1H), 7.82 (s, 1H), 7.84 (m, 1H), 7.46 (dd, J=8.6, 1.0 Hz, 2H), 7.32 (m, 2H), 7.00 (t, J=7.2 Hz, 1H), 6.17 (s, 1H), 2.56 (m, 1H), 0.82 (m, 2H), 0.68 (m, 2H). LC retention time 7.68 min [Q]. MS (E+) m/z: 309 (MH$^+$).

The following Examples were prepared in a similar manner to the product of Example 45.

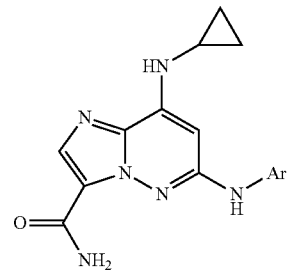

| Example number | Ar | Rt (min) [Method] | m/z [M + H]$^+$ |
|---|---|---|---|
| 46 | 3,5-dimethylphenyl (Me, Me) | 8.96 [Q] | 337 |
| 47 | 3-fluorophenyl (F) | 8.24 [Q] | 327 |

Preparation 4

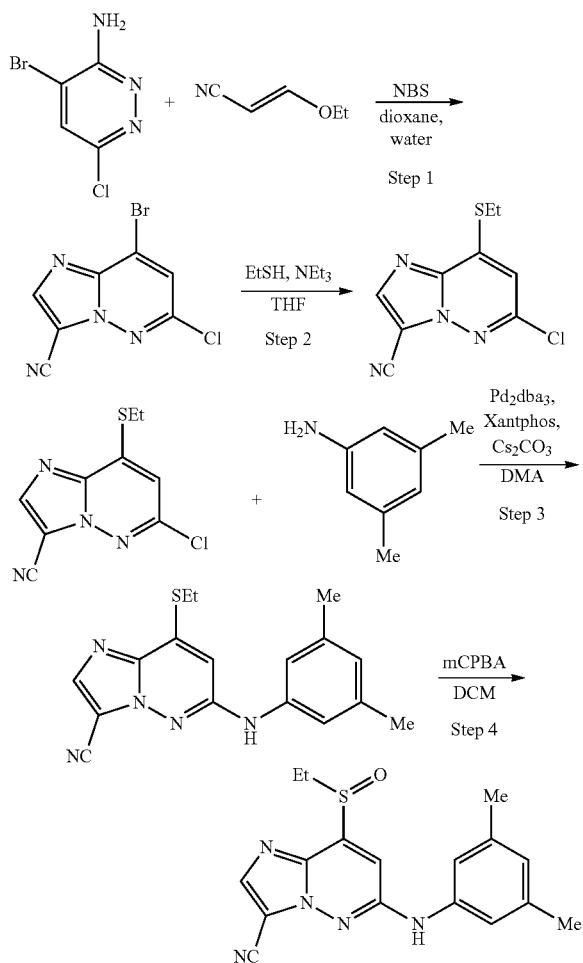

Step 1

To a solution of 3-ethoxyacrylonitrile (4.94 mL, 48.0 mmol) in dioxane (50 mL) was added water (50 mL). The solution was cooled to −10° C. and then N-bromosuccinamide (NBS, 9.39 g, 52.8 mmol) was added. The reaction was stirred at −10° C. for 2 hours and then 4-bromo-6-chloropyridazin-3-amine (10 g, 48.0 mmol) was added. The vessel was sealed and then heated in a 60° C. oil bath overnight. The reaction was cooled to room temperature, diluted with dichloromethane and then quenched with saturated (aqueous) sodium bicarbonate. The layers were separated and the aqueous layer was extracted with dichloromethane. The combined organic layers were dried over sodium sulfate, filtered, concentrated and purified using automated chromatography to give the product (3.1 g, 25%). $^1$H NMR (400 MHz, CHLOROFORM-d) δ 8.28 (s, 1H), 7.63 (s, 1H). LC retention time 0.80 min [J]. MS (E+) m/z: 259 (MH$^+$).

Step 2

To a suspension of 8-bromo-6-chloroimidazo[1,2-b]pyridazine-3-carbonitrile (6.1 g, 23.69 mmol) in tetrahydrofuran (39.5 ml) was added triethylamine (33.0 ml, 237 mmol) followed by ethanethiol (2.103 ml, 28.4 mmol). The mixture was heated to 50° C. for 10 minutes and then concentrated. The crude product was suspended in hexanes and then filtered, the powder was collected and then sonicated in ethyl acetate and filtered, rinsing with ethyl acetate. The filtrate was concentrated and purified by automated chromatography to provide the product (5.56 g, 96% yield). $^1$H NMR (400 MHz, CHLOROFORM-d) δ 8.13 (s, 1H), 6.93 (s, 1H), 3.19 (q, J=7.5 Hz, 2H), 1.53 (t, J=7.5 Hz, 3H). LC retention time 0.90 min [J]. MS (E+) m/z: 239 (MH$^+$).

Step 3

To a nitrogen purged solution of 6-chloro-8-(ethylthio) imidazo[1,2-b]pyridazine-3-carbonitrile (3.16 g, 13.24 mmol) in dimethylacetamide (DMA, 65 mL) was added 3,5-dimethylaniline (3.30 mL, 26.5 mmol), followed by Pd$_2$dba$_3$ (2.425 g, 2.65 mmol), cesium carbonate (17.25 g, 53.0 mmol), and Xantphos (3.06 g, 5.30 mmol) in a single portion. The reaction vessel evacuated and backfilled with nitrogen (×3), sealed and then heated to 125° C. for 90 minutes. The reaction was cooled to room temperature and filtered through celite, eluting with ethyl acetate. The ethyl acetate layer was washed three times with water, dried over sodium sulfate, filtered, concentrated and then purified using flash chromatography to provide the product (2.9 g, 61% yield). LC retention time 1.01 min [J]. MS (E+) m/z: 324 (MH$^+$).

Step 4

To a solution of 6-((3,5-dimethylphenyl)amino)-8-(ethylthio)imidazo[1,2-b]pyridazine-3-carbonitrile (1.187 g, 3.67 mmol) in dichloromethane (36.7 ml) was added 3-chloroperbenzoic acid (mCPBA, 75% by weight, 1.056 g, 4.59 mmol). The reaction was stirred for 20 minutes and then concentrated, the crude product was suspended in ethyl acetate and filtered, rinsing with ethyl acetate to provide the racemic title compound (762 mg, 55% yield). LC retention time 0.94 min [J]. MS (E+) m/z: 340 (MH$^+$).

Example 48

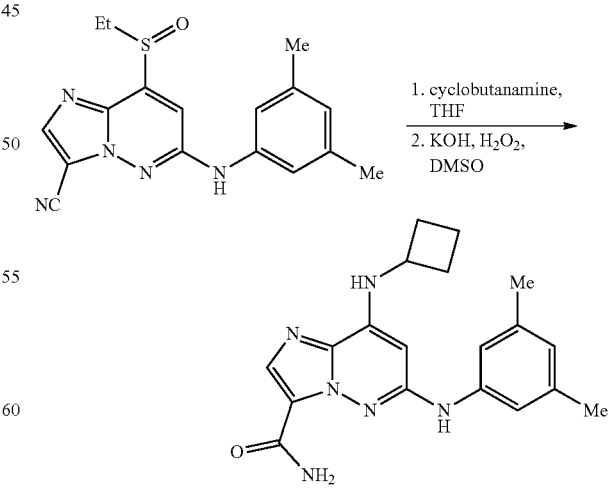

To a solution of 6-((3,5-dimethylphenyl)amino)-8-(ethylsulfinyl)imidazo[1,2-b]pyridazine-3-carbonitrile (7 mg, 0.021 mmol) in tetrahydrofuran (0.2 ml) was added cyclobutanamine (0.075 ml, 0.884 mmol). The reaction was sealed and heated to 85° C. overnight. The reaction was concentrated and then the intermediate was dissolved in dimethylsulfoxide (DMSO, 0.20 mL) and potassium hydroxide (5 M in water, 0.044 mL, 0.22 mmol) and hydrogen peroxide (33%, 0.041 mL, 0.44 mmol) were added. The reaction was run at room temperature for 14 minutes and then quenched via the addition of 1 M (aqueous) hydrochloric acid. The resulting solid was collected via filtration, dissolved in methanol and purified using preparative LC providing the title compound as a trifluoroacetate salt (2.2 mg, 11% yield). $^1$H NMR (400 MHz, METHANOL-$d_4$) δ 8.08 (br. s., 1H), 7.05 (s, 1H), 6.73 (s, 1H), 5.89 (s, 1H), 4.12 (quin, J=7.7 Hz, 1H), 2.54 (dd, J=11.4, 4.0 Hz, 2H), 2.30 (s, 6H), 2.21-2.03 (m, 2H), 2.02-1.82 (m, 2H). LC retention time 0.85 min [J]. MS (E+) m/z: 351 (MH$^+$).

The following Examples were prepared in a similar manner to the product of Example 48.

| Example number | R | Ar | Rt (min) [Method] | m/z [M + H]$^+$ |
|---|---|---|---|---|
| 49 | cyclopentyl | 3,5-dimethylphenyl | 3.06 [I] | 365 |
| 50 | -(CH$_2$)$_3$NMe$_2$ | 3,5-dimethylphenyl | 1.93 [I] | 382 |
| 51 | -CH$_2$-cyclopropyl | 3,5-dimethylphenyl | 1.68 [E] | 351 |
| 52 | -(CH$_2$)$_2$OH | 3,5-dimethylphenyl | 1.15 [G] | 341 |
| 53 | -CH$_2$CH(Me)$_2$ | 3,5-dimethylphenyl | 1.66 [G] | 353 |

-continued
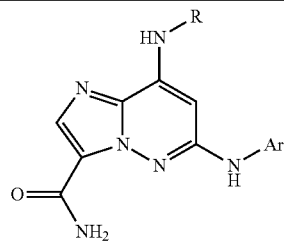
| Example number | R | Ar | Rt (min) [Method] | m/z [M + H]+ |
|---|---|---|---|---|
| 54 | ⁓Me | 3,5-diMe-phenyl | 1.54 [G] | 339 |
| 55 | ⁓Et | 3,5-diMe-phenyl | 1.95 [E] | 367 |
| 56 | ⁓OMe | 3,5-diMe-phenyl | 1.34 [G] | 355 |
| 58 | ⁓NMe₂ | 3,5-diMe-phenyl | 1.25 [E] | 368 |
Example 59
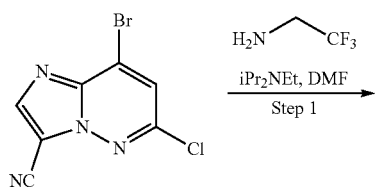
H₂N―CF₃, iPr₂NEt, DMF
Step 1
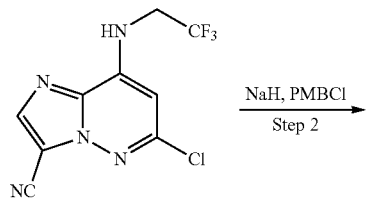
NaH, PMBCl
Step 2
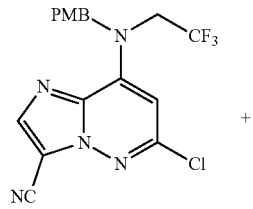
+
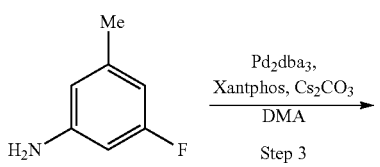
Pd₂dba₃, Xantphos, Cs₂CO₃
DMA
Step 3

-continued

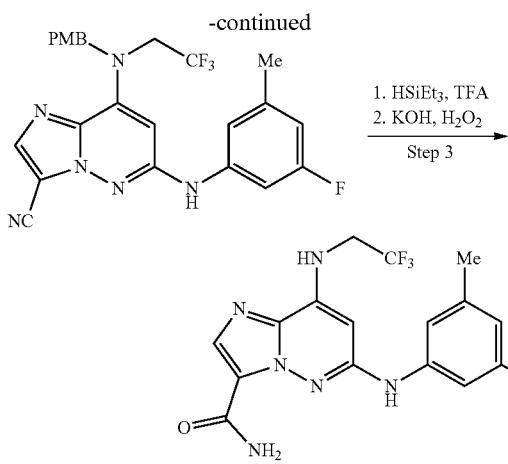

Step 1

To a solution of 8-bromo-6-chloroimidazo[1,2-b]pyridazine-3-carbonitrile (from Preparation 4, 1 g, 3.89 mmol) in dimethylformamide (5 mL) was added 2,2,2-trifluoroethanamine (0.5 mL, 6.28 mmol), the reaction vessel was sealed and heated to 85° C. overnight. Water was added to the reaction resulting in the precipitation of the product, the powder was filtered off, rinsed with water and methanol and dried to provide the product (950 mg, 89% yield). $^1$H NMR (400 MHz, DMSO-$d_6$) δ 8.71 (t, J=6.5 Hz, 1H), 8.41 (s, 1H), 6.91 (s, 1H), 4.34 (br. s., 2H). LC retention time 0.86 min [J]. MS (E+) m/z: 276 (MH$^+$).

Step 2

To 6-Chloro-8-((2,2,2-trifluoroethyl)amino)imidazo[1,2-b]pyridazine-3-carbonitrile (0.5 g, 1.814 mmol) in dimethylformamide (16 mL) at 0° C. was added sodium hydride (60 wt %, 0.167 g, 4.17 mmol), followed by 1-(chloromethyl)-4-methoxybenzene (0.517 mL, 3.81 mmol). After 10 minutes, the ice bath was removed and the reaction mixture stirred at room temperature for 18 hours. The reaction was diluted with saturated aqueous ammonium chloride and extracted with ethyl acetate (twice). The combined organic layers were washed with water, dried over sodium sulfate, filtered and concentrated. The crude product was then purified using flash chromatography (4:1 Hexanes:EtOAc) to provide the product (307 mg, 43% yield). LC retention time 1.07 min [J]. MS (E+) m/z: 396 (MH$^+$).

Step 3

6-Chloro-8-((4-methoxybenzyl)(2,2,2-trifluoroethyl)amino)imidazo[1,2-b]pyridazine-3-carbonitrile (40 mg, 0.101 mmol) was dissolved in dimethylacetamide (0.9 mL). The vessel was purged with nitrogen for 15 minutes and then 3-fluoro-5-methylaniline (25.3 mg, 0.202 mmol), Pd$_2$(dba)$_3$ (9.26 mg, 10.11 μmol), Xantphos (11.70 mg, 0.020 mmol) and cesium carbonate (132 mg, 0.404 mmol) were added. The reaction vessel was sealed and heated at 125° C. for 1 hour. The reaction was cooled to room temperature and diluted with ethyl acetate (200 mL). The solution was washed with water three times, and the organic layer dried over sodium sulfate. The slurry was filtered and concentrated to provide a crude product, which was then purified using automated chromatography, providing the intermediate product (22 mg, 46% yield). LC retention time 1.14 min [J]. MS (E+) m/z: 485 (MH$^+$).

Step 4

To a solution of 6-((3-fluoro-5-methylphenyl)amino)-8-((4-methoxybenzyl)(2,2,2-trifluoroethyl)amino)imidazo[1,2-b]pyridazine-3-carbonitrile (20 mg, 0.041 mmol) in dichloromethane (1 mL) was added triethylsilane (0.066 mL, 0.413 mmol) and then trifluoroacetic acid (1 mL). The reaction was stirred at room temperature for 10 minutes and then the solvents were removed under a stream of nitrogen. The crude intermediate was dissolved in dimethylsulfoxide (0.3 mL) and potassium hydroxide (5 M solution in water, 0.082 mL, 0.410 mmol) was added, followed by the careful addition of hydrogen peroxide (30% in water, 0.084 mL, 0.820 mmol). The reaction was stirred at room temperature until completion and then 1 M hydrochloric acid was added and the resulting precipitate was collected via filtration and then purified using preparative HPLC to provide the title compound as the TFA salt (8.8 mg, 42% yield). $^1$H NMR (400 MHz, METHANOL-$d_4$) δ 8.02 (s, 1H), 7.11 (s, 1H), 7.04-6.97 (m, 1H), 6.62 (d, J=9.5 Hz, 1H), 6.11 (s, 1H), 4.15 (q, J=9.0 Hz, 2H), 2.35 (s, 3H). LC retention time 0.82 min [J]. MS (E+) m/z: 383 (MH$^+$).

Preparation 5

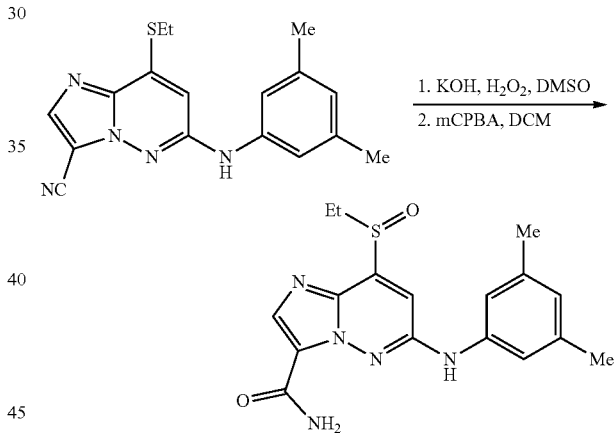

To a solution of 6-((3,5-dimethylphenyl)amino)-8-(ethylthio)imidazo[1,2-b]pyridazine-3-carbonitrile (0.9 g, 2.78 mmol) in dimethylsulfoxide (DMSO, 16 mL) was added potassium hydroxide (5 M in water, 2.78 mL, 13.91 mmol) followed by the careful addition of hydrogen peroxide (33%, 2.84 mL, 27.8 mmol). The reaction was stirred at room temperature for 20 minutes and then quenched with hydrochloric acid (1 M aqueous). The resulting precipitate was suspended in dichloromethane and concentrated in vacuo, the resulting solid was then concentrated from toluene and then again from dichloromethane. The intermediate was dissolved in dichloromethane (250 mL) and 3-chloroperbenzoic acid (75%, 0.624 g, 3.52 mmol) was added. The reaction was stirred for 20 minutes and then concentrated, the crude product was triturated with ethyl acetate and filtered, rinsing with ethyl acetate. The product was collected as a yellow powder (668 mg, 64% yield). $^1$H NMR (400 MHz, DMSO-$d_6$) δ 9.79 (s, 1H), 8.09 (br. s., 1H), 8.06-7.97 (m, 2H), 7.35 (s, 1H), 7.22 (s, 2H), 6.74 (s, 1H), 3.50 (dd, J=13.9, 7.3 Hz, 1H), 3.26 (dd, J=14.0, 7.4 Hz, 1H), 2.29 (s, 6H), 1.12 (t, J=7.4 Hz, 3H). LC retention time 0.74 min [J]. MS (E+) m/z: 358 (MH+).

Example 60

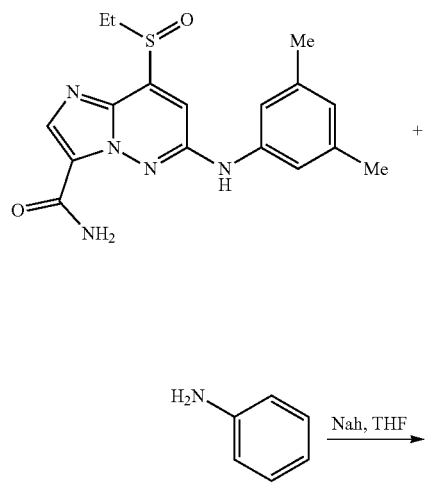

-continued

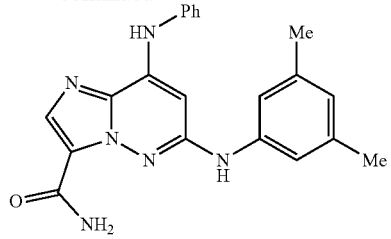

To a suspension of 6-((3,5-dimethylphenyl)amino)-8-(ethylsulfinyl)imidazo[1,2-b]pyridazine-3-carboxamide (10 mg, 0.028 mmol) in tetrahydrofuran (0.2 mL) was added aniline (0.038 mL, 0.420 mmol) and the vessel was purged of air using a stream of nitrogen. Next sodium hydride (60%, 11.19 mg, 0.280 mmol) was added and the reaction was heated to 75° C. After 30 minutes the solvent was removed in vacuo and the product was purified using preparative LC to provide the title compound as the trifluoroacetate salt (5.5 mg, 38% yield). $^1$H NMR (400 MHz, CHLOROFORM-d) δ 8.63 (br. s., 1H), 8.20 (s, 1H), 7.50-7.41 (m, 2H), 7.39-7.33 (m, 2H), 6.95 (s, 2H), 6.80 (s, 1H), 6.34 (s, 1H), 6.17 (s, 1H), 5.73 (br. s., 1H), 2.32 (s, 6H). LC retention time 0.91 min [J]. MS (E+) m/z: 373 (MH+).

The following Examples were prepared in a similar manner to the product of Example 60.

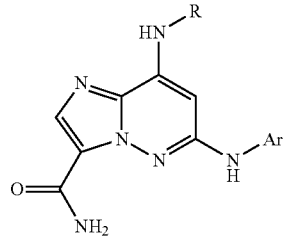

| Example number | R | Ar | Rt (min) [Method] | m/z [M + H]+ |
|---|---|---|---|---|
| 61 | 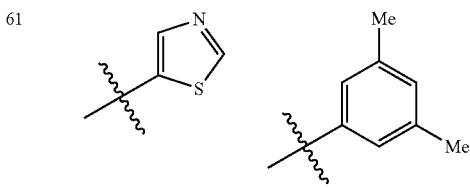 | | | |
| 62 | 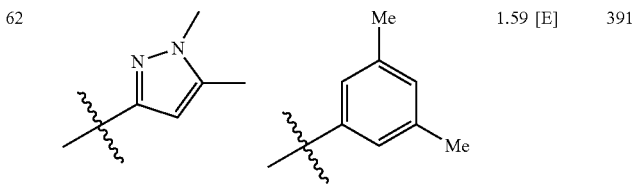 | | 1.59 [E] | 391 |
| 63 | 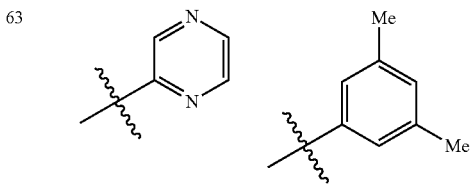 | | | |

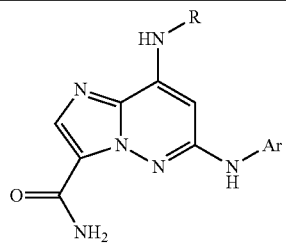

| Example number | R | Ar | Rt (min) [Method] | m/z [M + H]+ |
|---|---|---|---|---|
| 64 | (3-pyridyl) | 3,5-dimethylphenyl | | |

Example 65

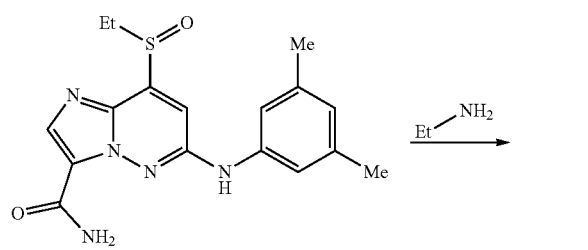

Preparation 6

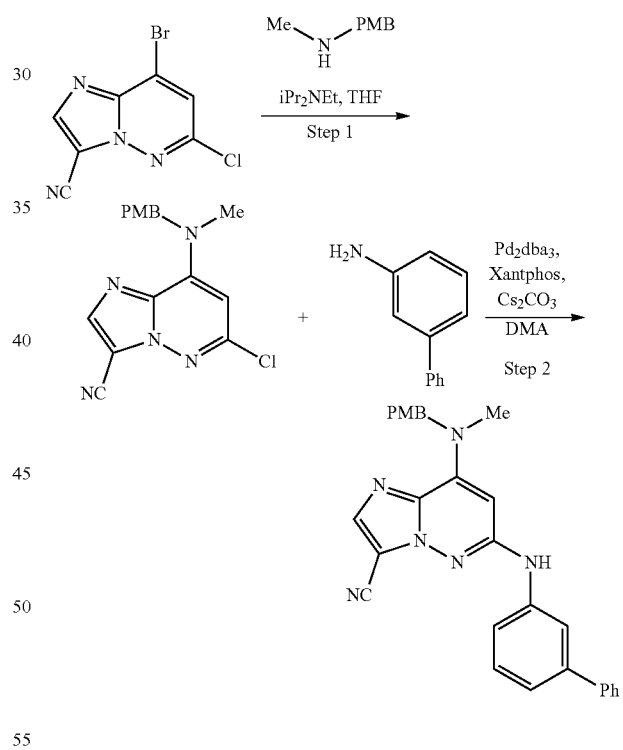

Step 1

To a 2 dram vial was added 6-((3,5-dimethylphenyl)amino)-8-(ethylsulfinyl)imidazo[1,2-b]pyridazine-3-carboxamide (15 mg, 0.042 mmol) along with anhydrous methanol (1 mL). Gaseous ethanamine was bubbled through the vessel for several minutes, the vial was then capped and heated at 80° C. overnight. The crude material was dissolved in dimethylformamide and purified using preparative LC to give the title compound. $^1$H NMR (500 MHz, METHANOL-$d_4$) δ 7.57 (s, 2H), 7.03 (s, 2H), 6.68 (s, 1H), 5.81 (s, 1H), 3.35-3.28 (m, 2H), 2.28 (s, 6H), 1.36 (t, J=7.2 Hz, 3H). LC retention time 1.79 min [E]. MS (E+) m/z: 325 (MH+).

Step 1

A solution of 8-bromo-6-chloroimidazo[1,2-b]pyridazine-3-carbonitrile (2.82 g, 13.23 mmol), 1-(4-methoxyphenyl)-N-methylmethanamine (2.00 g, 13.23 mmol) and diisopropylethylamine (4.62 mL, 26.5 mmol) in tetrahydrofuran (25 mL) was heated to 60° C. for 3 hours and then concentrated to dryness. The crude product was triturated with methanol and filtered rinsing with methanol. The solid was dried and collected as is (3.85 g, 89% yield). $^1$H NMR (400 MHz, CHLOROFORM-d) δ 7.99 (s, 1H), 7.16 (d, J=8.8 Hz, 2H), 6.93-6.82 (m, 2H), 6.12 (s, 1H), 5.45 (br. s., 2H), 3.80 (s, 3H), 3.20 (br. s., 3H). LC retention time 1.05 min [J]. MS (E+) m/z: 328 (MH+).

Step 2

Nitrogen was bubbled through a solution of 6-chloro-8-((4-methoxybenzyl)(methyl)amino)imidazo[1,2-b]pyridazine-3-carbonitrile (75 mg, 0.229 mmol) in dimethylacetamide (DMA, 2 mL) for 15 minutes and then [1,1'-biphenyl]-3-amine (77 mg, 0.458 mmol) was added, followed by Pd$_2$(dba)$_3$ (41.9 mg, 0.046 mmol), Xantphos (53.0 mg, 0.092 mmol) and cesium carbonate (298 mg, 0.915 mmol). The reaction vessel was sealed and heated to 125° C. for 2 hours. The reaction was cooled to room temperature and ethyl acetate and water were added. The suspension was filtered and the filtrate layers separated. The organic layer was dried over sodium sulfate, filtered, concentrated and purified using flash chromatography providing the coupling product (90 mg, 77% yield). LC retention time 1.17 min [J]. MS (E+) m/z: 461 (MH+).

Example 66

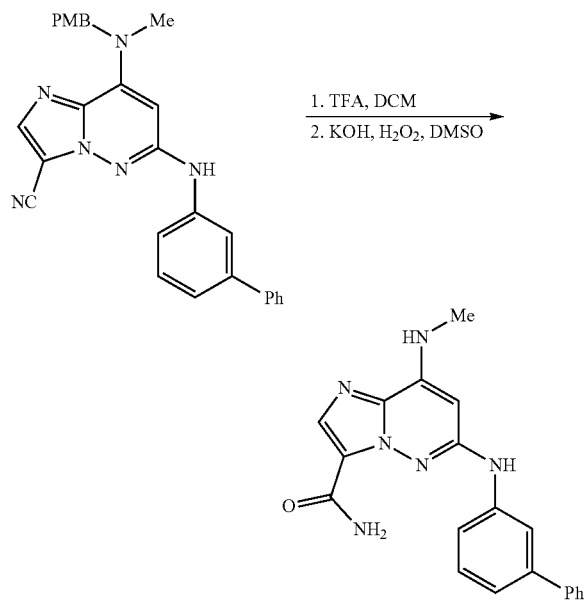

To a solution of 6-([1,1'-biphenyl]-3-ylamino)-8-((4-methoxybenzyl)(methyl)amino)imidazo[1,2-b]pyridazine-3-carbonitrile (90 mg, 0.195 mmol) in dichloromethane (3 mL) was added trifluoroacetic acid (TFA, 0.376 mL, 4.89 mmol) and the reaction was stirred overnight. The solvent was stripped off leaving the crude intermediate, as well as unreacted starting material as the presumed TFA salts. This material was dissolved in dimethylsulfoxide (0.5 mL) and potassium hydroxide (5 M in water, 0.154 mL, 0.770 mmol) was added followed by hydrogen peroxide (33%, 0.047 mL, 1.540 mmol). The reaction was run at room temperature for 1 hour and then hydrochloric acid (4 drops, 1 M in water) was added to quench the peroxide. The crude product was purified using preparative LC to provide the title compound (6.0 mg, 9% yield). $^1$H NMR (500 MHz, DMSO-d$_6$) δ 9.20 (s, 1H), 8.30 (br. s., 1H), 7.84 (s, 1H), 7.77 (br. s., 1H), 7.67-7.60 (m, 3H), 7.54-7.45 (m, 4H), 7.43-7.34 (m, 2H), 7.27 (d, J=7.9 Hz, 1H), 5.80 (s, 1H), 2.94-2.84 (m, 3H). LC retention time 1.57 min [E]. MS (E+) m/z: 359 (MH+).

Example 67

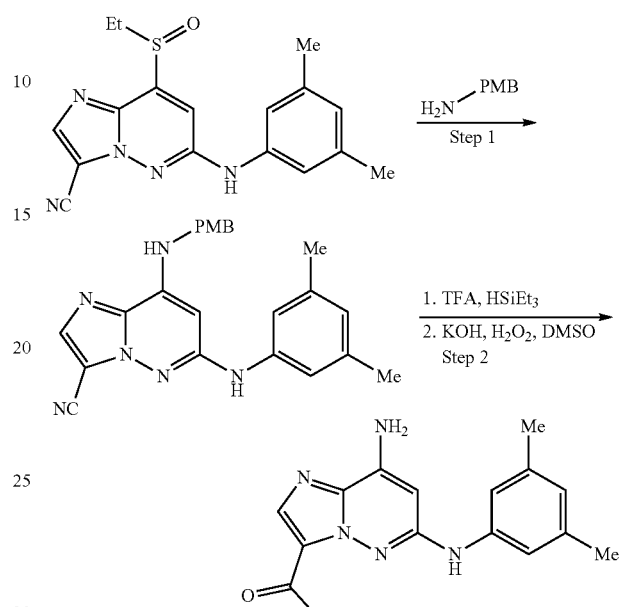

Step 1

6-((3,5-Dimethylphenyl)amino)-8-(ethylsulfinyl)imidazo[1,2-b]pyridazine-3-carbonitrile (0.033 g, 0.097 mmol) was combined with (4-methoxyphenyl)methanamine (0.6 mL, 4.59 mmol) in a reaction vial, sealed and heated to 100° C. for three hours. The crude material was purified using automated chromatography to provide the crude product (65 mg, 40% pure, 67% yield). LC retention time 1.07 min [J]. MS (E+) m/z: 399 (MH+).

Step 2

6-((3,5-Dimethylphenyl)amino)-8-((4-methoxybenzyl)amino)imidazo[1,2-b]pyridazine-3-carbonitrile (0.018 g, 0.045 mmol) and triethylsilane (0.072 mL, 0.452 mmol) were combined in a nitrogen purged vial and then trifluoroacetic acid (TFA, 0.5 mL) was subsequently added. The reaction was stirred at 50° C. for one hour and then the TFA was removed under a stream of nitrogen. The residual material was dissolved in dimethylsulfoxide (DMSO, 0.2 mL) and potassium hydroxide (5 M in water, 0.045 mL, 0.23 mmol) and hydrogen peroxide (33%, 0.046 mL, 0.45 mmol) were added. The reaction was run for 30 minutes and then the crude product was precipitated out of solution via the addition of hydrochloric acid (1 M in water). The crude product was collected via filtration and then purified using preparative LC to provide the title compound (collected as the TFA salt, 8.2 mg, 44% yield). $^1$H NMR (400 MHz, DMSO-d$_6$) δ 8.89 (s, 1H), 8.34 (br. s., 1H), 7.90 (br. s., 1H), 7.85 (s, 1H), 7.04 (s, 2H), 6.93 (br. s., 2H), 6.62 (s, 1H), 5.97 (s, 1H), 2.25 (s, 6H). LC retention time 6.32 min [F]. MS (E+) m/z: 297 (MH+).

Preparation 7

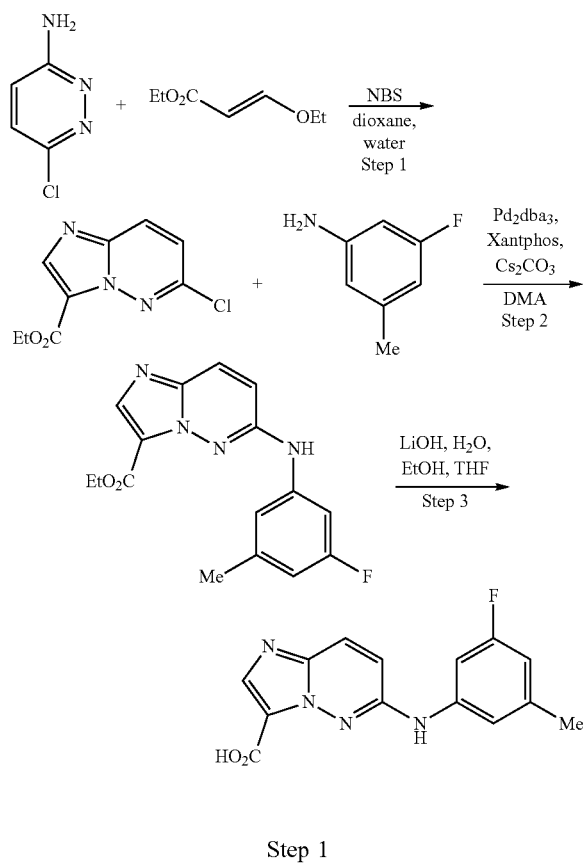

Step 1

To a cooled (−10° C.) solution of (E)-ethyl 3-ethoxyacrylate (1 g, 6.94 mmol) in water (4 mL) and dioxane (4 mL) was added N-bromosuccinamide (NBS, 1.36 g, 7.63 mmol). The reaction was warmed to room temperature and stirred for one hour, at which point 6-chloropyridazin-3-amine (0.899 g, 6.94 mmol) was added reaction mixture was heated 80° C. for one hour. The reaction was cooled to room temperature and quenched via the addition of water. The product was extracted with ethyl acetate and the combined organic layers were washed with saturated (aq.) sodium chloride, dried over sodium sulfate, filtered, concentrated and purified using automated chromatography to provide ethyl 6-chloroimidazo[1,2-b]pyridazine-3-carboxylate (1 g, 61% yield). LC retention time 1.42 min [O]. MS (E+) m/z: 226 (MH+).

Step 2

Nitrogen was bubbled through a solution of ethyl 6-chloroimidazo[1,2-b]pyridazine-3-carboxylate (500 mg, 2.216 mmol) in dimethylacetamide (DMA, 5 mL) for 15 minutes and then 3-fluoro-5-methylaniline (555 mg, 4.43 mmol) was added, followed by Pd$_2$(dba)$_3$ (203 mg, 0.222 mmol), Xantphos (256 mg, 0.443 mmol) and cesium carbonate (2888 mg, 8.86 mmol). The reaction vessel was sealed and heated to 125° C. for 1 hour. The reaction was cooled to room temperature and ethyl acetate and water were added. The suspension was filtered and the filtrate layers separated. The organic layer was dried over sodium sulfate, filtered, concentrated and purified using flash chromatography providing the coupling product (180 mg, 19% yield). LC retention time 1.95 min [O]. MS (E+) m/z: 315 (MH+).

Step 3

To a cooled (0° C.) solution of ethyl 6-((3-fluoro-5-methylphenyl)amino)-3,8a-dihydroimidazo[1,2-b]pyridazine-3-carboxylate (160 mg, 0.506 mmol) ethanol (3 mL) and tetrahydrofuran (3 mL) was added lithium hydroxide (121 mg, 5.06 mmol) in water (3 mL). The reaction was warmed to room temperature and stirred for three hours. The organic solvents were removed in vacuo and then hydrochloric acid (1.5 M in water) was added to adjust the pH to ~2, resulting in the precipitation of the crude product. The product was collected by filtration and then purified using automated chromatography to get 6-((3-fluoro-5-methylphenyl)amino)-3,8a-dihydroimidazo[1,2-b]pyridazine-3-carboxylic acid (90 mg, 46% yield). LC retention time 1.50 min [O]. MS (E+) m/z: 289 (MH+).

Example 68

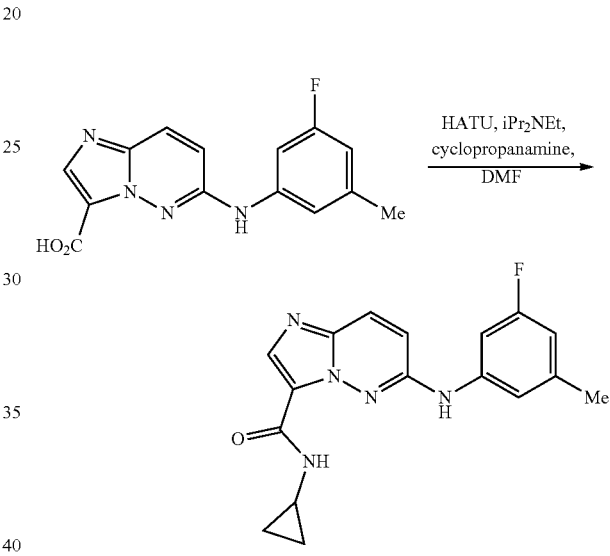

To a solution of 6-((3-fluoro-5-methylphenyl)amino)-3,8a-dihydroimidazo[1,2-b]pyridazine-3-carboxylic acid (40 mg, 0.139 mmol) and cyclopropanamine (15.8 mg, 0.278 mmol) in dimethylformamide (DMF, 1 mL) was added 1-[bis(dimethylamino)methylene]-1H-1,2,3-triazolo[4,5-b]pyridinium 3-oxid hexafluorophosphate (HATU, 106 mg, 0.278 mmol) and diisopropylethylamine (0.048 mL, 0.28 mmol) and the reaction was stirred for 1 hour. The reaction was then filtered through a micropore filter, diluted with DMF and purified by preparative LC to provide the title compound (14.4 mg, 30% yield). $^1$H NMR (400 MHz, DMSO-d$_6$) δ 9.75 (s, 1H), 8.43 (br. s., 1H), 8.06 (m, 2H), 7.39 (d, J=11.2 Hz, 1H), 7.08 (m, 2H), 6.77 (d, J=9.6 Hz, 1H), 2.86 (m, 1H), 2.35 (m, 3H), 0.73 (m, 2H), 0.44 (m, 2H). LC retention time 7.32 min [Q]. MS (E+) m/z: 326 (MH+).

Preparation 8

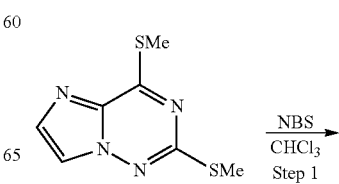

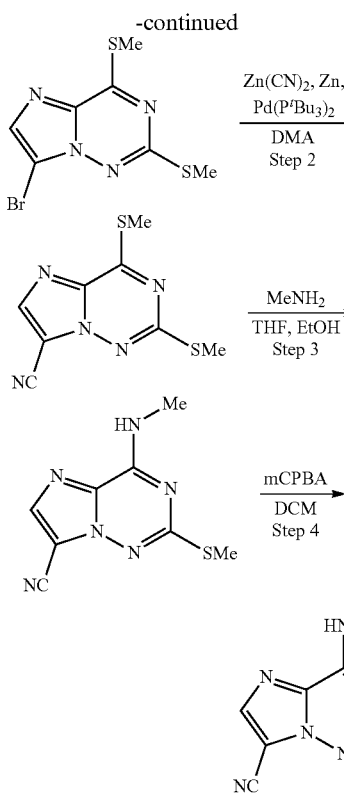

Step 1

A mixture of 2,4-bis(methylthio)imidazo[1,2-f][1,2,4]triazine (5 g, 23.55 mmol) and N-bromosuccinamide (NBS, 5.87 g, 33.0 mmol) in chloroform (100 mL) was heated at reflux for 3.5 hours, at which point the reaction was deemed to be complete by LCMS. The mixture was allowed to cool to room temperature, and most of the chloroform was removed via rotary evaporator. The residue was taken up in ethyl acetate, and the solution was washed with saturated sodium bicarbonate, and brine, then dried over sodium sulfate and concentrated in vacuo. The residue purified using automated chromatography to provide the product (5.6 g, 82% yield). $^1$H NMR (400 MHz, CHLOROFORM-d) δ 7.61 (s, 1H), 2.69 (s, 3H), 2.65 (s, 3H). LC retention time 0.99 min [J]. MS (E+) m/z: 292 (MH$^+$).

Step 2

In a round-bottom reaction vessel equipped with a Teflon screw-cap and a magnetic stir-bar, a mixture of 7-bromo-2,4-bis(methylthio)imidazo[1,2-f][1,2,4]triazine (5.6 g, 19.23 mmol), Zinc cyanide (1.581 g, 13.46 mmol), and Zinc powder (0.252 g, 3.85 mmol) in 1-methyl-2-pyrrolidinone (NMP, 35 mL) was degassed with bubbling nitrogen for 5 minutes. The mixture was treated with bis(tri-t-butylphosphine)palladium (0) (0.421 g, 0.824 mmol), degassed for an additional 5 minutes, then the vial was sealed. The reaction was heated at 100° C. for 2 hours, then cooled to room temperature and stirred for 18 hours. The reaction mixture was filtered, and the filter cake was washed with dimethylformamide. The combined filtrate and washes were concentrated in vacuo, and the residue was purified using automated chromatography to provide the product (2.7 g, 59% yield). $^1$H NMR (400 MHz, DMSO-d$_6$) δ 8.43 (s, 1H), 2.68 (s, 3H), 2.62 (s, 3H). LC retention time 0.87 min [J]. MS (E+) m/z: 238 (MH$^+$).

Step 3

A solution of 2,4-bis(methylthio)imidazo[2,1-f][1,2,4]triazine-7-carbonitrile (208 mg, 0.877 mmol) in tetrahydrofuran (20 mL) was treated with 33% methanamine in ethanol (0.239 mL, 1.928 mmol) and the reaction was stirred at room temperature under nitrogen for 30 minutes. The mixture was diluted with water (10 mL) and stirring was continued for 10 minutes. The resulting solids were collected by filtration, rinsed with water followed by hexanes, then dried under vacuum to yield 4-(methylamino)-2-(methylthio)imidazo[2,1-f][1,2,4]triazine-7-carbonitrile (181 mg, 94% yield) as a pale yellow solid. $^1$H NMR (400 MHz, DMSO-d$_6$) δ 9.26 (br. s., 1H), 8.28 (s, 1H), 3.00 (s, 3H), 2.53 (s, 3H). LC retention time 0.71 min [J]. MS (E+) m/z: 221 (MH$^+$).

Step 4

A solution of 4-(methylamino)-2-(methylthio)imidazo[2,1-f][1,2,4]triazine-7-carbonitrile (151 mg, 0.686 mmol) in methylene chloride (3 mL) was treated with 3-chloroperbenzoic acid (158 mg, 0.686 mmol), and the reaction was stirred at room temperature for 20 minutes. The solvent was evaporated with a stream of nitrogen, and the residue was triturated with ethyl acetate. The resulting colorless solids were collected by filtration, rinsed with ethyl acetate, and dried under vacuum to yield 4-(methylamino)-2-(methylsulfinyl)imidazo[2,1-f][1,2,4]triazine-7-carbonitrile (120 mg, 74% yield). LC retention time 0.51 min [J]. MS (E+) m/z: 237 (MH$^+$).

Example 69

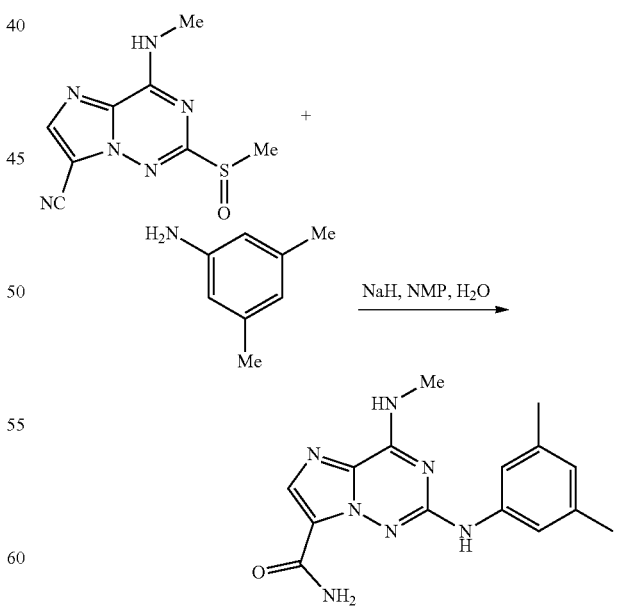

In a sealable reaction tube, a stirring solution of 4-(methylamino)-2-(methylsulfinyl)imidazo[2,1-f][1,2,4]triazine-7-carbonitrile (30 mg, 0.127 mmol) and 3,5-dimethylaniline (46.2 mg, 0.381 mmol) in wet 1-methyl-2-pyrrolidnone (NMP, 0.25 mL) was treated with 60% sodium hydride in mineral oil (50.8 mg, 1.270 mmol), and the mixture was stirred uncapped until gas evolution had ceased. The tube was capped, then placed into an aluminum reaction block which had been pre-heated to 135° C. The reaction was stirred for 30 minutes, at which point the contents of the tube had congealed into a dark-colored solid. The tube was cooled to room temperature, and the material was dissolved in 9:1 DMF/methanol (2 mL) and then purified using preparative LC, providing the title compound (5 mg, 13% yield). $^1$H NMR (500 MHz, DMSO-d$_6$) δ 9.16 (s, 1H), 8.82 (d, J=5.0 Hz, 1H), 8.26 (br. s., 1H), 8.04 (br. s., 1H), 7.95 (s, 1H), 7.84 (s, 1H), 7.21 (s, 2H), 6.62 (s, 1H), 3.03 (d, J=5.0 Hz, 3H), 2.24 (s, 6H). LC retention time 1.44 min [E]. MS (E+) m/z: 312 (MH$^+$).

The following Examples were prepared in a similar manner to the product of Example 69.

| Example number | R | Ar | Rt (min) [Method] | m/z [M + H]$^+$ |
|---|---|---|---|---|
| 70 | cyclopropyl | 3,5-dimethylphenyl | 1.59 [E] | 338 |
| 71 | cyclopropyl | 3-fluoro-5-methylphenyl | 0.82 [J] | 342 |
| 73 | Me | 3-fluoro-5-methylphenyl | 1.37 [E] | 316 |
| 74 | Me | 2-methoxyphenyl | 1.24 [E] | 314 |

Preparation 9

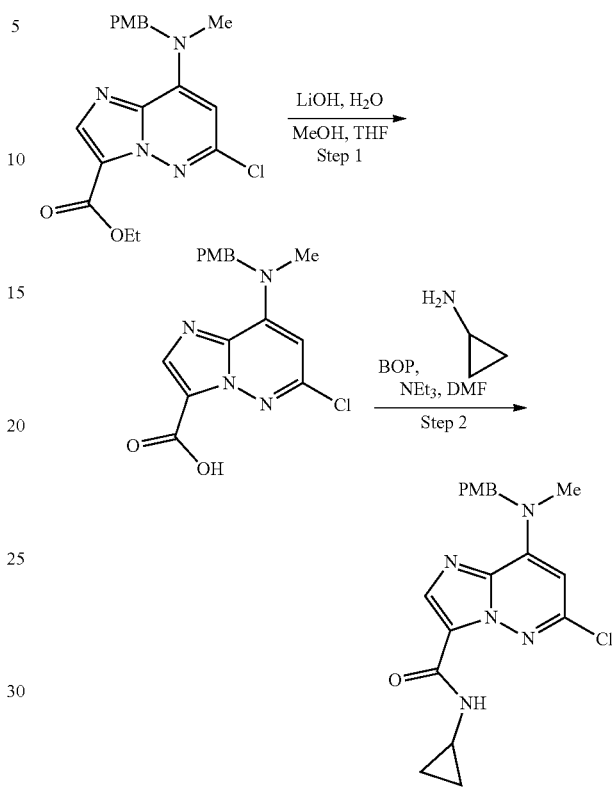

Step 1

To a solution of ethyl 6-chloro-8-((4-methoxybenzyl)(methyl)amino)imidazo[1,2-b]pyridazine-3-carboxylate (1.20 g, 3.20 mmol) in methanol (15 mL) and tetrahydrofuran (15 mL) was added 0.5 M (aqueous) lithium hydroxide (25.6 mL, 12.81 mmol) and the reaction was stirred overnight. The reaction was diluted with water and then the methanol was removed in vacuo, the resulting solution was adjusted to pH ~4 using hydrochloric acid (1 M aqueous) the product was extracted with dichloromethane and the combined organic layers were dried over sodium sulfate, filtered, and concentrated to provide the acid (1.00 g, 81% yield), which was used without further purification. LC retention time 0.90 min [J]. MS (E+) m/z: 347 (MH$^+$).

Step 2

A mixture of 6-chloro-8-((4-methoxybenzyl)(methyl)amino)imidazo[1,2-b]pyridazine-3-carboxylic acid (536 mg, 1.546 mmol), cyclopropanamine (0.321 mL, 4.64 mmol), and triethylamine (0.646 mL, 4.64 mmol) in dimethylformamide (3 mL) was treated with (benzotriazol-1-yloxy)tris(dimethylamino)phosphonium hexafluorophosphate (BOP, 752 mg, 1.700 mmol), and the reaction was stirred at room temperature for 5 hours. The desired product was precipitated with water (5 mL), and collected by filtration. The solids were rinsed twice with water, once with a small amount of methanol, and dried under vacuum to yield 6-chloro-N-cyclopropyl-8-((4-methoxybenzyl)(methyl)amino)imidazo[1,2-b]pyridazine-3-carboxamide (480 mg, 80% yield). $^1$H NMR (400 MHz, DMSO-d$_6$) δ 8.55 (d, J=3.5 Hz, 1H), 8.06 (s, 1H), 7.19 (d, J=8.6 Hz, 2H), 6.89 (d, J=8.8 Hz, 2H), 6.39 (s, 1H), 5.52 (br. s., 2H), 3.73 (s, 3H), 3.31 (s, 3H), 2.88 (tq, J=7.2, 3.8 Hz, 1H), 0.89-0.75 (m, 2H), 0.63-0.51 (m, 2H). LC retention time 1.04 min [J]. MS (E+) m/z: 386 (MH$^+$).

Example 75

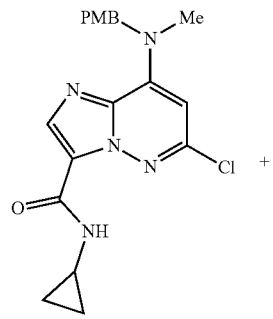

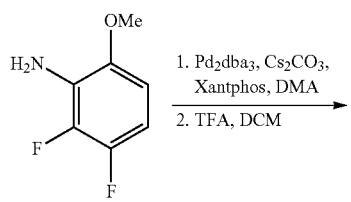

1. Pd$_2$dba$_3$, Cs$_2$CO$_3$, Xantphos, DMA
2. TFA, DCM

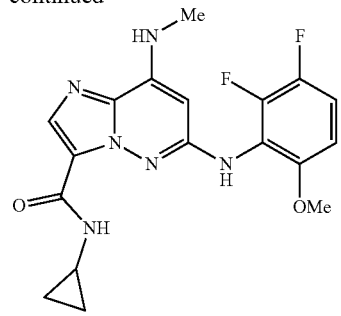

In a sealable vial, a mixture of 6-chloro-N-cyclopropyl-8-((4-methoxybenzyl)(methyl)amino)imidazo[1,2-b]pyridazine-3-carboxamide (50 mg, 0.130 mmol), 2,3-difluoro-6-methoxyaniline (41.2 mg, 0.259 mmol), and cesium carbonate (169 mg, 0.518 mmol) was degassed with bubbling nitrogen. After 5 minutes, Xantphos (30.0 mg, 0.052 mmol) and Pd$_2$(dba)$_3$ (23.73 mg, 0.026 mmol) were added, and degassing was continued for 5 minutes. The vial was capped, and the reaction was heated at 100° C. for 1 hour, and then allowed to come to room temperature. The reaction was diluted with ethyl acetate (20 mL) and filtered, the filtrate was washed twice with water, and once with 10% lithium chloride solution, then dried over sodium sulfate and concentrated in-vacuo. The residue was taken up in dichloromethane (1 mL) and then treated with trifluoroacetic acid (0.5 mL, 6.49 mmol). The reaction was stirred at room temperature for 40 minutes and then concentrated in vacuo. The crude product was then purified using preparative LC to provide the title compound (8.3 mg, 16% yield). $^1$H NMR (500 MHz, METHANOL-d$_4$) δ 7.91 (s, 1H), 7.11 (q, J=9.4 Hz, 1H), 6.80 (ddd, J=9.4, 4.0, 2.0 Hz, 1H), 5.91 (s, 1H), 3.86 (s, 3H), 3.03 (s, 3H), 2.72 (tt, J=7.3, 3.8 Hz, 1H), 0.74-0.65 (m, 2H), 0.32-0.19 (m, 2H). LC retention time 1.72 min [E]. MS (E+) m/z: 389 (MH$^+$).

The following Examples were prepared in a similar manner to the product of Example 75.

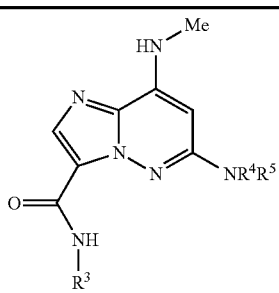

| Ex. No. | R$^3$ | NR$^4$R$^5$ | Reaction temperature (° C.)/time (hour) | Rt (min) [Method] | m/z [M + H]$^+$ |
|---|---|---|---|---|---|
| 76 | cyclopropyl | N(Me)(Ph) | 125/5 | | |
| 77 | cyclopropyl | NH(2-OMe-phenyl) | 130/1 | 1.53 [E] | 353 |

-continued

| Ex. No. | R³ | NR⁴R⁵ | Reaction temperature (° C.)/time (hour) | Rt (min) [Method] | m/z [M + H]⁺ |
|---|---|---|---|---|---|
| 78 | cyclopropyl | indolin-1-yl | 125/5 | | |
| 79 | cyclopropyl | 3,5-difluoro-2-methoxyphenyl-NH- | 100/1 | 1.77 [E] | 389 |
| 80 | -C(Me)₂-OH | 2-methoxyphenyl-NH- | 90/1 | 1.32 [E] | 385 |
| 81 | -C(Me)₂-OH | 3,5-difluoro-2-methoxyphenyl-NH- | 90/1 | 1.45 [E] | 421 |
| 82 | -C(Me)₂-OH | 2,3-dihydro-1,4-benzodioxin-5-yl-NH- | 125/40 min | 1.86 [E] | 413 |
| 83 | H | 3,5-difluoro-2-methoxyphenyl-NH- | 125/1 | 1.31 [E] | 349 |
| 84 | cyclopropyl | 2,3-dihydro-1,4-benzodioxin-5-yl-NH- | 125/40 min | 1.94 [E] | 381 |

-continued
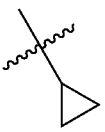 [SMILES: *C1CC1]
| Ex. No. | R³ | NR⁴R⁵ | Reaction temperature (° C.)/time (hour) | Rt (min) [Method] | m/z [M + H]⁺ |
|---|---|---|---|---|---|
| 85 | 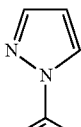 | 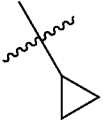 | 125/4 | 0.79 [J] | 390 |
| 86 | 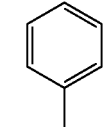 | 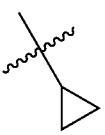 [SMILES: *C1CC1] | 125/4 | 0.85 [J] | 400 |
| 87 | 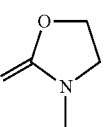 |  | 125/2 | 0.72 [J] | 409 |
| 88 | 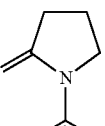 | 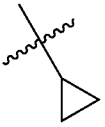 | 110/overnight | 0.72 [J] | 407 |
| 89 | 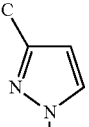 | | 110/overnight | 0.95 [J] | 458 |

-continued

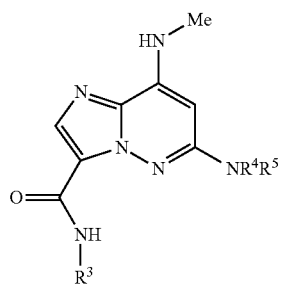

| Ex. No. | R³ | NR⁴R⁵ | Reaction temperature (° C.)/time (hour) | Rt (min) [Method] | m/z [M + H]⁺ |
|---|---|---|---|---|---|
| 90 | cyclopropyl-CH | 3-hydroxy-2-oxopyrrolidin-1-yl pyridin-2-yl-NH | 110/overnight | 0.65 [J] | 423 |
| 91 | cyclopropyl-CH | 5-hydroxy-pyrazolidin-1-yl pyridin-2-yl-NH | 110/overnight | 0.77 [J] | 406 |
| 92 | cyclopropyl-CH | 2-(pyrazol-1-yl)pyridin-3-yl-NH | 125/2 | 1.52 [E] | 390 |
| 93 | cyclopropyl-CH | 5-methoxypyridin-3-yl-NH | 125/2 | 1.12 [E] | 354 |
| 94 | cyclopropyl-CH | 2-methoxypyridin-3-yl-NH | 125/2 | 1.24 [E] | 354 |
| 95 | cyclopropyl-CH | 2-fluoropyridin-3-yl-NH | 125/2 |  | 342 |

-continued

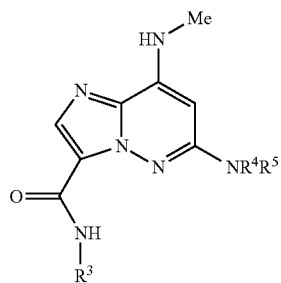

| Ex. No. | R³ | NR⁴R⁵ | Reaction temperature (° C.)/time (hour) | Rt (min) [Method] | m/z [M + H]⁺ |
|---|---|---|---|---|---|
| 96 | cyclopropyl | 5-methyl-pyridin-3-yl-NH- | 125/2 | | 338 |
| 97 | cyclopropyl | 2-methyl-pyridin-3-yl-NH- | 125/2 | | |
| 98 | cyclopropyl | 2-(pyrazol-1-yl)pyridin-3-yl-NH- | 125/8 | 0.68 [J] | 391 |
| 99 | cyclopropyl | 2-(3-trifluoromethyl-pyrazol-1-yl)pyridin-3-yl-NH- | 125/4 | 0.92 [J] | 458 |
| 100 | cyclopropyl | 2-(3-methyl-5-trifluoromethyl-pyrazol-1-yl)pyridin-3-yl-NH- | 125/4 | 0.86 [J] | 472 |
| 101 | cyclopropyl | 2-(3-methyl-pyrazol-1-yl)pyridin-3-yl-NH- | 125/4 | 0.79 [J] | 404 |

| Ex. No. | R³ | NR⁴R⁵ | Reaction temperature (° C.)/time (hour) | Rt (min) [Method] | m/z [M + H]⁺ |
|---|---|---|---|---|---|
| 102 | cyclopropyl | 5-methyl-pyrazolyl-pyridinyl-NH | 125/4 | 0.90 [J] | 391 |

Example 103

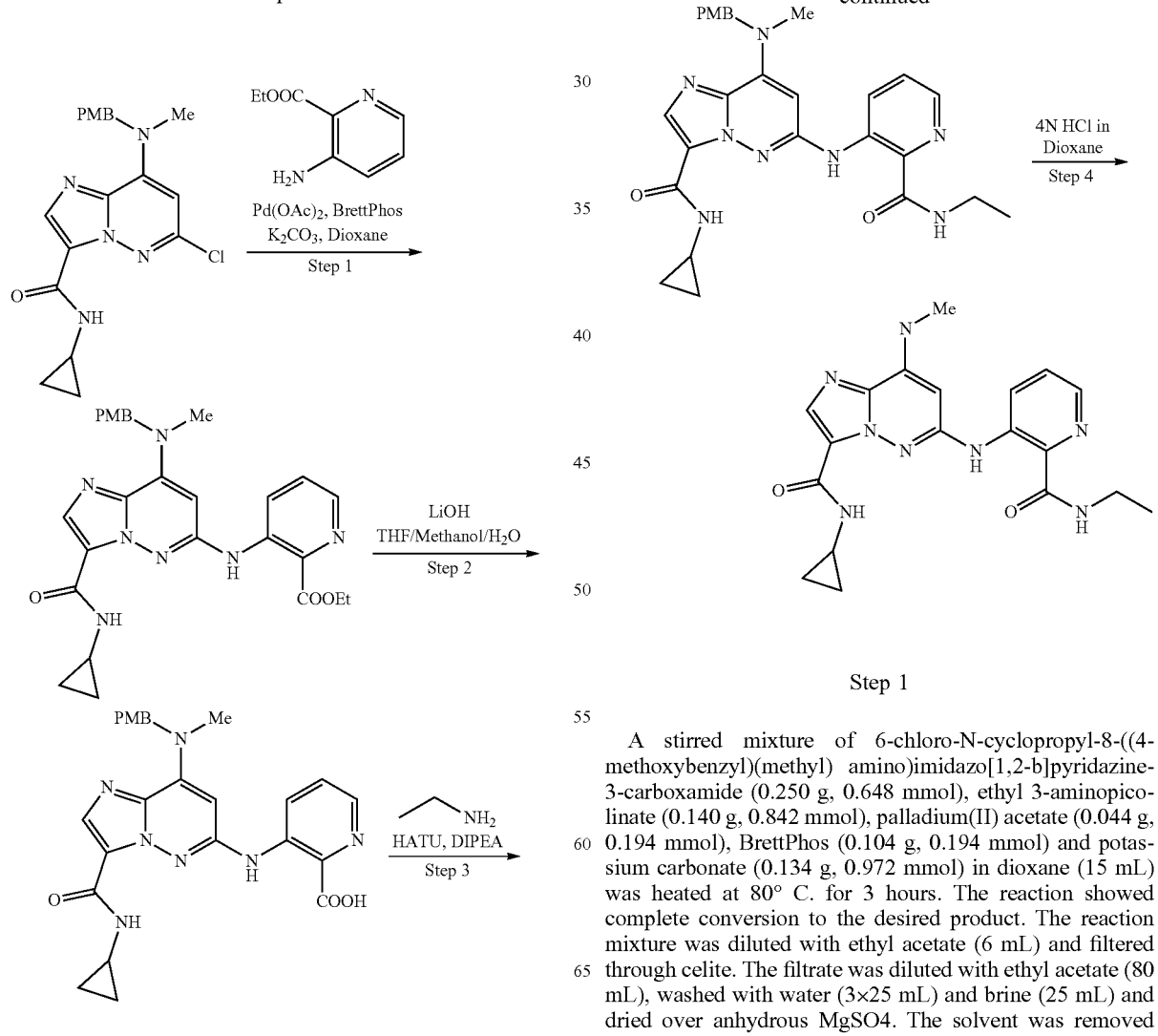

Step 1

A stirred mixture of 6-chloro-N-cyclopropyl-8-((4-methoxybenzyl)(methyl) amino)imidazo[1,2-b]pyridazine-3-carboxamide (0.250 g, 0.648 mmol), ethyl 3-aminopicolinate (0.140 g, 0.842 mmol), palladium(II) acetate (0.044 g, 0.194 mmol), BrettPhos (0.104 g, 0.194 mmol) and potassium carbonate (0.134 g, 0.972 mmol) in dioxane (15 mL) was heated at 80° C. for 3 hours. The reaction showed complete conversion to the desired product. The reaction mixture was diluted with ethyl acetate (6 mL) and filtered through celite. The filtrate was diluted with ethyl acetate (80 mL), washed with water (3×25 mL) and brine (25 mL) and dried over anhydrous MgSO4. The solvent was removed under vacuum to give the product as an orange solid (0.33 g, 99% yield). LC retention time 0.93 min [J]. MS (E+) m/z: 516 (MH$^+$).

Step 2

Lithium hydroxide monohydrate (0.159 g, 3.78 mmol) dissolved in water (3.64 mL) was quickly added to a stirred mixture of ethyl 3-((3-(cyclopropylcarbamoyl)-8-((4-methoxybenzyl)(methyl)amino)imidazo[1,2-b]pyridazin-6-yl)amino)picolinate (0.390 g, 0.756 mmol) in THF (8 mL) and methanol (4.0 mL) at room temperature. The resulting mixture was stirred at room temperature overnight. The starting material was completely converted to the desired product. The reaction mixture was concentrated, then acidified with 1N HCl solution, and filtered to give a tan solid (0.21 g, 56.9% yield). LC retention time 0.74 min [J]. MS (E+) m/z: 488 (MH$^+$).

Steps 3 & 4

3-((3-(cyclopropylcarbamoyl)-8-((4-methoxybenzyl) (methyl)amino)imidazo[1,2-b]pyridazin-6-yl)amino)picolinic acid (12.5 mg, 0.026 mmol) was dissolved in DMF (2.7 mL). Ethylamine (1.73 mg, 0.038 mmol) HATU (14.62 mg, 0.038 mmol), DIPEA (13.43 μL, 0.077 mmol) were added to the DMF solution. The reaction was stirred at room temperature. After the reaction was completed, the reaction samples were blown down in the Zymark tabletop dryer at 45° C. overnight to give a crude product. Dichloromethane (500 μL) and 4N HCl in dioxane (200 μL, 0.026 mmol) were subsequently added. The reactions was stirred at room temperature for 1 hour. The reaction sample was blown down in the Zymark tabletop dryer at 45° C. for 1 hour. Crude sample was purified with prep HPLC to provide the desired compound (3.0 mg, 27.9% yield, 94% purity). LC retention time 1.49 min [E]. MS (E+) m/z: 395 (MH$^+$). $^1$H NMR (500 MHz, DMSO-d$_6$) δ 11.48 (s, 1H), 9.16 (s, 1H), 8.64 (d, J=9.2 Hz, 1H), 8.49 (d, J=3.7 Hz, 1H), 8.24 (d, J=4.3 Hz, 1H), 7.87 (s, 1H), 7.62 (d, J=7.3 Hz, 2H), 5.88 (s, 1H), 3.16 (d, J=4.9 Hz, 2H), 2.91 (d, J=4.9 Hz, 3H), 2.86 (dd, J=7.3, 3.7 Hz, 1H), 1.14 (t, J=7.0 Hz, 3H), 0.79-0.72 (m, 2H), 0.45 (br. s., 2H)

The following Examples were prepared in a similar manner to the product of Example 103.

| Example number | NHR | Rt (min) [Method] | m/z [M + H]$^+$ |
|---|---|---|---|
| 104 | H$_2$N-CH(CH$_3$)- |  | 381 |
| 105 | H$_2$N-CH(CH$_2$)-C(CH$_3$)$_3$ |  | 437 |
| 106 | H$_2$N-CH(CH$_2$)-(tetrahydrothiophene-1,1-dioxide) | 1.22 [E] | 485 |
| 107 | H$_2$N-CH(CH$_2$)-CH$_2$F | 1.47 [E] | 413 |
| 108 | H$_2$N-CH(CH$_2$)-CH$_2$OCH$_3$ | 1.48 [E] | 425 |

Preparation 10

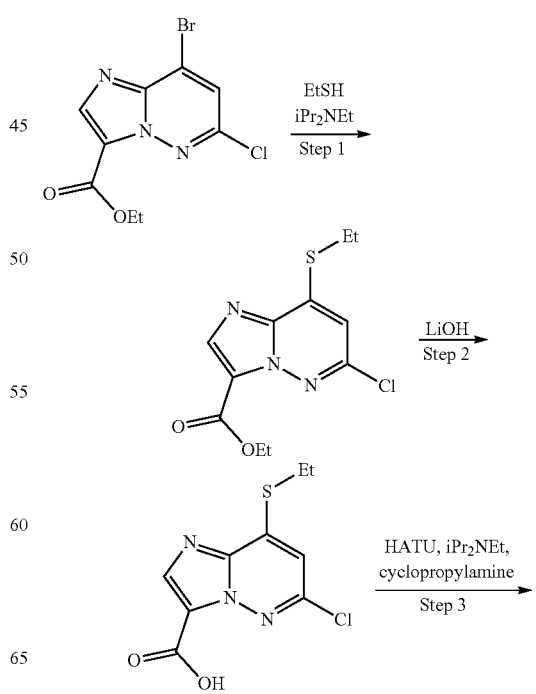

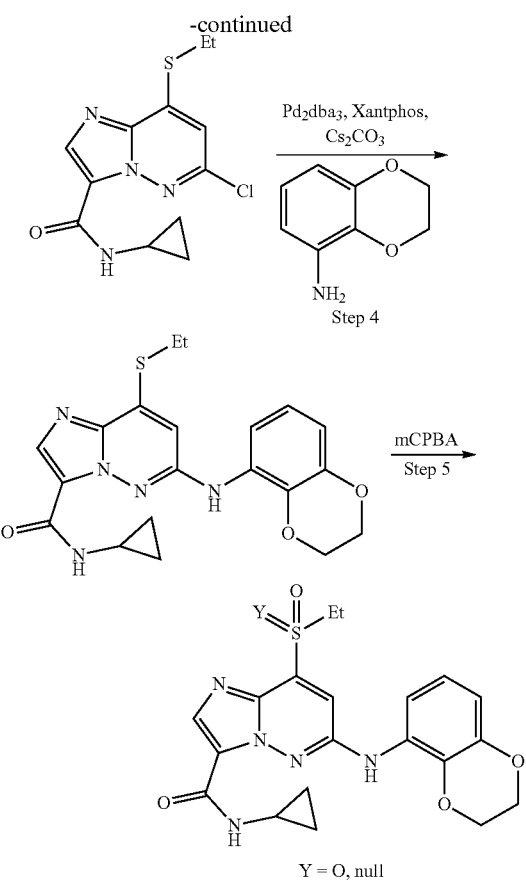

Step 1

To a suspension of ethyl 8-bromo-6-chloroimidazo[1,2-b]pyridazine-3-carboxylate (3 g, 9.85 mmol) in tetrahydrofuran (21 mL) was added triethylamine (13.73 mL, 99 mmol), followed by ethanethiol (0.729 mL, 9.85 mmol). The mixture was heated to 50° C. overnight and then concentrated under a stream of nitrogen. The crude product was suspended in hexanes and filtered, rinsing with hexanes. The powder was collected and then triturated with ethyl acetate, the suspension was then filtered collected and concentrating the filtrate to provide the intermediate product (2.19 g, 75% yield). $^1$H NMR (400 MHz, CHLOROFORM-d) δ 8.25 (s, 1H), 6.90 (s, 1H), 4.45 (q, J=7.1 Hz, 2H), 3.17 (q, J=7.5 Hz, 2H), 1.52 (t, J=7.5 Hz, 3H), 1.43 (t, J=7.2 Hz, 3H). LC retention time 0.90 min [J]. MS (E+) m/z: 286 (MH$^+$).

Step 2

To a solution of ethyl 6-chloro-8-(ethylthio)imidazo[1,2-b]pyridazine-3-carboxylate (1.3 g, 4.55 mmol) in tetrahydrofuran (12 mL) and methanol (12 mL) was added lithium hydroxide (3M aq.) (12 ml, 36.0 mmol) and the reaction was stirred at room temperature for 3 minutes. The reaction was diluted with water, acidified, extracted with dichloromethane, dried over sodium sulfate, filtered, concentrated and carried on.

Step 3

The crude product from Step 2 was combined with cyclopropylamine (0.64 mL, 9.10 mmol), and diisopropylethylamine (4 mL, 23 mmol), next 1-[bis(dimethylamino)methylene]-1H-1,2,3-triazolo[4,5-b]pyridinium 3-oxid hexafluorophosphate (HATU, 2.08 g, 5.46 mmol) was added and the reaction was stirred at room temperature for 2 hours. The reaction was diluted with ethyl acetate (500 mL) and then washed with water three times, and once with saturated sodium chloride. The organic layer was dried over sodium sulfate, filtered, concentrated and purified by automated chromatography to provide the amide (800 mg, 59% yield). LC retention time 0.82 min [J]. MS (E+) m/z: 297 (MH$^+$).

Step 4

To a solution of dimethylacetamide (DMA, 15 mL) containing 6-chloro-N-cyclopropyl-8-(ethylthio)imidazo[1,2-b]pyridazine-3-carboxamide (800 mg, 2.70 mmol) and 2,3-dihydrobenzo[b][1,4]dioxin-5-amine (815 mg, 5.39 mmol) was added Pd$_2$(dba)$_3$ (247 mg, 0.270 mmol), Xantphos (312 mg, 0.539 mmol) and cesium carbonate (3513 mg, 10.78 mmol) in a single portion. The vessel was evacuated and backfilled with nitrogen (×3), sealed and heated to 125° C. and stirred overnight. It was observed that dimethylamine (perhaps from DMA decomposition) was adding competitively with the aniline. The reaction was cooled to room temperature and diluted with ethyl acetate (500 mL) and then washed with water three times. The organic layer was dried over sodium sulfate, filtered, concentrated and purified using automated chromatography (twice). The resulting product (200 mg, 69% pure, 12% yield) contained a significant amount of an impurity (31% by HPLC, MS (MH$^+$) =306). LC retention time 2.52 min [A]. MS (E+) m/z: 412 (MH$^+$).

Step 5

To a solution of N-cyclopropyl-6-((2,3-dihydrobenzo[b][1,4]dioxin-5-yl)amino)-8-(ethylthio)imidazo[1,2-b]pyridazine-3-carboxamide (200 mg, 0.486 mmol) in dichloromethane (24 mL) was added 3-chloroperbenzoic acid (mCPBA, 218 mg, 0.972 mmol). After 15 minutes the reaction was concentrated providing a complicated mixture of the sulfone and the sulfoxide of the starting material along with several impurities. The crude mixture was carried on as recovered.

Example 109

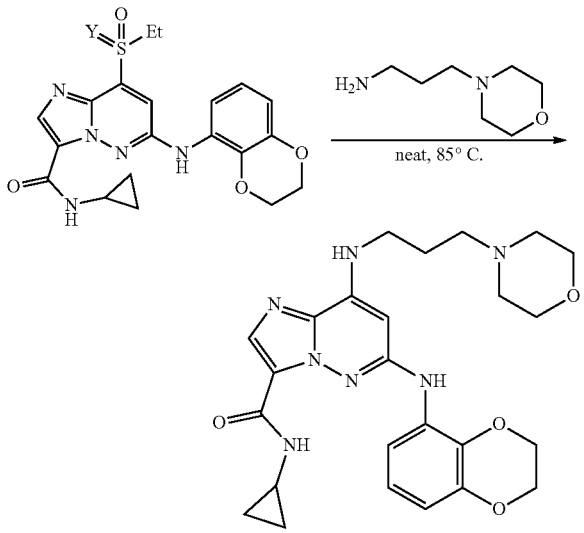

To the mixture of intermediates (30 mg, ~0.07 mmol) obtained from Preparation 10 was added 3-morpholinopropan-1-amine (154 μL, 1.053 mmol) and the reaction was heated to 80° C. After 1 hour the reaction was cooled to room temperature, dissolved in methanol and purified using preparative LC to provide the title compound (5.1 mg). $^1$H NMR (500 MHz, METHANOL-$d_4$) δ 7.96 (s, 1H), 7.24 (d, J=7.4 Hz, 1H), 6.88 (t, J=7.9 Hz, 1H), 6.68 (dd, J=8.4, 1.0 Hz, 1H), 5.93 (s, 1H), 4.40-4.28 (m, 4H), 3.83-3.74 (m, 5H), 3.41 (t, J=6.7 Hz, 2H), 2.89-2.81 (m, 1H), 2.63-2.47 (m, 5H), 1.95 (t, J=6.9 Hz, 2H), 0.86-0.74 (m, 2H), 0.55-0.39 (m, 2H). LC retention time 1.55 min [E]. MS (E+) m/z: 494 (MH$^+$).

Example 110 was prepared in a manner analogous to 109:

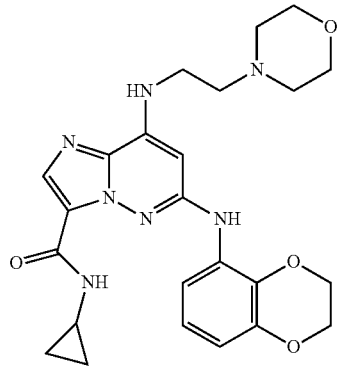 [SMILES: O=C(NC1CC1)c1cnc2c(NCCN3CCOCC3)cc(Nc3cccc4c3OCCO4)nn12]

$^1$H NMR (500 MHz, METHANOL-$d_4$) δ 7.93 (s, 1H), 7.19 (dd, J=8.2, 1.2 Hz, 1H), 6.85 (t, J=8.2 Hz, 1H), 6.65 (dd, J=8.2, 1.2 Hz, 1H), 5.93 (s, 1H), 4.37-4.24 (m, 4H), 3.80-3.70 (m, 4H), 3.41 (t, J=6.4 Hz, 2H), 2.89-2.79 (m, 1H), 2.73 (t, J=6.4 Hz, 2H), 2.55 (br. s., 4H), 0.81-0.71 (m, 2H), 0.48-0.36 (m, 2H). LC retention time 1.38 min [E]. MS (E+) m/z: 480 (MH$^+$).

Preparation 11

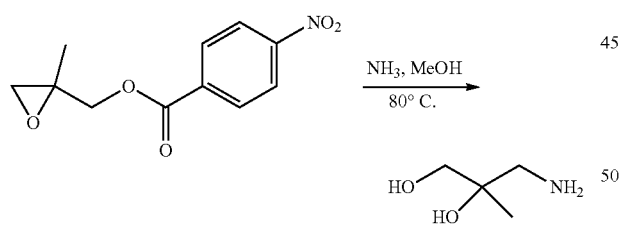

A 250 mL steel bomb reaction vessel was loaded with (2-methyloxiran-2-yl)methyl 4-nitrobenzoate (both enantiomers available from Aldrich®) (2.1 g, 8.85 mmol) in methanol (50 mL) to this was added ammonia (7 M in MeOH, 70 mL, 70 mmol). The vessel was sealed and heated to 80° C. for 3 hours and then stirred at 50° C. for 18 hours. The reaction was cooled to room temperature, concentrated and then taken up in 10 mL of MeOH. The suspension was cooled in a refrigerator for 1 hour and then filtered to remove residual solid. The filtrate was concentrated to provide the crude product as an amber oil (contains about 0.5 eq. of the 4-nitrobenzamide as a byproduct). Yield not determined, material used as is. (NMR omits impurity peaks for clarity) $^1$H NMR (400 MHz, CHLOROFORM-d) δ 3.64 (d, J=11.0 Hz, 1H), 3.49 (dd, J=11.0, 1.0 Hz, 1H), 2.88-2.75 (m, 2H), 1.10 (s, 3H). Not visible by UV or MS.

Preparation 12

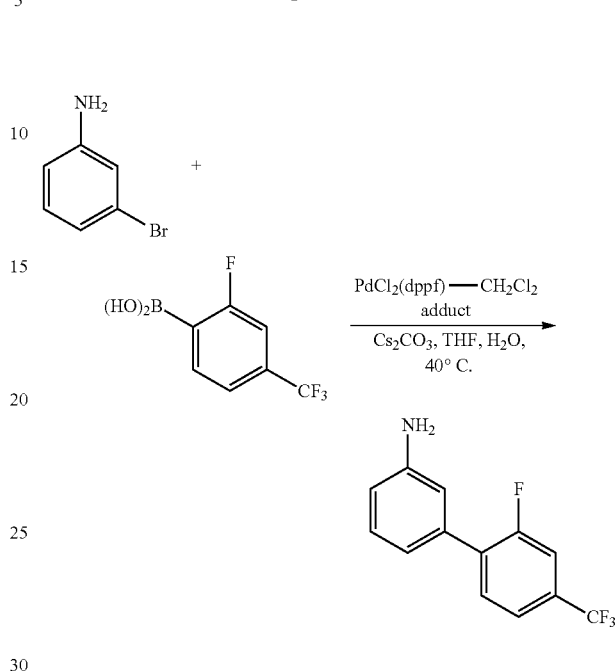

3-Bromoaniline (400 mg, 2.32 mmol), (2-fluoro-4-(trifluoromethyl)phenyl)boronic acid (483 mg, 2.32 mmol) and cesium carbonate (1.5 g, 4.65 mmol) were combined in THF (8 mL) and water (2 mL) and then degassed by sparging with nitrogen gas for 5 minutes. [1,1'-Bis(diphenylphosphino)ferrocene]dichloropalladium(II), complex with dichloromethane (190 mg, 0.23 mmol) was added and the reaction was heated to 40° C. for 1 hour. Water was added to the reaction and the product was extracted (×2) with dichloromethane. The combined organic layers were dried over sodium sulfate, filtered and concentrated. The crude product was purified using silica gel chromatography (9:1-3:1-1:1 hexanes:EtOAc) to give 2'-fluoro-4'-(trifluoromethyl)-[1,1'-biphenyl]-3-amine (500 mg, 1.763 mmol) as an amber oil). LC retention time 0.81 min [J]. MS (E+) m/z: 256 (MH$^+$).

Example 111

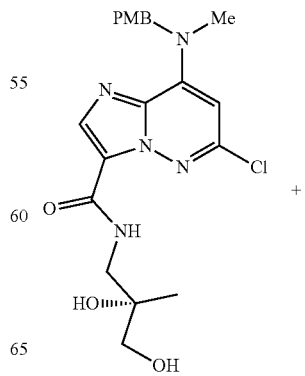

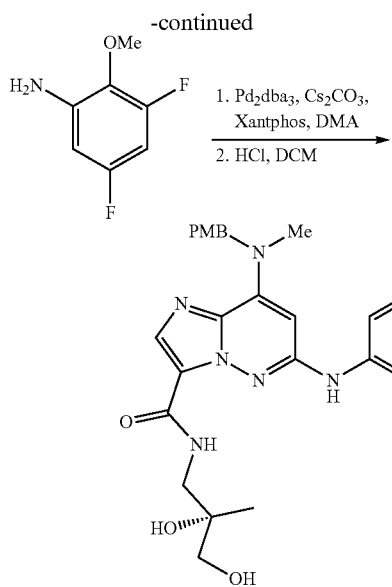

(S)-6-Chloro-N-(2,3-dihydroxy-2-methylpropyl)-8-((4-methoxybenzyl) (methyl)amino)imidazo[1,2-b]pyridazine-3-carboxamide (60 mg, 0.14 mmol), prepared in a manner analogous to Example 1, was combined with 3,5-difluoro-2-methoxyaniline (44 mg, 0.28 mmol) and cesium carbonate (180 mg, 0.55 mmol) in DMA (2 mL). The reaction was degassed with bubbling nitrogen for 5 minutes and then Xantphos (32 mg, 0.055 mmol) and $Pd_2dba_3$ (25 mg, 0.028 mmol) were added. The reaction was sealed and heated to 90° C. for one hour. The reaction was diluted with DMF (3 mL) and filtered. The filtrate was concentrated in vacuo and then purified using automated chromatography to give the protected intermediate (LC retention time 0.94 [J], MS (E+) m/z: 557 ($MH^+$)). The intermediate was dissolved in DCM (2 mL) and treated with HCl (4 M in dioxane, 1 mL, 4.0 mmol). The reaction was stirred at room temperature for 1 hour and then concentrated and purified using automated chromatography with a 10%-100% gradient of eluent A:eluent B (eluent A=1 part 10% ammonium hydroxide in MeOH+9 parts DCM; eluent B=0.3 parts 10% ammonium hydroxide in MeOH+9.7 parts DCM) to give Example 111 (23 mg, 0.051 mmol). $^1$H NMR (400 MHz, DMSO-$d_6$) δ 8.73 (t, J=6.4 Hz, 1H), 8.69 (s, 1H), 7.88 (s, 1H), 7.66 (dt, J=11.2, 2.4 Hz, 1H), 7.55 (q, J=4.8 Hz, 1H), 6.90 (ddd, J=11.6, 8.7, 3.1 Hz, 1H), 6.23 (s, 1H), 3.83 (d, J=0.7 Hz, 3H), 3.42-3.32 (m, 2H), 3.14-3.09 (m, 2H), 2.90 (d, J=4.8 Hz, 3H), 0.91 (s, 3H). LC retention time (achiral) 0.74 min [J]. MS (E+) m/z: 437 ($MH^+$). 96.6% ee [AD-H (0.46×25 cm), 25% MeOH w 0.1% DEA in CO2, 3 ml/min, 35 C, 100 bars BPR, 220 nm] major @5.06 min minor @7.34 min. Assignment based on synthesis (aminolysis of commercial S-2-methylglycidyl 4 nitrobenzoate).

The following Examples were prepared in a similar manner to the product of Example 111

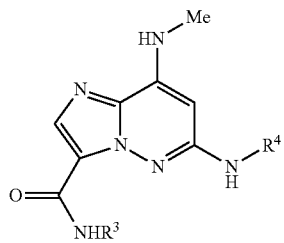

| Ex. No | $R^3$ | $R^4$ | Rt (min) [Method] | m/z $[M + H]^+$ |
|---|---|---|---|---|
| 112 | HO, OH with Me | 2,3,4-trifluorophenyl | 1.15 [E] | 443 |
| 113 | HO, OH with Me | 2'-fluoro-4'-(CF3)-biphenyl-3-yl | 1.75 [E] | 533 |
| 114 | cyclopropyl | 3,5-dimethylphenyl | 1.66 [E] | 351 |

-continued

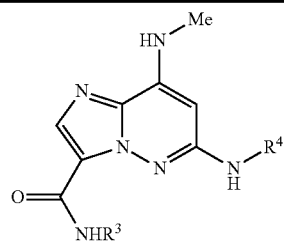

| Ex. No | R³ | R⁴ | Rt (min) [Method] | m/z [M + H]⁺ |
|---|---|---|---|---|
| 115 | Me, with CH₂OH and CH₂OH, Me | 3,5-dimethylphenyl | 1.36 [E] | 413 |
| 116 | cyclopropyl | 3-(2-fluoro-4-trifluoromethylphenyl)phenyl | 2.05 [E] | 485 |
| 117 | H | 3-tBu-phenyl | 2.11 [E] | 339 |
| 118 | 2-fluorocyclopropyl | 3-(2-fluoro-4-trifluoromethylphenyl)phenyl | 2.00 [E] | 503 |

Preparation 13

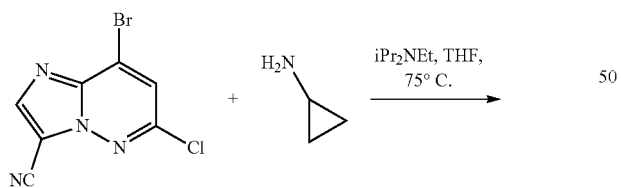

To a solution of 8-bromo-6-chloroimidazo[1,2-b]pyridazine-3-carbonitrile (from Preparation 4, 20 mg, 0.09 mmol) in THF (0.5 mL) was added cyclopropanamine (6.5 mg, 0.11 mmol) and diisopropylethylamine (0.025 mL, 0.14 mmol). The reaction was heated to 75° C. for 6 hours and then diluted with water. The product was extracted (×2) with EtOAc, washed with brine solution, dried over sodium sulfate, filtered and concentrated to provide 6-chloro-8-(cyclopropylamino)imidazo[1,2-b]pyridazine-3-carbonitrile (17 mg, 0.069 mmol). ¹H NMR (400 MHz, DMSO-d₆) δ 8.73 (s, 1H), 8.36 (s, 1H), 2.68 (m, 1H), 0.86 (m, 2H), 0.68 (m, 2H). LC retention time 2.98 min [C]. MS (E+) m/z: 234 (MH⁺).

Example 119

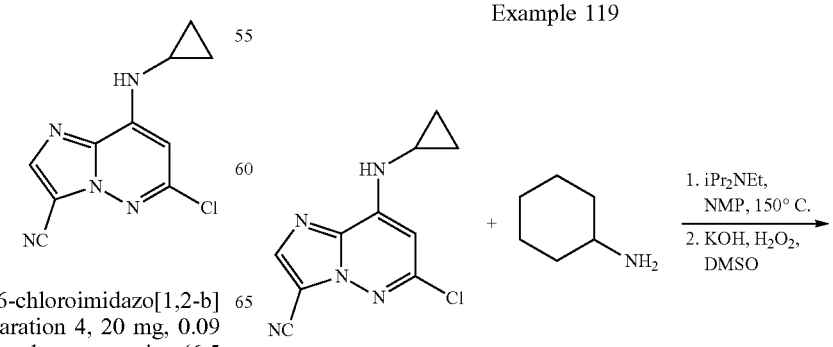

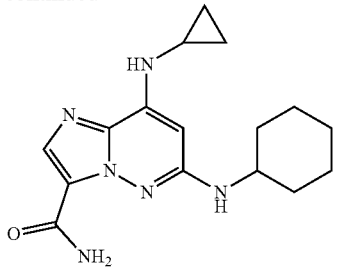

6-Chloro-8-(cyclopropylamino)imidazo[1,2-b]pyridazine-3-carbonitrile (100 mg, 0.428 mmol), cyclohexanamine (424 mg, 4.28 mmol), iPr$_2$NEt (0.747 mL, 4.28 mmol) and NMP (1 mL) were taken in a 10 ml micro wave tube and heated to 150° C. overnight. The reaction was diluted with water and extracted (×3) with ethyl acetate, the combined organics were washed with water and brine, dried over sodium sulfate, filtered, concentrated and purified via automated chromatography to provide 6-(cyclohexylamino)-8-(cyclopropylamino)imidazo[1,2-b]pyridazine-3-carbonitrile. This was dissolved in DMSO (1 mL) and KOH (5M, 1 mL, 5 mmol) was added followed by the dropwise addition of H$_2$O$_2$ (30% aq., 0.5 mL, 4.9 mmol). The reaction was stirred at room temperature for 2 hours and then diluted with ethyl acetate, washed with water (×2) and brine. The organic layer was dried over sodium sulfate, filtered, concentrated and purified using preparative LC to provide Example 119 (15 mg, 11% yield over two steps). $^1$H NMR (400 MHz, DMSO-d$_6$) δ 8.52 (s, 1H), 7.83 (s, 1H), 7.78 (br. s., 1H), 7.36 (br. s., 1H), 6.85 (br. s., 1H), 6.00 (s, 1H), 3.48 (m, 1H), 1.99 (m, 2H), 1.75 (m, 2H), 1.61 (m, 1H), 1.37-1.20 (m, 6H), 0.79 (m, 2H), 0.62 (m, 2H). LC retention time 8.11 min [Q] MS (E+) m/z: 315 (MH$^+$).

| | $^1$H NMR (METHANOL-d4 equates CDCl$_3$:MeOD ~1:1 unless otherwise Compound noted) |
|---|---|
| 2 | $^1$H NMR (400 MHz, DMSO-d$_6$) δ 9.19 (s, 1H), 8.66 (d, J = 3.7 Hz, 1H), 7.83 (s, 1H), 7.51 (d, J = 4.8 Hz, 1H), 7.16 (d, J = 11.2 Hz, 1H), 6.97 (s, 1H), 6.67 (d, J = 9.7 Hz, 1H), 5.74 (s, 1H), 2.87 (d, J = 4.6 Hz, 3H), 2.84 (dt, J = 7.3, 3.6 Hz, 1H), 2.32 (s, 3H), 0.75-0.67 (m, 2H), 0.43-0.37 (m, 2H). *Note compound was isolated as the TFA salt. |
| 3 | $^1$H NMR (500 MHz, DMSO-d$_6$) δ 9.20 (s, 1H), 7.84 (d, J = 12.4 Hz, 1H), 7.66 (s, 1H), 7.33 (q, J = 4.8 Hz, 1H), 7.25 (s, 1H), 6.54 (d, J = 9.4 Hz, 1H), 5.74 (s, 1H), 4.31-3.99 (m, 4H), 2.86 (d, J = 5.0 Hz, 3H), 2.30 (s, 3H), 2.25 (quin, J = 7.7 Hz, 2H) |
| 4 | $^1$H NMR (500 MHz, METHANOL-d$_4$) δ 9.00 (d, J = 6.9 Hz, 1H), 7.98 (s, 1H), 7.73 (dt, J = 10.9, 2.0 Hz, 1H), 7.31 (s, 1H), 7.01 (d, J = 8.4 Hz, 1H), 5.84 (s, 1H), 4.57-4.44 (m, 1H), 3.04 (s, 3H), 2.43-2.28 (m, 2H), 1.96-1.85 (m, 2H), 1.81-1.67 (m, 2H) |
| 5 | $^1$H NMR (500 MHz, DMSO-d$_6$) δ 9.39 (s, 1H), 8.75 (d, J = 7.9 Hz, 1H), 7.83 (s, 1H), 7.59 (d, J = 5.4 Hz, 2H), 7.48 (t, J = 8.4 Hz, 1H), 7.39 (s, 1H), 7.00 (d, J = 7.9 Hz, 1H), 5.76 (s, 1H), 4.44 (sxt, J = 8.1 Hz, 1H), 2.88 (d, J = 5.0 Hz, 3H), 2.27-2.18 (m, 2H), 1.82 (dd, J = 11.4, 8.9 Hz, 2H), 1.73-1.53 (m, 2H) |
| 6 | $^1$H NMR (500 MHz, DMSO-d$_6$) δ 8.99 (s, 1H), 8.02 (br. s., 1H), 7.84 (s, 1H), 7.82-7.70 (m, 2H), 7.55 (q, J = 4.8 Hz, 1H), 7.31 (ddd, J = 10.7, 9.2, 5.0 Hz, 1H), 6.97-6.79 (m, 1H), 6.02 (s, 1H), 2.87 (d, J = 5.0 Hz, 3H) |
| 7 | $^1$H NMR (500 MHz, DMSO-d$_6$) δ 8.86 (s, 1H), 7.95 (s, 1H), 7.63 (s, 1H), 7.47 (s, 2H), 7.21 (q, J = 4.5 Hz, 1H), 6.55 (s, 1H), 5.81-5.67 (m, 2H), 2.89 (s, 2H), 2.85 (d, J = 5.0 Hz, 3H), 2.73 (s, 2H), 2.27 (s, 6H) |
| 8 | $^1$H NMR (500 MHz, METHANOL-d$_4$) δ 7.94 (s, 1H), 7.61 (s, 3H), 7.49 (ddd, J = 9.8, 6.6, 3.0 Hz, 1H), 7.14 (td, J = 9.7, 5.0 Hz, 1H), 6.83-6.69 (m, 1H), 5.92 (s, 1H), 3.00 (s, 3H), 2.81 (tt, J = 7.3, 3.8 Hz, 1H), 0.82-0.69 (m, 2H), 0.50-0.36 (m, 2H) |
| 9 | $^1$H NMR (500 MHz, METHANOL-d$_4$) δ 7.94 (s, 1H), 7.07 (d, J = 10.9 Hz, 1H), 6.85 (s, 1H), 6.57 (d, J = 9.4 Hz, 1H), 5.83 (s, 1H), 3.46 (s, 2H), 2.99 (s, 3H), 2.33 (s, 3H), 1.11 (s, 6H) *Note compound was isolated as the TFA salt |
| 10 | $^1$H NMR (500 MHz, METHANOL-d$_4$) δ 7.97 (s, 1H), 7.70 (d, J = 7.9 Hz, 1H), 7.26 (d, J = 7.4 Hz, 1H), 7.18 (t, J = 7.7 Hz, 1H), 6.93 (t, J = 7.2 Hz, 1H), 5.93 (s, 1H), 4.58 (t, J = 8.4 Hz, 1H), 4.18 (t, J = 8.7 Hz, 2H), 3.26 (t, J = 8.4 Hz, 2H), 3.05 (s, 3H), 2.50-2.29 (m, 2H), 2.02 (td, J = 9.4, 2.5 Hz, 2H), 1.85-1.71 (m, 2H) |
| 11 | $^1$H NMR (500 MHz, METHANOL-d$_4$) δ 7.99 (s, 1H), 7.46 (d, J = 8.4 Hz, 1H), 7.23 (d, J = 7.4 Hz, 1H), 7.16 (t, J = 7.7 Hz, 1H), 6.90 (t, J = 7.4 Hz, 1H), 6.17 (s, 1H), 4.20 (t, J = 8.2 Hz, 2H), 3.49 (s, 2H), 3.17 (t, J = 8.2 Hz, 2H), 3.05 (s, 3H), 1.23 (s, 6H) |
| 12 | $^1$H NMR (500 MHz, METHANOL-d$_4$) δ 6.55 (s, 1H), 5.61 (s, 2H), 5.39 (s, 1H), 4.44 (s, 1H), 1.96 (d, J = 1.5 Hz, 6H), 1.87 (s, 2H), 1.72 (s, 2H), 1.63 (s, 3H), 0.94 (s, 6H) |
| 13 | $^1$H NMR (400 MHz, DMSO-d$_6$) δ 9.20 (s, 1H), 8.49 (d, J = 4.0 Hz, 1H), 7.85 (s, 1H), 7.72-7.49 (m, 2H), 7.32-7.08 (m, 1H), 6.00 (s, 1H), 2.88 (d, J = 4.8 Hz, 3H), 2.85-2.73 (m, 1H), 0.75-0.61 (m, 2H), 0.40-0.26 (m, 2H) |
| 14 | $^1$H NMR (400 MHz, DMSO-d$_6$) δ 9.19 (s, 1H), 8.64 (t, J = 6.4 Hz, 1H), 7.87 (s, 1H), 7.71-7.49 (m, 2H), 7.25-7.00 (m, 1H), 6.03 (s, 1H), 4.38 (s, 1H), 3.24 (d, J = 6.4 Hz, 2H), 2.89 (d, J = 4.8 Hz, 3H), 0.94 (s, 6H) |
| 15 | $^1$H NMR (500 MHz, DMSO-d$_6$) δ 9.53 (s, 1H), 8.77 (t, J = 6.4 Hz, 1H), 7.88 (s, 1H), 7.66 (q, J = 4.8 Hz, 1H), 7.20-7.05 (m, 2H), 6.86-6.74 (m, 1H), 5.75 (s, 1H), 4.53 (t, J = 5.9 Hz, 1H), 3.25 (d, J = 6.4 Hz, 2H), 3.04 (d, J = 5.9 Hz, 2H), 2.92-2.82 (m, 3H), 0.68 (s, 6H) |

| | ¹H NMR (METHANOL-d4 equates CDCl₃:MeOD ~1:1 unless otherwise |
|Compound| noted) |
|---|---|
| 16 | ¹H NMR (500 MHz, METHANOL-d₄) δ 7.98 (s, 1H), 7.42 (dt, J = 10.4, 2.5 Hz, 1H), 6.59 (ddd, J = 11.0, 8.3, 3.0 Hz, 1H), 6.05 (s, 1H), 3.92 (d, J = 1.0 Hz, 3H), 3.28 (s, 2H), 3.05 (s, 3H), 0.80 (s, 9H). |
| 17 | ¹H NMR (500 MHz, DMSO-d₆) δ 8.84-8.72 (m, 1H), 7.86 (s, 1H), 7.60 (q, J = 4.6 Hz, 1H), 7.58-7.50 (m, 1H), 6.97 (ddd, J = 11.4, 8.7, 3.2 Hz, 1H), 6.17 (s, 1H), 4.52 (t, J = 5.4 Hz, 1H), 3.80 (s, 3H), 3.18 (d, J = 6.4 Hz, 2H), 3.01 (d, J = 5.0 Hz, 2H), 2.89 (d, J = 4.5 Hz, 3H), 0.63 (s, 6H). |
| 18 | ¹H NMR (500 MHz, DMSO-d₆) δ 9.25 (br. s., 1H), 8.67 (t, J = 6.4 Hz, 1H), 7.87 (s, 1H), 7.67 (d, J = 5.0 Hz, 1H), 7.57 (ddd, J = 10.7, 5.4, 2.7 Hz, 1H), 7.27-7.08 (m, 1H), 6.01 (s, 1H), 4.51 (t, J = 5.9 Hz, 1H), 3.16 (d, J = 6.4 Hz, 2H), 3.00 (d, J = 5.9 Hz, 2H), 2.92-2.85 (m, 3H), 0.63 (s, 6H) |
| 19 | ¹H NMR (500 MHz, DMSO-d₆) δ 9.19 (s, 1H), 7.86-7.70 (m, 3H), 7.66-7.52 (m, 2H), 5.85 (s, 1H), 2.89 (d, J = 4.7 Hz, 3H) |
| 20 | ¹H NMR (500 MHz, DMSO-d₆) δ 9.21 (br. s., 1H), 8.35 (d, J = 3.6 Hz, 1H), 7.90-7.79 (m, 2H), 7.65 (d, J = 5.0 Hz, 1H), 5.86 (s, 1H), 2.89 (d, J = 4.7 Hz, 3H), 2.70 (td, J = 7.3, 3.7 Hz, 1H), 0.68-0.60 (m, 2H), 0.16-0.07 (m, 2H) |
| 21 | ¹H NMR (500 MHz, METHANOL-d₄) δ 7.94 (s, 1H), 7.10 (tt, J = 10.1, 7.2 Hz, 1H), 5.84 (s, 1H), 3.00 (s, 3H), 1.08 (s, 6H) |
| 22 | ¹H NMR (500 MHz, METHANOL-d₄) δ 8.29-8.25 (m, 1H), 8.02-7.99 (m, 1H), 7.73-7.67 (m, 1H), 7.44 (d, J = 7.9 Hz, 1H), 7.00-6.93 (m, 1H), 6.24-6.19 (m, 1H), 4.83-4.64 (m, 1H), 3.05-3.00 (m, 3H), 2.98 -2.92 (m, 1H), 1.23 (dtd, J = 14.7, 8.6, 6.2 Hz, 1H), 1.10-0.95 (m, 1H) |
| 23 | ¹H NMR (500 MHz, METHANOL-d₄) δ 8.12-8.08 (m, 2H), 8.05-8.02 (m, 1H), 7.76 (t, J = 7.9 Hz, 1H), 7.41 (d, J = 7.4 Hz, 1H), 7.30 (d, J = 8.4 Hz, 2H), 7.21 (s, 1H), 7.14 (d, J = 8.4 Hz, 1H), 3.09-2.99 (m, 3H), 1.63-1.57 (m, 2H), 1.43-1.35 (m, 2H) |
| 25 | ¹H NMR (500 MHz, DMSO-d₆) δ 10.24 (s, 1H), 8.75 (t, J = 5.8 Hz, 1H), 8.68-8.61 (m, 1H), 8.57 (s, 1H), 8.21 (dd, J = 4.6, 1.5 Hz, 1H), 8.05-7.85 (m, 2H), 7.50 (dd, J = 8.2, 4.6 Hz, 1H), 6.64 (dd, J = 2.5, 1.9 Hz, 1H), 6.07 (s, 1H), 4.81 (s, 1H), 3.73 (s, 3H), 3.48 (d, J = 5.5 Hz, 2H), 3.39 (d, J = 5.8 Hz, 2H), 3.15 (s, 3H) |
| 26 | ¹H NMR (500 MHz, DMSO-d₆) δ 8.85 (t, J = 5.8 Hz, 1H), 8.51 (s, 1H), 8.14-8.09 (m, 1H), 7.54-7.48 (m, 1H), 7.00 (dd, J = 7.3, 4.9 Hz, 1H), 6.14 (s, 1H), 4.52 (t, J = 4.9 Hz, 1H), 4.43 (t, J = 4.9 Hz, 1H), 3.95 (s, 3H), 3.66-3.60 (m, 1H), 3.57 (q, J = 5.5 Hz, 1H), 2.87 (d, J = 4.9 Hz, 3H) |
| 27 | ¹H NMR (500 MHz, DMSO-d₆) δ 8.73 (d, J = 8.5 Hz, 1H), 8.53 (s, 1H), 8.10 (d, J = 7.9 Hz, 1H), 7.92 (dd, J = 4.9, 1.8 Hz, 1H), 7.79 (s, 1H), 7.46 (d, J = 4.9 Hz, 1H), 7.05 (dd, J = 7.6, 5.2 Hz, 1H), 6.06 (s, 1H), 4.46-4.35 (m, 1H), 3.94 (s, 3H), 2.87 (d, J = 4.9 Hz, 3H), 2.17 (br. s., 2H), 1.73-1.58 (m, 4H) |
| 28 | ¹H NMR (500 MHz, DMSO-d₆) δ 10.16 (s, 1H), 8.62 (d, J = 2.4 Hz, 1H), 8.50 (d, J = 6.7 Hz, 1H), 8.38 (d, J = 7.9 Hz, 1H), 8.21 (dd, J = 4.9, 1.2 Hz, 1H), 7.94 (d, J = 4.9, 1.2 Hz, 1H), 7.85 (s, 1H), 7.63 (d, J = 4.9 Hz, 1H), 7.43 (dd, J = 7.9, 4.9 Hz, 1H), 6.65-6.60 (m, 1H), 5.97 (s, 1H), 4.88 (d, J = 4.3 Hz, 1H), 4.05-3.96 (m, 1H), 3.69 (quin, J = 5.6 Hz, 1H), 2.92 (d, J = 4.9 Hz, 3H), 2.05-1.97 (m, 1H), 1.78-1.70 (m, 1H), 1.68-1.60 (m, 1H), 1.56-1.38 (m, 2H), 1.33-1.21 (m, 1H) |
| 29 | ¹H NMR (500 MHz, DMSO-d₆) δ 10.37 (s, 1H), 8.66 (dd, J = 2.5, 0.6 Hz, 1H), 8.59 (dd, J = 8.2, 1.5 Hz, 1H), 8.32 (d, J = 8.0 Hz, 1H), 8.20 (dd, J = 4.6, 1.5 Hz, 1H), 8.02-7.91 (m, 1H), 7.89 (s, 1H), 7.63 (br. s., 1H), 7.47 (dd, J = 8.2, 4.6 Hz, 1H), 6.65 (dd, J = 2.5, 1.7 Hz, 1H), 5.97 (s, 1H), 4.15-4.03 (m, 1H), 4.08-3.96 (m, 1H), 3.09-2.74 (m, 3H), 1.08 (d, J = 6.7 Hz, 3H) |
| 30 | ¹H NMR (500 MHz, DMSO-d6) δ 10.35 (s, 1H), 8.68-8.63 (m, 2H), 8.62-8.59 (m, 1H), 8.19 (dd, J = 4.6, 1.5 Hz, 1H), 7.97 (d, J = 1.2 Hz, 1H), 7.86 (s, 1H), 7.63 (d, J = 4.9 Hz, 1H), 7.49 (dd, J = 8.2, 4.6 Hz, 1H), 6.69-6.61 (m, 1H), 5.94 (s, 1H), 4.85 (t, J = 5.5 Hz, 1H), 3.47 (q, J = 5.7 Hz, 2H), 3.41-3.37 (m, 2H), 2.92 (d, J = 4.9 Hz, 3H) |
| 31 | ¹H NMR (500 MHz, DMSO-d₆) δ 10.34 (s, 1H), 8.70-8.61 (m, 2H), 8.60-8.54 (m, 1H), 8.17 (dd, J = 4.6, 1.5 Hz, 1H), 7.96 (d, J = 1.2 Hz, 1H), 7.87 (s, 1H), 7.64 (d, J = 5.5 Hz, 1H), 7.48 (dd, J = 8.2, 4.6 Hz, 1H), 6.68-6.58 (m, 1H), 5.95 (s, 1H), 4.58 (s, 1H), 3.29 (d, J = 6.7 Hz, 2H), 2.92 (d, J = 4.9 Hz, 3H), 1.02 (s, 6H) |
| 32 | ¹H NMR (500 MHz, DMSO-d₆) δ 10.12 (s, 1H), 8.41 (d, J = 2.4 Hz, 1H), 8.34 (dd, J = 8.2, 1.2 Hz, 1H), 8.07 (d, J = 8.2 Hz, 1H), 7.95 (dd, J = 4.4, 1.4 Hz, 1H), 7.73 (d, J = 1.2 Hz, 1H), 7.64 (s, 1H), 7.23 (dd, J = 7.9, 4.6 Hz, 1H), 6.40 (t, J = 2.1 Hz, 1H), 5.72 (s, 1H), 3.87-3.81 (m, 1H), 3.13 (d, J = 4.9 Hz, 2H), 2.69 (br. s., 3H), 0.83 (d, J = 6.7 Hz, 3H) |
| 34 | 1H NMR (400 MHz, DMSO-d₆) δ 10.12 (1 H, s), 8.06-8.41 (3 H, m), 7.76-8.01 (2 H, m), 6.31 (1 H, s), 2.62 (1 H, br. s.), 0.85 (2 H, d, J = 5.02 Hz), 0.68 (2 H, br. s.). *Note compound was isolated as the HCl salt. |
| 35 | ¹H NMR (400 MHz, DMSO-d₆) δ 9.85 (s, 1H), 8.52 (s, 1H), 8.36 (s, 1H), 8.02 (s, 1H), 7.95 (d, J = 1.6 Hz, 1H), 7.89 (s, 1H), 7.83 (s, 1H), 6.16 (s, 1H), 4.63 (m, 1H), 3.46 (m, 2H), 2.59 (m, 1H), 0.82 (m, 2H), 0.69 (m, 2H). |
| 36 | ¹H NMR (400 MHz, DMSO-d₆) δ 9.85 (s, 1H), 8.43 (m, 1H), 8.37 (s, 1H), 8.03 (s, 1H), 7.94 (s, 1H), 7.87 (s, 2H), 6.16 (s, 1H), 3.39 (m, 2H), 2.60 (m, 1H), 1.10 (t, J = 7.2 Hz, 3H), 0.84 (m, 2H), 0.69 (m, 2H). |

| Compound | ¹H NMR (METHANOL-d4 equates CDCl₃:MeOD ~1:1 unless otherwise noted) |
|---|---|
| 37 | ¹H NMR (400 MHz, METHANOL-d₄) δ 7.98 (s, 1H), 7.12 (s, 1H), 7.02 (d, J = 11.2 Hz, 1H), 6.61 (d, J = 9.5 Hz, 1H), 6.29 (s, 1H), 5.49 (d, J = 1.3 Hz, 2H), 2.65 (td, J = 6.9, 3.6 Hz, 1H), 2.35 (s, 3H), 0.93 (d, J = 6.6 Hz, 2H), 0.78-0.63 (m, 2H). *Note compound was isolated as the TFA salt. |
| 38 | ¹H NMR (500 MHz, METHANOL-d₄) δ 7.92 (s, 1H), 7.04 (dd, J = 10.4, 2.0 Hz, 1H), 6.90 (s, 1H), 6.59 (d, J = 9.4 Hz, 1H), 2.89-2.78 (m, 1H), 2.59 (dt, J = 6.9, 3.5 Hz, 1H), 2.35 (s, 3H), 0.94-0.85 (m, 2H), 0.80-0.72 (m, 2H), 0.71-0.63 (m, 2H), 0.50-0.41 (m, 2H) |
| 39 | ¹H NMR (400 MHz, DMSO-d₆) δ 9.86 (s, 1H), 8.41 (m, 1H), 8.30 (m, 1H), 7.78 (m, 2H), 7.55 (m, 1H), 6.10 (s, 1H), 3.56 (m, 2H), 2.67 (m, 3H), 2.58 (m, 1H), 1.17 (m, 3H), 0.83 (m, 2H), 0.68 (m, 2H) |
| 40 | ¹H NMR (400 MHz, DMSO-d₆) δ 10.41 (s, 1H), 9.87 (s, 1H), 8.43 (s, 1H), 8.07 (s, 1H), 7.99 (m, 1H), 7.83 (s, 1H), 7.53 (m, 2H), 7.31 (m, 2H), 7.07 (m, 2H), 6.21 (s, 1H), 2.62 (m, 1H), 0.85 (m, 2H), 0.68 (m, 2H) |
| 41 | ¹H NMR (400 MHz, DMSO-d₆) δ 9.10 (s, 1H), 7.70 (d, J = 8 Hz, 2H), 7.56 (s, 1H), 7.50 (s, 1H), 7.27 (m, 2H), 6.91 (t, J = 7.2 Hz, 1H), 6.15 (s, 1H), 3.01 (m, 4H), 2.55 (m, 1H), 0.82 (m, 2H), 0.67 (m, 2H), 0.51 (m, 4H) |
| 42 | ¹H NMR (400 MHz, DMSO-d₆) δ 8.96 (s, 1H), 7.72 (s, 1H), 7.46 (s, 1H), 7.19 (s, 2H), 6.60 (s, 1H), 6.24 (s, 1H), 2.78 (m, 2H), 2.57 (m, 1H), 2.26 (s, 6H), 0.82 (m, 2H), 0.65 (m, 10H) |
| 43 | ¹H NMR (400 MHz, DMSO-d₆) δ 8.94 (s, 1H), 7.54 (s, 1H), 7.45 (s, 1H), 7.33 (s, 2H), 6.56 (s, 1H), 6.15 (s, 1H), 3.04 (m, 4H), 2.52 (m, 1H), 2.25 (s, 6H), 0.81 (m, 2H), 0.67 (m, 2H), 0.47 (m, 4H) |
| 44 | ¹H NMR (400 MHz, DMSO-d₆) δ 9.33 (s, 1H), 8.64 (d, J = 8.0 Hz, 1H), 7.89 (s, 1H), 7.84 (s, 1H), 7.65 (m, 1H), 7.28 (m, 1H), 6.38 (s, 1H), 4.44 (m, 1H), 2.52 (m, 1H), 2.22 (m, 2H), 1.67 (m, 4H), 0.83 (m, 2H), 0.68 (m, 2H) |
| 46 | ¹H NMR (400 MHz, DMSO-d₆) δ 9.04 (s, 1H), 8.33 (m, 1H), 8.32 (s, 1H), 7.91 (m, 1H), 7.81 (s, 1H), 7.68 (s, 1H), 7.08 (s, 2H), 6.64 (s, 1H), 6.15 (s, 1H), 2.56 (m, 1H), 2.08 (s, 6H), 0.82 (m, 2H), 0.69 (m, 2H). |
| 47 | ¹H NMR (400 MHz, DMSO-d₆) δ 9.40 (s, 1H), 8.14 (m, 1H), 7.85 (s, 1H), 7.81 (m, 2H), 7.42 (m, 1H), 7.34 (dd, J = 15.2, 8.0 Hz, 1H), 7.24 (m, 1H), 6.79 (m, 1H), 6.17 (s, 1H), 2.56 (m, 1H), 0.82 (m, 2H), 0.69 (m, 2H). |
| 49 | ¹H NMR (500 MHz, METHANOL-d₄) δ 7.92 (s, 1H), 7.03 (s, 2H), 6.68 (s, 1H), 5.85 (s, 1H), 3.98-3.84 (m, 1H), 2.29 (s, 6H), 2.14-2.01 (m, 2H), 1.87-1.76 (m, 2H), 1.72-1.61 (m, 4H) |
| 50 | ¹H NMR (500 MHz, METHANOL-d₄) δ 7.94 (s, 1H), 7.04 (s, 2H), 6.69 (s, 1H), 5.82 (s, 1H), 3.38-3.32 (m, 2H), 2.53-2.45 (m, 2H), 2.29 (d, J = 1.0 Hz, 12H), 2.02-1.83 (m, 2H) |
| 51 | ¹H NMR (500 MHz, METHANOL-d₄) δ 7.98-7.92 (m, 1H), 7.06-6.98 (m, 2H), 6.74-6.64 (m, 1H), 5.83 (s, 1H), 3.14 (d, J = 6.9 Hz, 2H), 2.33-2.24 (m, 6H), 1.40-1.31 (m, 2H), 0.68-0.58 (m, 1H), 0.33 (q, J = 5.0 Hz, 1H). *Note compound was isolated as the TFA salt. |
| 52 | ¹H NMR (500 MHz, DMSO-d₆) δ 8.95 (s, 1H), 8.33 (d, J = 2.5 Hz, 1H), 7.94 (d, J = 2.5 Hz, 1H), 7.82 (s, 1H), 7.17 (t, J = 5.7 Hz, 1H), 7.05 (s, 2H), 667-6.51 (m, 1H), 5.87 (s, 1H), 4.93 (t, J = 5.4 Hz, 1H), 3.65 (q, J = 5.9 Hz, 2H), 2.25 (s, 6H) |
| 53 | ¹H NMR (500 MHz, METHANOL-d₄) δ 7.94 (s, 1H), 7.03 (s, 2H), 6.68 (s, 1H), 5.82 (s, 1H), 3.10 (d, J = 6.9 Hz, 2H), 2.28 (s, 6H), 2.03 (dt, J = 13.4, 6.7 Hz, 1H), 1.04 (d, J = 6.4 Hz, 6H) |
| 54 | ¹H NMR (500 MHz, METHANOL-d₄) δ 7.93 (s, 1H), 7.03 (s, 2H), 6.68 (s, 1H), 5.82 (s, 1H), 3.24 (t, J = 6.9 Hz, 2H), 2.28 (s, 6H), 1.76 (sxt, J = 7.3 Hz, 2H), 1.05 (t, J = 7.4 Hz, 3H) |
| 55 | ¹H NMR (500 MHz, METHANOL-d₄) δ 7.93 (s, 1H), 7.03 (s, 2H), 6.68 (s, 1H), 5.81 (s, 1H), 3.27 (t, J = 7.2 Hz, 2H), 1.73 (quin, J = 7.2 Hz, 2H), 1.52-1.33 (m, 4H), 0.99-0.84 (m, 3H) |
| 56 | ¹H NMR (500 MHz, METHANOL-d₄) δ 7.94 (s, 1H), 7.03 (s, 2H), 6.69 (s, 1H), 5.85 (s, 1H), 3.74-3.61 (m, 2H), 3.46 (t, J = 5.4 Hz, 2H), 3.41 (s, 3H), 2.29 (s, 6H) |
| 57 | ¹H NMR (500 MHz, METHANOL-d₄) δ 7.95 (s, 1H), 7.03 (s, 2H), 6.69 (s, 1H), 5.88 (s, 1H), 3.24 (s, 2H), 2.29 (s, 6H), 1.32 (s, 6H) |
| 58 | ¹H NMR (500 MHz, METHANOL-d₄) δ 7.97 (s, 1H), 7.06 (s, 2H), 6.71 (s, 1H), 6.01 (s, 1H), 3.78 (t, J = 6.2 Hz, 2H), 3.44 (t, J = 6.2 Hz, 2H), 2.95 (s, 6H), 2.29 (s, 6H) |
| 61 | ¹H NMR (500 MHz, DMSO-d₆) δ 9.95 (s, 1H), 9.12 (s, 1H), 8.95 (s, 1H), 8.25 (br. s., 1H), 8.03 (br. s., 1H), 7.94 (s, 1H), 7.86 (s, 1H), 7.06 (s, 2H), 6.65 (s, 1H), 6.32 (s, 1H), 2.25 (s, 6H) |
| 62 | ¹H NMR (500 MHz, METHANOL-d₄) δ 7.99 (s, 1H), 7.20 (s, 1H), 7.06 (s, 2H), 6.69 (s, 1H), 5.87 (s, 1H), 3.73 (s, 3H), 2.32-2.25 (m, 9H) |
| 63 | |
| 64 | ¹H NMR (500 MHz, DMSO-d₆) δ 9.59 (s, 1H), 9.06 (s, 1H), 8.72 (d, J = 2.5 Hz, 1H), 8.40 (dd, J = 4.5, 1.5 Hz, 1H), 8.28 (br. s., 1H), 8.03 (br. s., 1H), 7.98-7.91 (m, 2H), 7.90-7.84 (m, 1H), 7.49 (dd, J = 8.2, 4.7 Hz, 1H), 7.06 (s, 2H), 6.64 (s, 1H), 2.25 (s, 6H) |
| 70 | ¹H NMR (500 MHz, DMSO-d₆) δ 9.19(s, 1H), 9.03 (d, J = 4.0 Hz, 1H), 8.29 (br. s., 1H), 8.04 (d, J = 2.5 Hz, 1H), 7.84 (s, 1H), 7.26 (s, 2H), 6.61 (s, 1H), 3.13-3.04 (m, 1H), 2.24 (s, 6H), 0.89-0.74 (m, 4H) |

| | ¹H NMR (METHANOL-d4 equates CDCl₃:MeOD ~1:1 unless otherwise Compound noted) |
|---|---|
| 71 | ¹H NMR (500 MHz, DMSO-d₆) δ 9.49 (s, 1H), 9.16 (br. s., 1H), 8.24 (br. s., 1H), 8.03 (br. s., 1H), 7.87 (s, 1H), 7.44 (d, J = 11.9 Hz, 1H), 7.29 (s, 1H), 6.60 (d, J = 9.4 Hz, 1H), 3.05 (br. s., 1H), 2.29 (s, 3H), 0.91-0.72 (m, 4H) |
| 72 | ¹H NMR (500 MHz, METHANOL-d₄) δ 7.99 (dd, J = 7.9, 1.5 Hz, 1H), 7.94 (s, 1H), 7.08-6.99 (m, 1H), 7.00-6.89 (m, 2H), 3.92 (s, 3H), 3.12-3.00 (m, 1H), 1.00-0.90 (m, 2H), 0.76 (dd, J = 3.5, 1.5 Hz, 2H) |
| 73 | ¹H NMR (500 MHz, DMSO-d₆) δ 9.45 (s, 1H), 9.00-8.83 (m, 1H), 8.18 (br. s., 1H), 8.03 (br. s., 1H), 7.95 (s, 1H), 7.87 (s, 1H), 7.31 (d, J = 11.9 Hz, 1H), 7.26 (s, 1H), 6.61 (d, J = 9.9 Hz, 1H), 3.04 (d, J = 4.5 Hz, 3H), 2.29 (s, 3H) |
| 74 | ¹H NMR (500 MHz, DMSO-d₆) δ 8.82 (q, J = 4.5 Hz, 1H), 8.22 (br. s., 1H), 8.14 (s, 1H), 7.86-7.79 (m, 3H), 7.05 (d, J = 4.0 Hz, 2H), 6.97-6.86 (m, 1H), 3.84 (s, 3H), 3.00 (d, J = 5.0 Hz, 3H) |
| 76 | ¹H NMR (500 MHz, METHANOL-d₄) δ 7.93 (s, 1H), 7.50-7.40 (m, 2H), 7.37-7.25 (m, 3H), 5.48 (s, 1H), 3.41 (s, 3H), 2.93-2.83 (m, 1H), 2.79 (s, 3H), 0.86-0.78 (m, 2H), 0.55-0.44 (m, 2H) |
| 77 | ¹H NMR (500 MHz, METHANOL-d₄) δ 7.91 (s, 1H), 7.66 (d, J = 8.4 Hz, 1H), 7.14-7.05 (m, 1H), 7.03-6.94 (m, 2H), 5.89 (s, 1H), 3.89 (s, 3H), 3.00 (s, 3H), 2.89-2.76 (m, 1H), 0.82-0.71 (m, 2H), 0.46-0.40 (m, 2H) |
| 78 | ¹H NMR (500 MHz, METHANOL-d₄) δ 7.99 (s, 1H), 7.25 (d, J = 7.4 Hz, 1H), 7.18 (t, J = 7.7 Hz, 1H), 6.93 (t, J = 7.2 Hz, 1H), 5.90 (s, 1H), 4.15 (t, J = 8.4 Hz, 2H), 3.24 (t, J = 8.4 Hz, 2H), 3.04 (s, 3H), 2.97-2.89 (m, 1H), 0.86 (dd, J = 6.9, 1.5 Hz, 2H), 0.63 (dd, J = 4.0, 1.5 Hz, 2H) |
| 79 | ¹H NMR (500 MHz, METHANOL-d₄) δ 7.96 (s, 1H), 7.38 (dt, J = 10.2, 2.6 Hz, 1H), 6.61 (ddd, J = 11.0, 8.3, 3.0 Hz, 1H), 6.02 (s, 1H), 3.91 (d, J = 1.0 Hz, 3H), 3.02 (s, 3H), 2.84 (tt, J = 7.3, 3.8 Hz, 1H), 0.84-0.73 (m, 2H), 0.55-0.46 (m, 2H) |
| 80 | ¹H NMR (500 MHz, METHANOL-d₄) δ 7.94 (s, 1H), 7.70-7.65 (m, 1H), 7.15-7.07 (m, 1H), 7.03-6.95 (m, 2H), 5.90 (s, 1H), 4.31 (s, 1H), 3.90 (s, 3H), 3.41 (s, 2H), 3.00 (s, 3H), 1.14 (s, 6H). |
| 81 | ¹H NMR (500 MHz, DMSO-d₆) δ 8.88-8.59 (m, 2H), 7.87 (s, 1H), 7.71-7.50 (m, 2H), 6.94 (ddd, J = 11.4, 8.4, 3.0 Hz, 1H), 6.22 (s, 1H), 4.46 (s, 1H), 3.83 (s, 3H), 3.28 (d, J = 6.4 Hz, 2H), 2.90 (d, J = 4.5 Hz, 3H), 0.96 (s, 6H). |
| 82 | ¹H NMR (500 MHz, METHANOL-d₄) δ 7.92 (s, 1H), 7.18 (dd, J = 7.9, 1.5 Hz, 1H), 6.82 (t, J = 8.2 Hz, 1H), 6.63 (dd, J = 8.2, 1.2 Hz, 1H), 5.87 (s, 1H), 4.33-4.29 (m, 2H), 4.28-4.25 (m, 2H), 3.39 (s, 2H), 2.98 (s, 3H), 1.13 (s, 6H) *Note compound was isolated as the TFA salt |
| 83 | ¹H NMR (500 MHz, DMSO-d₆) δ 8.77 (s, 1H), 8.05 (br. s., 1H), 7.87 (s, 1H), 7.80 (br. s., 1H), 7.72 (dt, J = 11.4, 2.2 Hz, 1H), 7.55 (q, J = 4.6 Hz, 1H), 6.92 (ddd, J = 11.4, 8.4, 3.0 Hz, 1H), 6.22 (s, 1H), 3.84 (s, 3H), 2.89 (d, J = 4.5 Hz, 3H) |
| 84 | ¹H NMR (500 MHz, METHANOL-d₄) δ 7.91 (s, 1H), 7.20 (dd, J = 8.2, 1.2 Hz, 1H), 6.85 (t, J = 8.2 Hz, 1H), 6.65 (dd, J = 8.2, 1.2 Hz, 1H), 5.86 (s, 1H), 4.34-4.30 (m, 2H), 4.30-4.26 (m, 2H), 2.99 (s, 3H), 2.82 (tt, J = 7.3, 3.8 Hz, 1H), 0.80-0.72 (m, 2H), 0.50-0.36 (m, 2H) *Note compound was isolated as the TFA salt |
| 85 | ¹H NMR (500 MHz, DMSO-d₆) δ 9.89 (s, 1H), 8.80 (d, J = 3.1 Hz, 1H), 8.52 (d, J = 2.4 Hz, 1H), 7.98-7.88 (m, 2H), 7.82 (s, 1H), 7.65 (d, J = 4.9 Hz, 1H), 7.47 (d, J = 7.3 Hz, 1H), 7.35 (d, J = 8.5 Hz, 1H), 6.59 (s, 1H), 6.50 (s, 1H), 2.91 (d, J = 4.9 Hz, 3H), 2.83 (td, J = 7.3, 3.7 Hz, 1H), 0.76-0.69 (m, 2H), 0.51 (d, J = 3.1 Hz, 2H) |
| 86 | ¹H NMR (500 MHz, DMSO-d₆) δ 9.78 (s, 1H), 8.84 (d, J = 4.3 Hz, 1H), 8.11 (d, J = 7.3 Hz, 2H), 7.89 (s, 1H), 7.83 (t, J = 7.6 Hz, 1H), 7.61 (d, J = 4.9 Hz, 1H), 7.55 (d, J = 7.3 Hz, 1H), 7.52-7.47 (m, 2H), 7.46-7.42 (m, 1H), 7.36 (d, J = 7.9 Hz, 1H), 6.91 (s, 1H), 2.92 (d, J = 4.9 Hz, 3H), 2.85 (dt, J = 7.3, 3.7 Hz, 1H), 0.80-0.72 (m, 2H), 0.62-0.54 (m, 2H) |
| 87 | ¹H NMR (500 MHz, DMSO-d₆) δ 9.65 (s, 1H), 8.80 (d, J = 3.7 Hz, 1H), 7.87 (s, 1H), 7.79-7.73 (m, 1H), 7.63 (d, J = 8.5 Hz, 1H), 7.59 (d, J = 4.9 Hz, 1H), 7.10 (d, J = 7.9 Hz, 1H), 6.59 (s, 1H), 4.50-4.42 (m, 2H), 4.25-4.19 (m, 2H), 2.89-2.86 (m, 4H), 0.82-0.73 (m, 2H), 0.57 (br. s., 2H) |
| 88 | ¹H NMR (500 MHz, DMSO-d₆) δ 9.62 (s, 1H), 8.82 (d, J = 3.7 Hz, 1H), 7.89-7.83 (m, 2H), 7.73 (t, J = 7.9 Hz, 1H), 7.58 (d, J = 4.9 Hz, 1H), 7.08-7.04 (m, 1H), 6.69 (s, 1H), 4.05 (t, J = 7.0 Hz, 2H), 2.90 (d, J = 4.9 Hz, 3H), 2.55 (d, J = 5.5 Hz, 3H), 2.04 (quin, J = 7.5 Hz, 2H), 0.80-0.73 (m, 2H), 0.62-0.54 (m, 2H) |
| 89 | ¹H NMR (500 MHz, DMSO-d₆) δ 10.03 (s, 1H), 8.80 (d, J = 3.7 Hz, 1H), 8.69 (s, 1H), 7.96 (t, J = 7.9 Hz, 1H), 7.90 (s, 1H), 7.63 (d, J = 4.9 Hz, 1H), 7.48 (d, J = 7.3 Hz, 1H), 7.45 (d, J = 8.5 Hz, 1H), 7.06 (d, J = 2.4 Hz, 1H), 6.50 (s, 1H), 2.91 (d, J = 4.9 Hz, 3H), 2.81 (td, J = 7.3, 3.7 Hz, 1H), 0.74-0.66 (m, 2H), 0.52-0.43 (m, 2H) |
| 90 | ¹H NMR (500 MHz, DMSO-d₆) δ 9.66 (s, 1H), 8.83 (br. s., 1H), 7.93 (s, 1H), 7.87 (s, 1H), 7.75 (t, J = 8.1 Hz, 1H), 7.57 (br. s., 1H), 7.09 (d, J = 7.7 Hz, 1H), 6.67 (s, 1H), 4.43-4.33 (m, 1H), 4.09 (t, J = 9.6 Hz, 1H), 3.76 (d, J = 6.7 Hz, 1H), 2.88 (s, 6H), 0.77 (d, J = 5.4 Hz, 2H), 0.56 (br. s., 2H) |

| Compound | ¹H NMR (METHANOL-d4 equates CDCl₃:MeOD ~1:1 unless otherwise noted) |
|---|---|
| 91 | ¹H NMR (500 MHz, DMSO-d₆) δ 8.51 (d, J = 2.4 Hz, 1H), 8.21 (d, J = 3.7 Hz, 1H), 7.93-7.90 (m, 2H), 7.52 (t, J = 8.2 Hz, 1H), 6.87 (d, J = 7.9 Hz, 1H), 6.46 (d, J = 2.4 Hz, 1H), 6.21 (s, 2H), 6.11 (s, 1H), 2.93 (d, J = 4.3 Hz, 3H), 2.66 (dt, J = 7.5 , 3.9 Hz, 1H), 0.54-0.45 (m, 2H), 0.09 (br. s., 2H) |
| 92 | N/A |
| 93 | N/A |
| 94 | N/A |
| 95 | N/A |
| 96 | N/A |
| 97 | N/A |
| 98 | ¹H NMR (500 MHz, DMSO-d₆) δ 9.12 (s, 1H), 8.41 (d, J = 5.7 Hz, 2H), 8.34 (d, J = 3.7 Hz, 1H), 7.61 (dd, J = 8.1, 4.4 Hz, 1H), 7.56 (d, J = 4.7 Hz, 1H), 5.87 (s, 1H), 2.89-2.85 (m, 3H), 2.77 (d, J = 3.7 Hz, 1H), 0.68 (d, J = 5.7 Hz, 2H), 0.27 (br. s., 2H) |
| 99 | ¹H NMR (500 MHz, DMSO-d₆) δ 9.14 (s, 1H), 8.46 (s, 1H), 8.38 (d, J = 3.0 HZ, 1H), 8.35 (d, J = 3.7 Hz, 1H), 8.24 (d, J = 7.7 Hz, 1H), 7.62 (dd, J = 7.9, 4.9 Hz, 1H), 7.47 (br. s., 1H), 7.31 (br. s., 1H), 6.89 (s, 1H), 5.71 (s, 1H), 2.84 (d, J = 4.7 Hz, 3H), 2.75 (d, J = 4.0 Hz, 1H), 0.68-0.63 (m, 2H), 0.22 (br. s., 2H) |
| 100 | ¹H NMR (500 MHz, DMSO-d₆) δ 8.66 (s, 1H), 8.45 (d, J = 3.7 Hz, 1H), 8.43-8.39 (m, 1H), 8.29 (d, J = 7.9 Hz, 1H), 7.79 (s, 1H), 7.68 (dd, J = 7.9, 4.9 Hz, 1H), 7.52 (d, J = 4.9 Hz, 1H), 6.65 (s, 1H), 5.71 (s, 1H), 2.81 (d, J = 4.9 Hz, 3H), 2.77 (td, J = 7.3, 3.7 Hz, 1H), 2.21 (s, 3H), 0.68-0.61 (m, 2H), 0.25-0.18 (m, 2H) |
| 101 | ¹H NMR (500 MHz, DMSO-d₆) δ 8.84 (s, 1H), 8.50 (d, J = 3.7 Hz, 1H), 8.39 (d, J = 8.1 Hz, 1H), 8.32 (d, J = 4.0 Hz, 1H), 7.81 (s, 1H), 7.65 (s, 1H), 7.58-7.50 (m, 2H), 6.29 (s, 1H), 5.85 (s, 1H), 2.84 (d, J = 4.7 Hz, 3H), 2.79 (td, J = 7.2, 3.7 Hz, 1H), 2.33 (s, 3H), 0.74-0.64 (m, 2H), 0.33-0.22 (m, 2H) |
| 102 | ¹H NMR (500 MHz, DMSO-d₆) δ 10.45 (s, 1H), 8.51 (d, J = 2.4 Hz, 1H), 8.49 (d, J = 4.4 Hz, 1H), 8.17 (d, J = 3.7 Hz, 1H), 7.84 (s, 1H), 7.61 (d, J = 4.7 Hz, 1H), 7.40 (dd, J = 8.2, 4.5 Hz, 1H), 7.22-7.17 (m, 1H), 6.42 (d, J = 2.0 Hz, 1H), 5.89 (s, 1H), 2.92 (d, J = 4.7 Hz, 3H), 2.82 (dt, J = 7.2, 3.5 Hz, 1H), 2.38 (s, 3H), 0.77-0.71 (m, 2H), 0.42-0.36 (m, 2H) |
| 103 | ¹H NMR (500 MHz, DMSO-d₆) δ 11.48 (s, 1H), 9.12 (d, J = 4.4 Hz, 1H), 8.64 (d, J = 8.4 Hz, 1H), 8.49 (br. s., 1H), 8.23 (d, J = 3.7 Hz, 1H), 7.87 (s, 1H), 7.67-7.54 (m, 2H), 5.87 (s, 1H), 2.91 (d, J = 4.7 Hz, 3H), 2.84 (d, J = 4.7 Hz, 3H), 2.72 (s, 1H), 0.76 (d, J = 5.4 Hz, 2H), 0.46 (br. s., 2H) |
| 104 | ¹H NMR (500 MHz, DMSO-d₆) δ 11.38 (s, 1H), 8.94 (s, 1H), 8.65 (d, J = 8.4 Hz, 1H), 8.49 (br. s., 1H), 8.26 (d, J = 4.4 Hz, 1H), 7.87 (s, 1H), 7.67-7.53 (m, 2H), 5.88 (s, 1H), 3.17 (d, J = 6.7 Hz, 2H), 2.91 (d, J = 4.7 Hz, 3H), 2.85 (d, J = 3.7 Hz, 1H), 0.92 (s, 9H), 0.75 (d, J = 5.7 Hz, 2H), 0.45 (br. s., 2H) |
| 105 | NA |
| 106 | ¹H NMR (500 MHz, DMSO-d₆) δ 11.29 (s, 1H), 9.26 (br. s., 1H), 8.65 (d, J = 8.4 Hz, 1H), 8.50 (br. s., 1H), 8.26 (d, J = 3.7 Hz, 1H), 7.87 (s, 1H), 7.63-7.56 (m, 2H), 5.89 (s, 1H), 4.63 (t, J = 5.0 Hz, 1H), 4.53 (t, J = 5.0 Hz, 1H), 3.72-3.57 (m, 2H), 2.91 (d, J = 5.0 Hz, 3H), 2.85 (d, J = 3.7 Hz, 1H), 0.75 (d, J = 5.4 Hz, 2H), 0.44 (br. s., 2H) |
| 107 | ¹H NMR (500 MHz, DMSO-d₆) δ 11.36 (s, 1H), 9.04 (br. s., 1H), 8.64 (d, J = 9.2 Hz, 1H), 8.49 (d, J = 3.7 Hz, 1H), 8.25 (d, J = 4.3 Hz, 1H), 7.87 (s, 1H), 7.59 (td, J = 9.0, 4.6 Hz, 2H), 5.89 (s, 1H), 3.63-3.56 (m, 2H), 3.42-3.35 (m, 2H), 3.27 (s, 3H), 2.91 (d, J = 4.9 Hz, 3H), 2.85 (td, J = 7.3, 3.7 Hz, 1H), 0.79-0.71 (m, 2H), 0.48-0.39 (m, 2H) |
| 112 | ¹H NMR (500 MHz, DMSO-d₆) δ 9.17 (br. s., 1H), 8.52 (t, J = 6.2 Hz, 1H), 7.84 (s, 1H), 7.72-7.56 (m, 2H), 5.86 (s, 1H), 4.59 (t, J = 6.2 Hz, 1H), 3.24-3.14 (m, 1H), 3.14-3.07 (m, 1H), 3.04 (dd, J = 5.7, 4.7 Hz, 2H), 2.93-2.86 (m, 3H), 0.82 (s, 3H). Enatiomeric excess not determined |
| 113 | ¹H NMR (500 MHz, DMSO-d₆) δ 9.27 (s, 1H), 8.82 (t, J = 6.4 Hz, 1H), 7.86 (s, 1H), 7.84-7.76 (m, 2H), 7.74-7.66 (m, 2H), 7.62 (d, J = 1.0 Hz, 1H), 7.58-7.49 (m, 2H), 7.21 (d, J = 6.9 Hz, 1H), 5.83 (s, 1H), 3.19-3.02 (m, 4H), 2.93-2.87 (m, 3H), 0.90 (s, 3H). Enantiomeric excess not determined |
| 114 | (as TFA salt) ¹H NMR (500 MHz, DMSO-d₆) δ 8.88 (s, 1H), 8.82 (d, J = 3.5 Hz, 1H0, 8.30 (s, 1H), 7.80 (s, 1H), 7.44 (d, J = 5.0 Hz, 1H), 7.01 (s, 2H), 6.69 (s, 1H), 5.72 (s, 1H), 2.87-2.83 (m, 3H), 2.79 (td, J = 7.2, 3.5 Hz, 1H), 2.28 (s, 6H), 0.74-0.63 (m, 2H), 0.33-0.22 (m, 2H). |
| 115 | ¹H NMR (500 MHz, CHLOROFORM-d/METHANOL-d₄) δ 7.91 (s, 1H), 6.96 (s, 2H), 6.75 (s, 1H), 5.82 (s, 1H), 4.33 (br. s., 2H), 3.37 (s, 2H), 3.28 (d, J = 4.5 Hz, 3H), 2.98 (s, 3H), 2.31 (s, 6H), 0.58 (s, 3H). |
| 116 | ¹H NMR (500 MHz, DMSO-d₆) δ 9.27 (s, 1H), 8.66 (d, J = 3.5 Hz, 1H), 7.88-7.78 (m, 3H), 7.70 (d, J = 7.9 Hz, 1H), 7.65-7.58 (m, 2H), 7.56-7.46 (m, 2H), 7.28 (d, J = 6.9 Hz, 1H), 5.78 (s, 1H), 2.88 (d, J = 5.0 Hz, 3H), 2.68 (tq, J = 7.4, 3.8 Hz, 1H), 0.62-0.53 (m, 2H), 0.31-0.20 (m, 2H). |

| Compound | ¹H NMR (METHANOL-d4 equates CDCl₃:MeOD ~1:1 unless otherwise noted) |
|---|---|
| 117 | ¹H NMR (500 MHz, DMSO-d₆) δ 9.03 (s, 1H), 8.29 (br. s., 1H), 7.83 (s, 1H), 7.80 (br. s., 1H), 7.46 (d, J = 5.0 Hz, 1H), 7.39-7.34 (m, 1H), 7.30-7.16 (m, 2H), 7.13-6.94 (m, 1H), 5.77 (s, 1H), 2.87 (d, J = 4.5 Hz, 3H), 1.28 (s, 9H). |
| 118 | ¹H NMR (500 MHz, DMSO-d₆) δ 9.28 (s, 1H), 8.74 (d, J = 4.0 Hz, 1H), 7.87 (s, 1H), 7.84-7.76 (m, 2H), 7.70 (d, J = 7.9 Hz, 1H), 7.64-7.58 (m, 2H), 7.56 (d, J = 4.5 Hz, 1H), 7.48 (t, J = 7.9 Hz, 1H), 7.26 (d, J = 7.4 Hz, 1H), 5.81 (s, 1H), 4.74-4.57 (m, 1H), 2.89 (d, J = 4.5 Hz, 3H), 2.77 (dd, J = 9.2, 4.7 Hz, 1H), 1.08-0.95 (m, 1H), 0.75-0.57 (m, 1H). Enantiomeric excess not determined. |

What is claimed is:

1. A compound of the formula

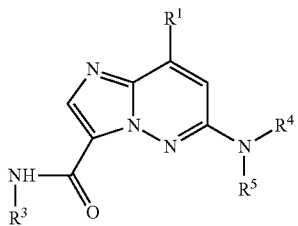

wherein $R^1$ is —$NHR^2$;

$R^2$ is $C_1$-$C_6$ alkyl or $C_3$-$C_8$ cycloalkyl;

$R^3$ is H, $C_1$-$C_6$ alkyl, hydroxy $C_1$-$C_6$ alkyl or mono or bicyclic $C_3$-$C_8$ cycloalkyl;

$R^4$ is H, $C_1$-$C_6$ alkyl, mono or bicyclic $C_3$-$C_6$ cycloalkyl, phenyl, or pyridyl, any of said groups other than H substituted with 0-4 $R^7$;

$R^5$ is H or $C_1$-$C_4$ alkyl;

$R^7$ is H, halo, CN, $CF_3$, $C_1$-$C_4$ alkyl, $C_1$-$C_4$ alkoxy, —CONH $C_1$-$C_6$ alkyl, —CONH halo $C_1$-$C_6$ alkyl, —CONH halo $C_1$-$C_6$ alkoxy, heteroaryl, or aryl, said aryl and heteroaryl groups substituted with 0-2 $R^8$;

$R^8$ is H, halo, $CF_3$, $C_1$-$C_4$ alkyl or $C_1$-$C_4$ alkoxy;

or a pharmaceutically acceptable salt, tautomer or stereoisomer thereof.

2. The compound according to claim 1

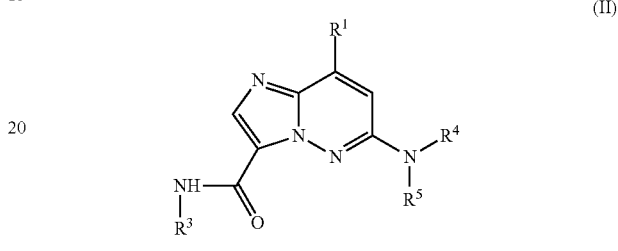

wherein $R^1$ is —$NHR^2$;

$R^2$ is $CH_3$ or cyclopropyl;

$R^3$ is H, $C_1$-$C_6$ alkyl, hydroxy $C_1$-$C_6$ alkyl or mono or bicyclic $C_3$-$C_8$ cycloalkyl;

$R^4$ is H, $C_1$-$C_6$ alkyl, mono or bicyclic $C_3$-$C_6$ cycloalkyl, phenyl, or pyridyl, any of said groups other than H substituted with 0-4 $R^7$;

$R^5$ is H or $C_1$-$C_4$ alkyl;

$R^7$ is H, halo, CN, $CF_3$, $C_1$-$C_4$ alkyl, $C_1$-$C_4$ alkoxy, —CONH $C_1$-$C_6$ alkyl, —CONH halo $C_1$-$C_6$ alkyl, —CONH halo $C_1$-$C_6$ alkoxy, heteroaryl, or aryl, said aryl and heteroaryl groups substituted with 0-2 $R^8$;

$R^8$ is H, halo, $CF_3$, $C_1$-$C_4$ alkyl or $C_1$-$C_4$ alkoxy;

or a pharmaceutically acceptable salt, tautomer or stereoisomer thereof.

3. A pharmaceutical composition comprising one or more compounds according to claim 1 and a pharmaceutically acceptable carrier or diluent.

* * * * *